United States Patent
Fudaba et al.

(10) Patent No.: US 9,492,920 B2
(45) Date of Patent: Nov. 15, 2016

(54) CONTROL APPARATUS AND CONTROL METHOD FOR MASTER-SLAVE ROBOT, MASTER-SLAVE ROBOT, CONTROL PROGRAM FOR MASTER-SLAVE ROBOT, AND INTEGRATED ELECTRONIC CIRCUIT FOR CONTROLLING MASTER-SLAVE ROBOT

(71) Applicant: Panasonic Intellectual Property Management Co., Ltd., Osaka (JP)

(72) Inventors: Yudai Fudaba, Osaka (JP); Yuko Tsusaka, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 28 days.

(21) Appl. No.: 14/730,188

(22) Filed: Jun. 3, 2015

(65) Prior Publication Data
US 2015/0360365 A1 Dec. 17, 2015

(30) Foreign Application Priority Data
Jun. 16, 2014 (JP) .................... 2014-123614

(51) Int. Cl.
*B25J 3/04* (2006.01)
*B25J 9/16* (2006.01)

(52) U.S. Cl.
CPC ............... *B25J 3/04* (2013.01); *A61B 34/37* (2016.02); *A61B 34/76* (2016.02); *A61B 34/77* (2016.02); *B25J 9/1679* (2013.01); *B25J 9/1689* (2013.01)

(58) Field of Classification Search
CPC ............. A61B 34/37; A61B 34/76; A61B 34/77; A61B 2090/5025; B25J 3/00; B25J 3/04; B25J 9/1607; B25J 9/1679; B25J 9/1689
See application file for complete search history.

(56) References Cited

U.S. PATENT DOCUMENTS

2014/0222023 A1* 8/2014 Kim .................. A61B 19/2203
606/130

FOREIGN PATENT DOCUMENTS

| JP | 8-187246 | 7/1996 |
| JP | 9-136277 | 5/1997 |

* cited by examiner

*Primary Examiner* — Nicholas Kiswanto
(74) *Attorney, Agent, or Firm* — McDermott Will & Emery LLP

(57) ABSTRACT

A master motion information obtaining unit obtains at least one or more pieces of master motion information including a position, a posture, a speed, and an angular velocity of a master arm mechanism. A physical information obtaining unit obtains physical information of an operator including an arm weight of the operator. A master motion information correcting unit generates corrected master motion information where an amount of correction of the master motion information is corrected such that heavier the arm weight of the operator included in the physical information, larger a movement of a slave arm. A slave controller controls a slave arm mechanism, according to the corrected master motion information.

13 Claims, 40 Drawing Sheets

| ARM WEIGHT (kg) | AMOUNT OF CORRECTION OF MOVEMENT | |
|---|---|---|
| | MOVEMENT GAIN | CUT-OFF FREQUENCY (Hz) |
| : | : | : |
| : | : | : |
| 4.4 | 0.049 | 19.8 |
| 4.5 | 0.050 | 20.0 |
| 4.6 | 0.051 | 20.2 |
| : | : | : |
| : | : | : |

FIG. 4

| TIME (msec) | POSITION (mm) (x, y, z) | POSTURE (rad) (r_x, r_y, r_z) | SPEED (mm/msec) (v_x, v_y, v_z) | ANGULAR VELOCITY (rad/msec) ($\omega_x, \omega_y, \omega_z$) |
|---|---|---|---|---|
| .. | .. | .. | .. | .. |
| 1821 | 112.2, 65.5, −8.5 | 0.07, −0.87, 1.22 | 0.11, −0.21, 0.38 | 0.015, −0.012, 0.010 |
| 1822 | 113.1, 64.8, −8.5 | 0.06, −0.85, 1.27 | 0.95, −0.73, 0.00 | −0.018, 0.022, 0.059 |
| 1823 | 113.5, 64.0, −8.0 | 0.05, −0.82, 1.28 | 0.42, −0.82, 0.50 | −0.010, 0.026, 0.017 |
| .. | .. | .. | .. | .. |

FIG. 5A

| ARM WEIGHT (kg) | GRIP (kg) | DOMINANT ARM |
|---|---|---|
| 4.17 | — | — |

FIG. 5B

| ARM WEIGHT (kg) | GRIP (kg) | DOMINANT ARM |
|---|---|---|
| 4.17 | 45 | — |

FIG. 5C

| ARM WEIGHT (kg) | GRIP (kg) | DOMINANT ARM |
|---|---|---|
| 4.17 | — | 2 |

FIG. 5D

| ARM WEIGHT (kg) | GRIP (kg) | DOMINANT ARM |
|---|---|---|
| 4.17 | 45 | 2 |

FIG. 8

| ARM WEIGHT (kg) | AMOUNT OF CORRECTION OF MOVEMENT ||
|---|---|---|
| | MOVEMENT GAIN | CUT-OFF FREQUENCY (Hz) |
| ⋮ | ⋮ | ⋮ |
| 4.4 | 0.049 | 19.8 |
| 4.5 | 0.050 | 20.0 |
| 4.6 | 0.051 | 20.2 |
| ⋮ | ⋮ | ⋮ |

FIG. 10

| TIME (msec) | POSITION (mm) (x, y, z) | POSTURE (rad) ($r_x$, $r_y$, $r_z$) |
|---|---|---|
| ⋮ | ⋮ | ⋮ |
| 356 | 0.11, −0.21, 0.00 | 0.015, −0.012, 0.010 |
| 357 | 0.21, −0.20, 0.03 | 0.015, −0.022, 0.010 |
| 358 | 0.33, −0.21, 0.10 | 0.015, −0.026, 0.015 |
| ⋮ | ⋮ | ⋮ |

FIG. 16

| ARM WEIGHT (kg) | AMOUNT OF CORRECTION OF FORCE |
|---|---|
| | FORCE GAIN |
| ⋮ | ⋮ |
| 4.4 | 0.98 |
| 4.5 | 1.00 |
| 4.6 | 1.02 |
| ⋮ | ⋮ |

FIG. 17

| ARM WEIGHT (kg) | AMOUNT OF CORRECTION OF MOVEMENT | | AMOUNT OF CORRECTION OF FORCE |
|---|---|---|---|
| | MOVEMENT GAIN | CUT-OFF FREQUENCY (Hz) | FORCE GAIN |
| ⋮ | ⋮ | ⋮ | ⋮ |
| ⋮ | ⋮ | ⋮ | ⋮ |
| 4.4 | 0.049 | 19.8 | 0.98 |
| 4.5 | 0.050 | 20.0 | 1.00 |
| 4.6 | 0.051 | 20.2 | 1.02 |
| ⋮ | ⋮ | ⋮ | ⋮ |
| ⋮ | ⋮ | ⋮ | ⋮ |

FIG. 21

| TIME (msec) | FORCE (N OR Nm)<br>($F_x$, $F_y$, $F_z$, $M_x$, $M_y$, $M_z$) |
|---|---|
| ⋮ | ⋮ |
| 2005 | 0.55, 1.22, −2.11,<br>0.012, 0.021, 0.031 |
| 2006 | 0.57, 1.25, −2.20,<br>0.012, 0.022, 0.034 |
| 2007 | 0.55, 1.27, −2.30,<br>0.013, 0.021, 0.033 |
| ⋮ | ⋮ |

FIG. 25

| ARM WEIGHT (kg) | UPPER LIMIT (N) | LOWER LIMIT (N) |
|---|---|---|
| ⋮ | ⋮ | ⋮ |
| 4.5 | 3.48 | 0.25 |
| 4.6 | 3.52 | 0.28 |
| 4.7 | 3.65 | 0.30 |
| ⋮ | ⋮ | ⋮ |

FIG. 31
| SUPPORT INFORMATION | AMOUNT OF CORRECTION |
|---|---|
| 1 | 1 |
| 2 | 0.6 |
| 3 | 0.2 |
FIG. 32A
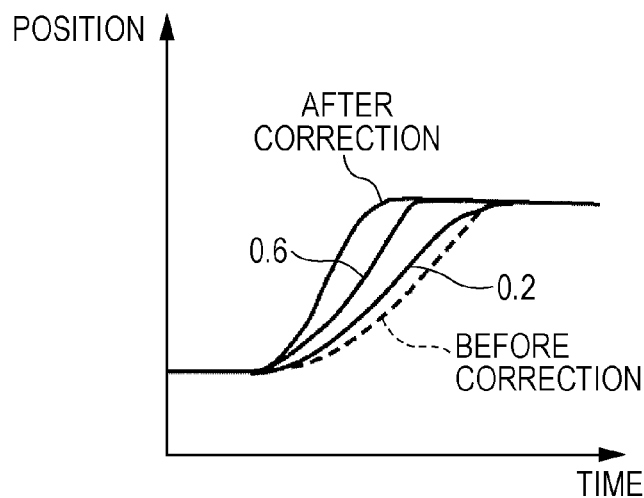
FIG. 32B
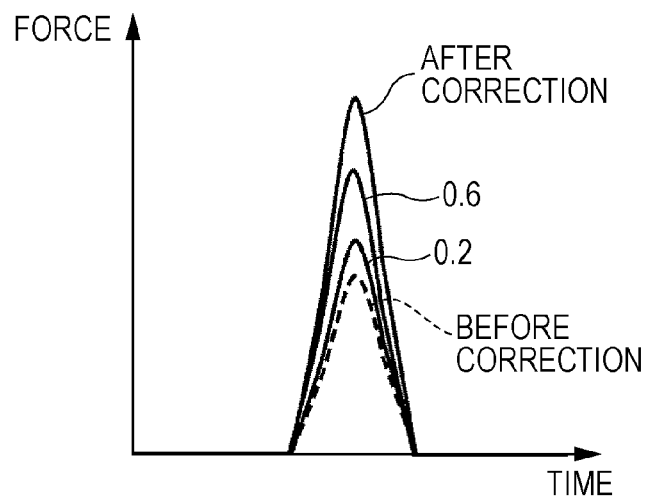

FIG. 35

| WEIGHT RATIO INFORMATION | AMOUNT OF CORRECTION |
|---|---|
| ⋮ | ⋮ |
| 1.3 | 0.96 |
| 1.4 | 0.98 |
| 1.5 | 1 |
| 1.6 | 1.02 |
| 1.7 | 1.04 |
| ⋮ | ⋮ |

FIG. 38

| POSITION (mm) (x, y, z) | POSTURE (rad) ($r_x$, $r_y$, $r_z$) |
|---|---|
| 0.08, −0.02, 0.32 | 0.005, −0.002, 0.010 |

FIG. 40

| POSITION (mm) | POSTURE (rad) | AMOUNT OF CORRECTION |
|---|---|---|
| ⋮ | ⋮ | ⋮ |
| 0.09 | 0.009 | 0.95 |
| 0.10 | 0.010 | 1 |
| 0.11 | 0.011 | 1.05 |
| ⋮ | ⋮ | ⋮ |

FIG. 42

| ENLARGEMENT FACTOR | AMOUNT OF CORRECTION OF MOVEMENT | | AMOUNT OF CORRECTION OF FORCE | |
|---|---|---|---|---|
| | FLEXIBLE MATERIAL | RIGID MATERIAL | FLEXIBLE MATERIAL | RIGID MATERIAL |
| . . | . . | . . | . . | . . |
| 0.95 | 0.98 | 1.02 | 1.02 | 0.98 |
| 1.0 | 1 | 1 | 1 | 1 |
| 1.05 | 1.02 | 0.98 | 0.98 | 1.02 |
| . . | . . | . . | . . | . . |

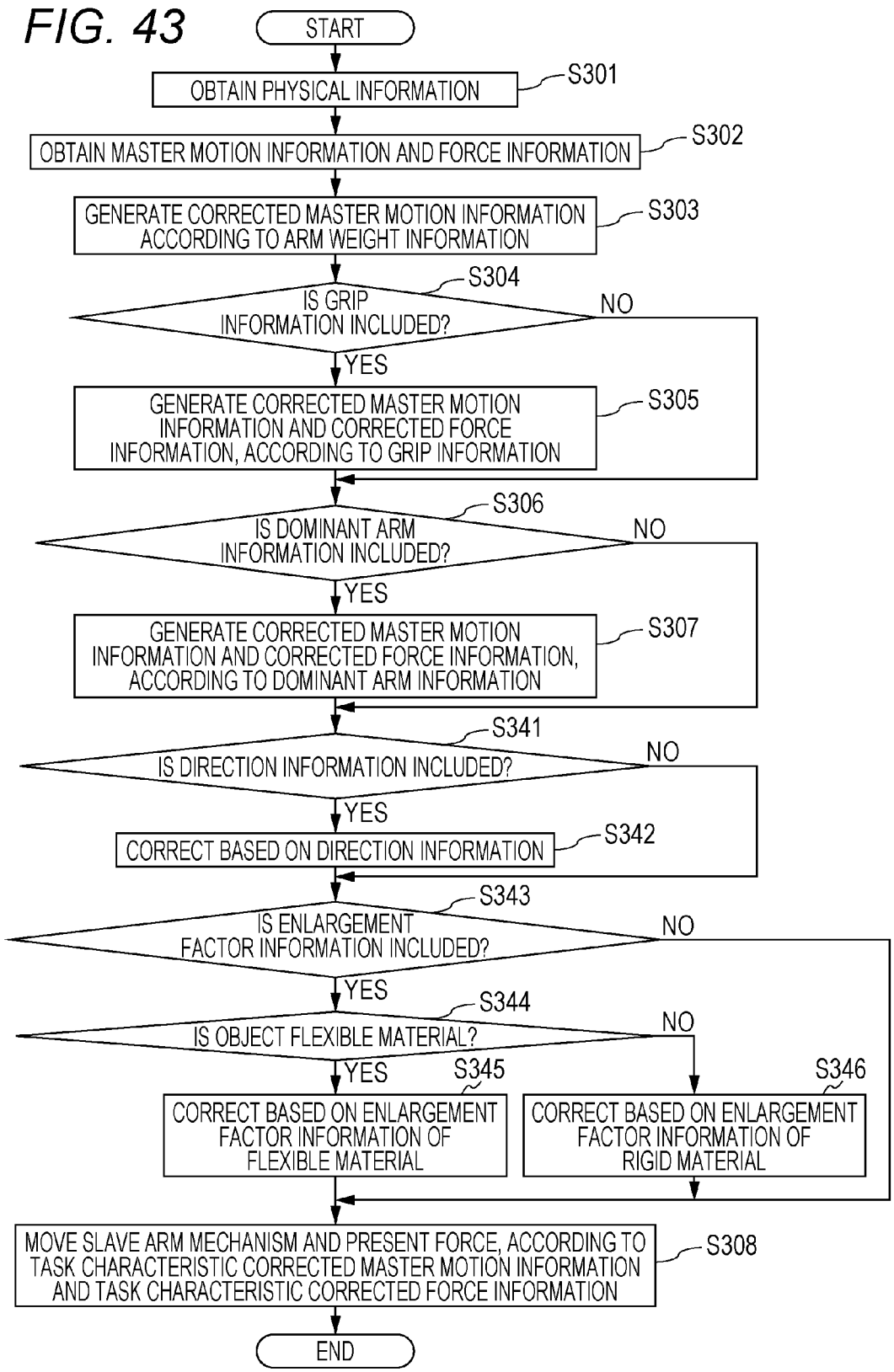

CONTROL APPARATUS AND CONTROL METHOD FOR MASTER-SLAVE ROBOT, MASTER-SLAVE ROBOT, CONTROL PROGRAM FOR MASTER-SLAVE ROBOT, AND INTEGRATED ELECTRONIC CIRCUIT FOR CONTROLLING MASTER-SLAVE ROBOT

BACKGROUND

1. Technical Field

The present disclosure relates to a control apparatus and a control method for a master-slave robot for generating motions of the master-slave robot, a master-slave robot, a control program for a master-slave robot, and an integrated electronic circuit for controlling a master-slave robot.

2. Description of the Related Art

A master-slave robot in which a person remotely manipulates a master robot to allow a slave robot to perform tasks is attracting attention in various fields.

In the medical field, there is endoscopic surgery where a surgeon performs surgery by remotely manipulating a master robot while watching endoscopic video displayed on a monitor screen, to move forceps gripped by a slave robot. In addition to an advantage in that the surgery can be performed such that an affected area, the forceps, or the like, is enlarged and displayed on the monitor screen, even if there are no specialist doctors in the scene, remote surgery can be performed.

In addition, in the manufacturing field, there is proposed a master-slave robot that remotely manipulates or teaches a slave robot which performs a fine task, an enlargement task, or a task required skills. In particular, for a fine task performed under a microscope, a fine task can be easily manipulated by, for example, an enlarged display of hands, an increase in an amount of movement of a hand manipulation, or a reduction movement.

All master-slave schemes require a function of manipulating a master robot to smoothly manipulate a slave robot without hand shaking. In addition, the master-slave schemes require a function of feeding back a force applied to the slave robot, to the master robot.

Meanwhile, there are proposed techniques in which a master-slave manipulator automatically adjusts a motion ratio between a master robot and a slave robot, according to an enlargement factor of video displayed on a monitor (see Patent Literatures 1 and 2).

CITATION LIST

Patent Literatures

PTL 1: Unexamined Japanese Patent Publication No. 8-187246

PTL 2: Unexamined Japanese Patent Publication No. 9-136277

SUMMARY

In a case of a change of operators, there is a need to handle variations in task efficiency or quality.

An object of the present disclosure is therefore to solve the above-described problem, and to provide a control apparatus and a control method for a master-slave robot which is manipulated by an operator and which is capable of performing a uniform task even in a case of different operators, a master-slave robot, a control program for a master-slave robot, and an integrated electronic circuit for controlling a master-slave robot.

The present disclosure is directed to a master-slave robot comprising:

a slave arm that performs a task using a slave arm mechanism;

a master arm that has a master arm mechanism and that is remotely manipulated by an operator to allow the slave arm mechanism to make a motion: and control circuitry configured to:

obtain master motion information including at least one selected from the group consisting of a position, a posture, a speed, and an angular velocity of the master arm mechanism;

obtain physical information including an arm weight of the operator;

correct the master motion information based the physical information in such a manner that the heavier the arm weight of the operator included in the physical information is, the larger the slave arm moves; and control the slave arm mechanism, according to the corrected master motion information.

These general and specific aspects may be implemented as a system, a method, a computer program, and any combination of a system, a method, and a computer program.

According to the above-described aspect of the present disclosure, the slave arm mechanism can make motions according to physical information of an operator. Thus, even in a case of different operators, a uniform task can be performed.

BRIEF DESCRIPTION OF DRAWINGS

FIG. 4 is a data diagram of an example of motion information and time information in the master-slave robot of the first embodiment of the present disclosure;

FIG. 5A is a data diagram of an example of physical information in the master-slave robot of the first embodiment of the present disclosure;

FIG. 5B is a data diagram of an example of physical information in the master-slave robot of the first embodiment of the present disclosure;

FIG. 5C is a data diagram of an example of physical information in the master-slave robot of the first embodiment of the present disclosure;

FIG. 5D is a data diagram of an example of physical information in the master-slave robot of the first embodiment of the present disclosure;

FIG. 8 is a data diagram of an example of arm weights and amounts of correction of movement in the master-slave robot of the first embodiment of the present disclosure;

FIG. 10 is a data diagram of an example of corrected master motion information and time information in the master-slave robot of the first embodiment of the present disclosure;

FIG. 16 is a data diagram of an example of arm weights and amounts of correction of force in the master-slave robot of the second embodiment of the present disclosure;

FIG. 17 is a data diagram of an example of arm weights, amounts of correction of movement, and amounts of correction of force in the master-slave robot of the second embodiment of the present disclosure;

FIG. 21 is a data diagram of an example of force information and time information in the master-slave robot of the second embodiment of the present disclosure;

FIG. 25 is a data diagram of an example of force range information in the master-slave robot of the third embodiment of the present disclosure;

FIG. 31 is an illustrative diagram of an example of fixing methods and amounts of correction in the master-slave robot of the fourth embodiment of the present disclosure;

FIG. 32A is an illustrative diagram of support portion corrected force information in the master-slave robot of the fourth embodiment of the present disclosure;

FIG. 32B is an illustrative diagram of support portion corrected force information in the master-slave robot of the fourth embodiment of the present disclosure;

FIG. 35 is an illustrative diagram of an example of weight ratio information and amounts of correction in the master-slave robot of the fifth embodiment of the present disclosure;

FIG. 38 is a data diagram of an example of direction information in the master-slave robot of the sixth embodiment of the present disclosure;

FIG. 40 is an illustrative diagram of an example of of direction information and amounts of correction in the master-slave robot of the sixth embodiment of the present disclosure;

FIG. 42 is an illustrative diagram of an example of enlargement factor information and amounts of correction in the master-slave robot of the sixth embodiment of the present disclosure; and FIG. 43 is a flowchart of a correction procedure of the master-slave robot of the sixth embodiment of the present disclosure.

DETAILED DESCRIPTION OF THE EMBODIMENTS

Embodiments of the present disclosure will be described in detail below with reference to the drawings.

Prior to describing the embodiments of the present disclosure in detail below with reference to the drawings, first, findings which are the basis for the present disclosure will be described and then various modes of the present disclosure will be described.

(Findings which are the Basis for the Present Disclosure)

Figure 1:
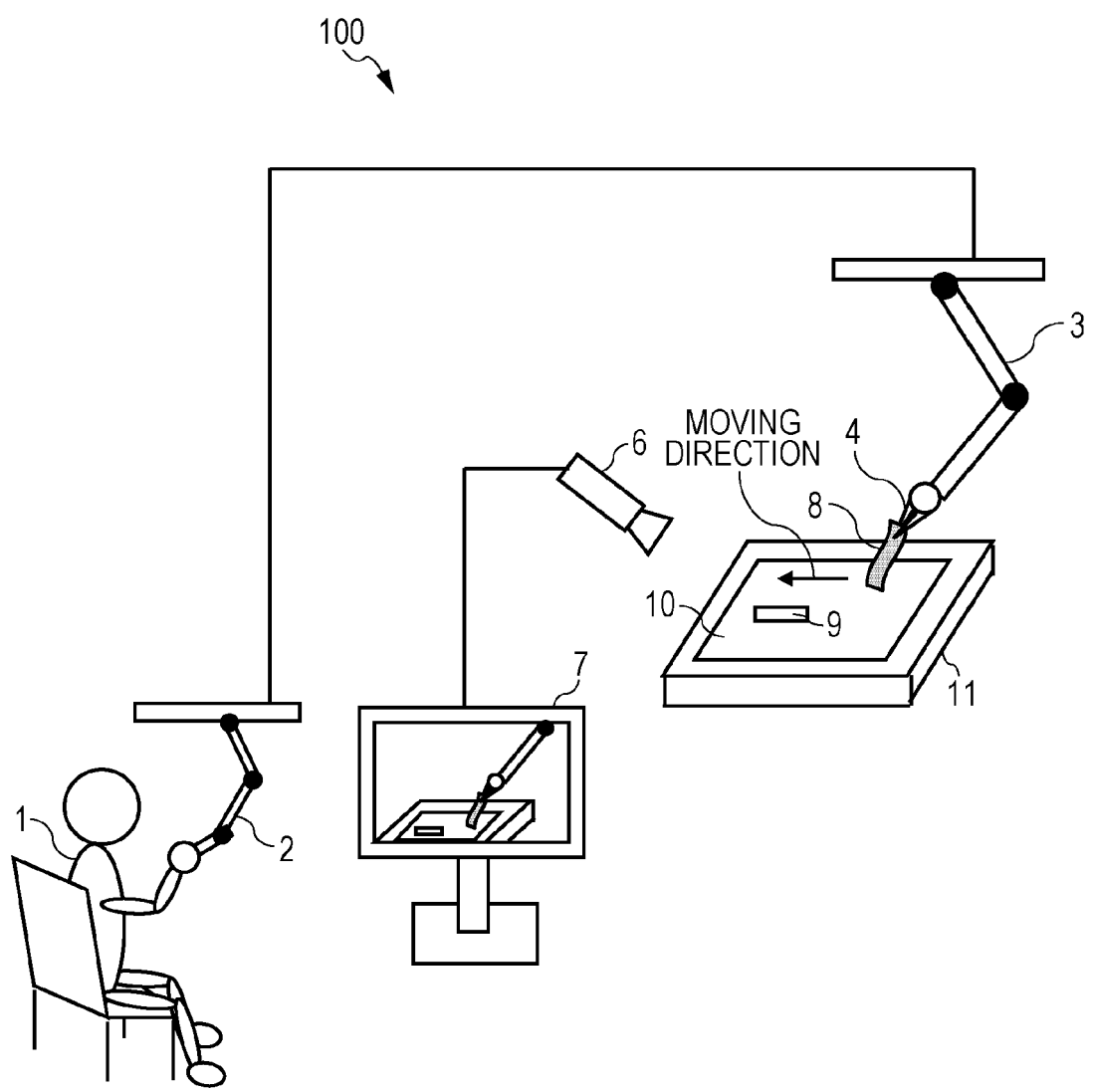
FIG. 1 is a diagram showing a summary of a configuration of a master-slave robot of a first embodiment of the present disclosure.

As shown in FIG. 1, slave arm 3 is a robot that performs a task of inserting fine part 8 gripped by hand 4 into insertion opening 9 of device 10 on workbench 11. Video of the task is captured by imaging apparatus 6, such as a camera, and displayed on display 7. FIG. 1 shows master-slave robot 100 in which, in the above-described circumstances, operator (person) 1 manipulates master arm 2 while watching the video displayed on display 7. In this master-slave robot 100, when an enlargement factor of video or a motion ratio of slave arm 3 to master arm 2 is changed, a correspondence between video watched so far and a manipulation of master arm 2 or how a force is felt changes, changing task efficiency or quality.

Figure 2A:
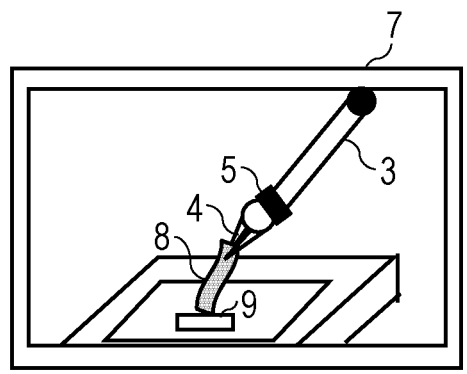
FIG. 2A is an illustrative diagram of video and how a force is felt in a conventional master-slave robot.
Figure 2B:
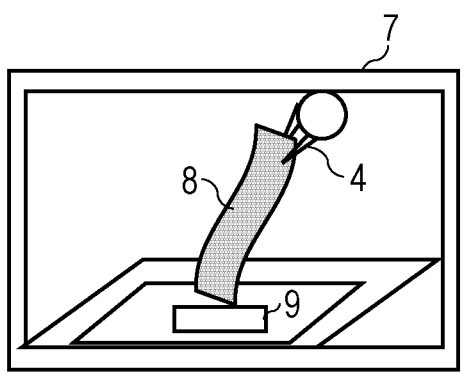
FIG. 2B is an illustrative diagram of video and how a force is felt in the conventional master-slave robot.

A specific description will be given with reference to FIGS. 2A and 2B. FIGS. 2A and 2B show video on a screen of display 7 watched by operator 1 in master-slave robot 100 shown in FIG. 1. An enlargement factor of video is greater in FIG. 2B than in FIG. 2A and objects on the screen such as fine part 8 are displayed larger than actual size. As such, with a greater enlargement factor, a degree of bending of fine part 8 on the screen looks greater to operator 1. Thus, operator 1 performs a task with a smaller force than a force actually required for the task. As a result, operator 1 cannot apply a force required for the task to master arm 2, making it difficult to perform the task in the same manner as in FIG. 2A. In view of this, there is proposed a technique for associating video watched by operator 1 with a manipulation performed by operator 1.

Specifically, in methods of Patent Literatures 1 and 2, a motion ratio of slave arm 3 to master arm 2 is automatically adjusted according to an enlargement factor of video displayed on display 7. For example, when the enlargement factor is kx, the motion ratio is set to 1/k.

In the methods of Patent Literatures 1 and 2, however, although the motion ratio is changed according to the enlargement factor of video, the methods do not support a case of a change of operators. That is, neither of Patent Literatures 1 nor 2 considers achieving uniform task quality and efficiency when different operators perform tasks. Patent Literatures 1 and 2 fail to handle variations in task quality (force to be applied) and variations in task efficiency (task time) between operators.

Thus, in order that master-slave robot 100 can maintain uniform task efficiency and quality even when various operators perform manipulations, master-slave robot 100 is required to be controlled to automatically adjust an amount of movement made by a motion of slave arm 3 or a force-feedback force, according to physical characteristics of operator 1.

In view of this, according to a first aspect of the present disclosure, there is provided a control apparatus for a master-slave robot including a slave arm that performs a task using a slave arm mechanism; and a master arm that has a master arm mechanism and that is remotely manipulated by an operator to allow the slave arm mechanism to make a motion, the control apparatus including:

a master motion information obtaining unit that obtains at least one or more pieces of master motion information including a position, a posture, a speed, and an angular velocity of the master arm mechanism;

a physical information obtaining unit that obtains physical information of the operator, the physical information including an arm weight of the operator;

a master motion information correcting unit that generates corrected master motion information where an amount of correction of the master motion information obtained from the master motion information obtaining unit is corrected such that heavier the arm weight of the operator included in the physical information, larger a movement of the slave arm, the physical information being obtained from the physical information obtaining unit; and a slave controller that controls the slave arm mechanism, according to the corrected master motion information obtained from the master motion information correcting unit.

Thus, master motion information which is used to move the slave arm mechanism can be corrected based on physical information. That is, the master arm mechanism can be manipulated such that even if a person, i.e., an operator, is changed, a task can be performed with uniform quality and efficiency.

In addition, according to a second aspect of the present disclosure, there is provided the control apparatus for a master-slave robot described in the first aspect that further includes:

a force information obtaining unit that obtains force information externally applied to the slave arm mechanism when the slave arm mechanism makes a motion under control of the slave controller;

a force information correcting unit that generates corrected force information where the force information obtained from the force information obtaining unit is corrected such that heavier the arm weight of the operator included in the physical information, larger the force information, the physical information being obtained from the physical information obtaining unit; and a force information presenting unit that presents the corrected force information generated by the force information correcting unit, to the maser arm mechanism.

Thus, force information which is used to perform a force presentation can be corrected based on physical information. That is, a force can be presented to an operator through the master arm mechanism such that even if the operator is changed, a task can be performed with uniform quality and efficiency.

In addition, according to a third aspect of the present disclosure, there is provided the control apparatus for a master-slave robot described in the second aspect that further includes:

a force range information generator that generates force range information, based on the physical information obtained from the physical information obtaining unit, the force range information being information on an upper limit and a lower limit of the force information; and a force information range correcting unit that generates range-corrected force information where the corrected force information obtained from the force information correcting unit is corrected to fall within a range of the force range information obtained from the force range information generator, and outputs the range-corrected force information to the force information presenting unit, wherein the force information presenting unit presents the range-corrected force information obtained from the force information range correcting unit, to the slave arm mechanism.

Thus, a force correction using an upper limit and a lower limit set for each physical information of an operator is made, and then a force is presented to the operator through the master arm mechanism. Thus, the operator can perform a task with a force presentation in a range where the operator can easily perform the task. As a result, even in a case of different operators, efficient tasks can be performed.

In addition, according to a fourth aspect of the present disclosure, there is provided the control apparatus for a master-slave robot described in the first aspect that further includes:

a support information obtaining unit that obtains support information, the support information being information on a support portion that supports an arm of the operator when the operator manipulates the master arm; and a support portion correcting unit that generates, based on the support information, support portion corrected master motion information by changing the amount of correction of the master motion information based on the master motion information and the corrected master motion information such that closer a position of the support portion to a hand of the operator manipulating the master arm, smaller the amount of correction of the master motion information, and outputs the support portion corrected master motion information to the slave controller, the support information being obtained from the support information obtaining unit, the master motion information and the corrected master motion information being obtained from the master motion information correcting unit, wherein the slave controller controls the slave arm mechanism, according to the support portion corrected master motion information obtained from the support portion correcting unit.

In addition, according to a fifth aspect of the present disclosure, there is provided the control apparatus for a master-slave robot described in the second aspect that further includes:

a support information obtaining unit that obtains support information, the support information being information on a support portion that supports an arm of the operator when the operator manipulates the master arm; and a support portion correcting unit that generates, based on the support information, support portion corrected master motion information or support portion corrected force information by changing the amount of correction of the master motion information based on the master motion information and the corrected master motion information or based on the force information and the corrected force information such that closer a position of the support portion to a hand of the operator manipulating the master arm, smaller the amount of correction of the master motion information, and outputs the support portion corrected master motion information or the support portion corrected force information to the slave controller or the force information presenting unit, the support information being obtained from the support information obtaining unit, the master motion information and the corrected master motion information being obtained from the master motion information correcting unit, the force information and the corrected force information being obtained from the force information correcting unit, wherein when the support portion correcting unit generates the support portion corrected master motion information based on the support portion information and outputs the support portion corrected master motion information to the slave controller, the slave controller controls the slave arm mechanism, according to the support portion corrected master motion information obtained from the support portion correcting unit, and wherein when the support portion correcting unit generates the support portion corrected force information based on the support portion information and outputs the support portion corrected force information to the force information presenting unit, the force information presenting unit presents the support portion corrected force information obtained from the support portion correcting unit, to the slave arm mechanism.

Thus, master motion information or force information is corrected based on a method of fixing (supporting) an arm of an operator, and then a task or a force presentation is performed. Thus, even in a case of different postures of the operator upon manipulations, variations in quality and efficiency can be overcome.

In addition, according to a sixth aspect of the present disclosure, there is provided the control apparatus for a master-slave robot described in the first aspect that further includes:

a master weight information obtaining unit that obtains weight information of the master arm;

an arm weight information obtaining unit that obtains arm weight information of the operator from the physical information obtained from the physical information obtaining unit; and a weight ratio correcting unit that calculates a ratio of the arm weight information to the master arm weight information based on the master arm weight information obtained from the master arm weight information obtaining unit and based on the arm weight information obtained from the arm weight information obtaining unit, and generates weight ratio corrected master motion information by changing an amount of correction based on the master motion information and the corrected master motion information such that larger the ratio, larger the amount of correction, and outputs the weight ratio corrected master motion information to the slave controller, the master motion information and the corrected master motion information being obtained from the master motion information correcting unit, wherein the slave controller controls the slave arm mechanism, according to the weight ratio corrected master motion information obtained from the weight ratio correcting unit.

In addition, according to a seventh aspect of the present disclosure, there is provided the control apparatus for a master-slave robot described in the second aspect that further includes:

a master weight information obtaining unit that obtains weight information of the master arm;

an arm weight information obtaining unit that obtains arm weight information of the operator from the physical information obtained from the physical information obtaining unit; and a weight ratio correcting unit that calculates a ratio of the arm weight information to the master arm weight information based on the master arm weight information obtained from the master arm weight information obtaining unit and based on the arm weight information obtained from the arm weight information obtaining unit, and generates weight ratio corrected master motion information or weight ratio corrected force information by changing an amount of correction based on the master motion information and the corrected master motion information or based on the force information and the corrected force information such that larger the ratio, larger the amount of correction, and outputs the weight ratio corrected master motion information or the weight ratio corrected force information to the slave controller or the force information presenting unit, the master motion information and the corrected master motion information being obtained from the master motion information correcting unit, the force information and the corrected force information being obtained from the force information correcting unit, wherein when the weight ratio correcting unit generates the weight ratio corrected master motion information based on the master arm weight information and the arm weight information and outputs the weight ratio corrected master motion information to the slave controller, the slave controller controls the slave arm mechanism, according to the weight ratio corrected master motion information obtained from the weight ratio correcting unit, and wherein when the weight ratio correcting unit generates the weight ratio corrected force information based on the master arm weight information and the arm weight information and outputs the weight ratio corrected force information to the force information presenting unit, the force information presenting unit presents the weight ratio corrected force information obtained from the weight ratio correcting unit, to the slave arm mechanism.

Thus, master motion information or force information is corrected based on a weight of an arm of an operator and further on a weight of the master arm mechanism, and then a task or a force presentation is performed. Thus, even in a case of different master arm mechanisms manipulated by the operator, variations in quality and efficiency can be overcome.

In addition, according to an eighth aspect of the present disclosure, there is provided the control apparatus for a master-slave robot described in the first aspect, wherein the physical information obtained by the physical information obtaining unit is grip information or dominant arm information in addition to arm weight information of the operator, and wherein large dominant arm information indicates that the operator manipulates the master arm mechanism by his/her dominant arm.

Thus, master motion information which is used to move the slave arm mechanism can be corrected based on grip information or dominant arm information in addition to arm weight information of a person, i.e., an operator. That is, the master arm mechanism can be manipulated such that even if the operator is changed, a task can be performed with uniform quality and efficiency.

In addition, according to a ninth aspect of the present disclosure, there is provided the control apparatus for a master-slave robot described in the first aspect, wherein the correction made by the master motion information correcting unit to allow the slave arm to move a large amount is one or more corrections including increasing a movement gain and increasing a cut-off frequency of a low-pass filter.

Thus, master motion information which is used to move the slave arm mechanism can be corrected using a movement gain or a cut-off frequency. As a result, an accurate correction can be made, and even in a case of different operators, the operators can perform precise tasks.

In addition, according to a tenth aspect of the present disclosure, there is provided the control apparatus for a master-slave robot described in the first aspect that further includes:

a task characteristic information obtaining unit that obtains task characteristic information of the operator; and a task characteristic correcting unit that generates task characteristic corrected master motion information by further correcting, based on the task characteristic information, the corrected master motion information obtained from the master motion information correcting unit, and outputs the task characteristic corrected master motion information to the slave controller, the task characteristic information being obtained by the task characteristic information obtaining unit, wherein the slave controller controls the slave arm mechanism, according to the task characteristic corrected master motion information obtained from the task characteristic correcting unit.

In addition, according to an eleventh aspect of the present disclosure, there is provided the control apparatus for a master-slave robot described in the second aspect that further includes:

a task characteristic information obtaining unit that obtains task characteristic information of the operator; and a task characteristic correcting unit that generates task characteristic corrected master motion information or task characteristic corrected force information by further correcting, based on the task characteristic information, the corrected master motion information obtained from the master motion information correcting unit or the corrected force information obtained from the force information correcting unit, and outputs the task characteristic corrected master motion information or the task characteristic corrected force information to the slave controller or the force information presenting unit, the task characteristic information being obtained by the task characteristic information obtaining unit, wherein when the task characteristic correcting unit generates the task characteristic corrected master motion information based on the task characteristic information and outputs the task characteristic corrected master motion information to the slave controller, the slave controller controls the slave arm mechanism, according to the task characteristic corrected master motion information obtained from the task characteristic correcting unit, and wherein when the task characteristic correcting unit generates the task characteristic corrected force information based on the task characteristic information and outputs the task characteristic corrected force information to the force information presenting unit, the force information presenting unit presents the task characteristic corrected force information obtained from the task characteristic correcting unit, to the slave arm mechanism.

Thus, master motion information or force information is corrected based on a task characteristic, and then a task or a force presentation is performed. Thus, even in a case of different conditions where a task is performed, variations in quality and efficiency can be overcome.

In addition, according to a twelfth aspect of the present disclosure, there is provided the control apparatus for a master-slave robot described in the tenth aspect, wherein the task characteristic information obtained from the task characteristic information obtaining unit is direction information in which the operator performs the task, and wherein the task characteristic correcting unit makes a correction such that a direction in which the master arm mechanism moves a larger amount has a larger amount of correction of the task characteristic corrected master motion information or task characteristic corrected force information. Thus, master motion information or force information is corrected based on direction information, and then a task or a force presentation is performed. Thus, even in a case of different directions in which a task is performed, variations in quality and efficiency can be overcome.

In addition, according to a thirteenth aspect of the present disclosure, there is provided the control apparatus for a master-slave robot described in the tenth aspect, wherein the task characteristic information obtained from the task characteristic information obtaining unit is enlargement factor information of an imaging apparatus that captures video of the task performed by the slave arm mechanism, and wherein when an object for the task is a flexible material, the task characteristic correcting unit makes a correction such that larger the enlargement factor information, larger the amount of correction of the corrected master motion information, and when the object is a rigid material, the task characteristic correcting unit makes a correction such that larger the enlargement factor information, smaller the amount of correction of the corrected master motion information.

According to a fourteenth aspect of the present disclosure, there is provided the control apparatus for a master-slave robot described in the eleventh aspect, wherein the task characteristic information obtained from the task characteristic information obtaining unit is enlargement factor information of an imaging apparatus that captures video of the task performed by the slave arm mechanism, and wherein when an object for the task is a flexible material, the task characteristic correcting unit makes a correction such that larger the enlargement factor information, larger the amount of correction of the corrected master motion information or smaller an amount of correction of the corrected force information, and when the object is a rigid material, the task characteristic correcting unit makes a correction such that larger the enlargement factor information, smaller the amount of correction of the corrected master motion information or larger the amount of correction of the corrected force information.

Thus, master motion information or force information is corrected based on enlargement factor information of the imaging apparatus, and then a task or a force presentation is performed. Thus, even in a case of different enlargement factors used when a task is performed, variations in quality and efficiency can be overcome.

According to a fifteenth aspect of the present disclosure, there is provided a master-slave robot including:

the control apparatus for a master-slave robot described in the first aspect;

the slave arm having the slave arm mechanism; and the master arm having the master arm mechanism and allowing the slave arm mechanism to make a motion.

According to a sixteenth aspect of the present disclosure, there is provided a control method for a master-slave robot including a slave arm that performs a task using a slave arm mechanism; and a master arm that has a master arm mechanism and that is remotely manipulated by an operator to allow the slave arm mechanism to make a motion, the control method including:

obtaining, by master motion information obtaining unit, at least one or more pieces of master motion information including a position, a posture, a speed, and an angular velocity of the master arm mechanism;

obtaining, by a physical information obtaining unit, physical information of the operator, the physical information including an arm weight of the operator;

generating, by a master motion information correcting unit, corrected master motion information where an amount of correction of the master motion information obtained from the master motion information obtaining unit is corrected such that heavier the arm weight of the operator included in the physical information, larger a movement of the slave arm, the physical information being obtained from the physical information obtaining unit; and controlling, by a slave controller, the slave arm mechanism, according to the corrected master motion information obtained from the master motion information correcting unit.

According to a seventeenth aspect of the present disclosure, there is provided a control program for a master-slave robot including a slave arm that performs a task using a slave arm mechanism; and a master arm that has a master arm mechanism and that is remotely manipulated by an operator to allow the slave arm mechanism to make a motion, the control program causing a computer to function as:

a master motion information obtaining unit that obtains at least one or more pieces of master motion information including a position, a posture, a speed, and an angular velocity of the master arm mechanism;

a physical information obtaining unit that obtains physical information of the operator, the physical information including an arm weight of the operator;

a master motion information correcting unit that generates corrected master motion information where an amount of correction of the master motion information obtained from the master motion information obtaining unit is corrected such that heavier the arm weight of the operator included in the physical information, larger a movement of the slave arm, the physical information being obtained from the physical information obtaining unit; and a slave controller that controls the slave arm mechanism, according to the corrected master motion information obtained from the master motion information correcting unit.

According to an eighteenth aspect of the present disclosure, there is provided an integrated electronic circuit for controlling a master-slave robot including a slave arm that performs a task using a slave arm mechanism; and a master arm that has a master arm mechanism and that is remotely manipulated by an operator to allow the slave arm mechanism to make a motion, the integrated electronic circuit including:

a master motion information obtaining unit that obtains at least one or more pieces of master motion information including a position, a posture, a speed, and an angular velocity of the master arm mechanism;

a physical information obtaining unit that obtains physical information of the operator, the physical information including an arm weight of the operator;

a master motion information correcting unit that generates corrected master motion information where an amount of correction of the master motion information obtained from the master motion information obtaining unit is corrected such that heavier the arm weight of the operator included in the physical information, larger a movement of the slave arm, the physical information being obtained from the physical information obtaining unit; and a slave controller that controls the slave arm mechanism, according to the corrected master motion information obtained from the master motion information correcting unit.

According to a nineteenth aspect of the present disclosure, there is provided a control apparatus for a master-slave robot including a slave arm that performs a task using a slave arm mechanism; and a master arm that has a master arm mechanism and that is remotely manipulated by an operator to allow the slave arm mechanism to make a motion, the control apparatus including:

a master motion information obtaining unit that obtains at least one or more pieces of master motion information including a position, a posture, a speed, and an angular velocity of the master arm mechanism;

a physical information obtaining unit that obtains physical information of the operator, the physical information including an arm weight of the operator;

a corrected information generator that generates corrected information, according to the arm weight of the operator included in the physical information, the physical information being obtained from the physical information obtaining unit; and a controller that controls the master arm mechanism or the slave arm mechanism, according to the corrected information obtained from the corrected information generator.

According to the configurations of the fifteenth to nineteenth aspects, master motion information which is used to move the slave arm mechanism can be corrected based on physical information. That is, the master arm mechanism can be manipulated such that even if a person, i.e., an operator, is changed, a task can be performed with uniform quality and efficiency.

First Embodiment

A description will be given of a summary of master-slave robot 100 including control apparatus 101 for master-slave robot 100 of a first embodiment of the present disclosure.

FIG. 1 shows a state of a task of moving fine part 8 using master-slave robot 100.

A description will be given of an example of a task of contactlessly moving fine part 8 in a direction of connector's insertion opening 9 of a printed circuit board for device 10, such as a television, a DVD recorder, or a mobile phone, in cell production in a factory, for example, as shown in FIG. 1.

Slave arm 3 of master-slave robot 100 is a robot that is placed above workbench 11 where device 10 is placed, or on a wall surface, and that performs a task of moving fine part 8 in the direction of insertion opening 9 of device 10.

Hand 4 that grips fine part 8 is attached to an end of slave arm 3.

Imaging apparatus 6 such as a camera is disposed on workbench 11. Imaging apparatus 6 captures video of hand 4, fine part 8, and insertion opening 9 in an enlarged manner, and displays the captured video on display 7.

By operator 1 manipulating master arm 2 while checking, on display 7, the video which is captured by imaging apparatus 6, slave arm 3 makes motions. Master-slave robot 100 of the first embodiment is a robot that does not perform feedback of a force. Thus, even if slave arm 3 comes into contact during a task, operator 1 manipulating master arm 2 cannot feel a force. However, operator 1 can estimate a magnitude of a force occurring in slave arm 3 from, for example, a degree of bending and a degree of deformation of fine part 8 displayed on display 7.

Figure 3:
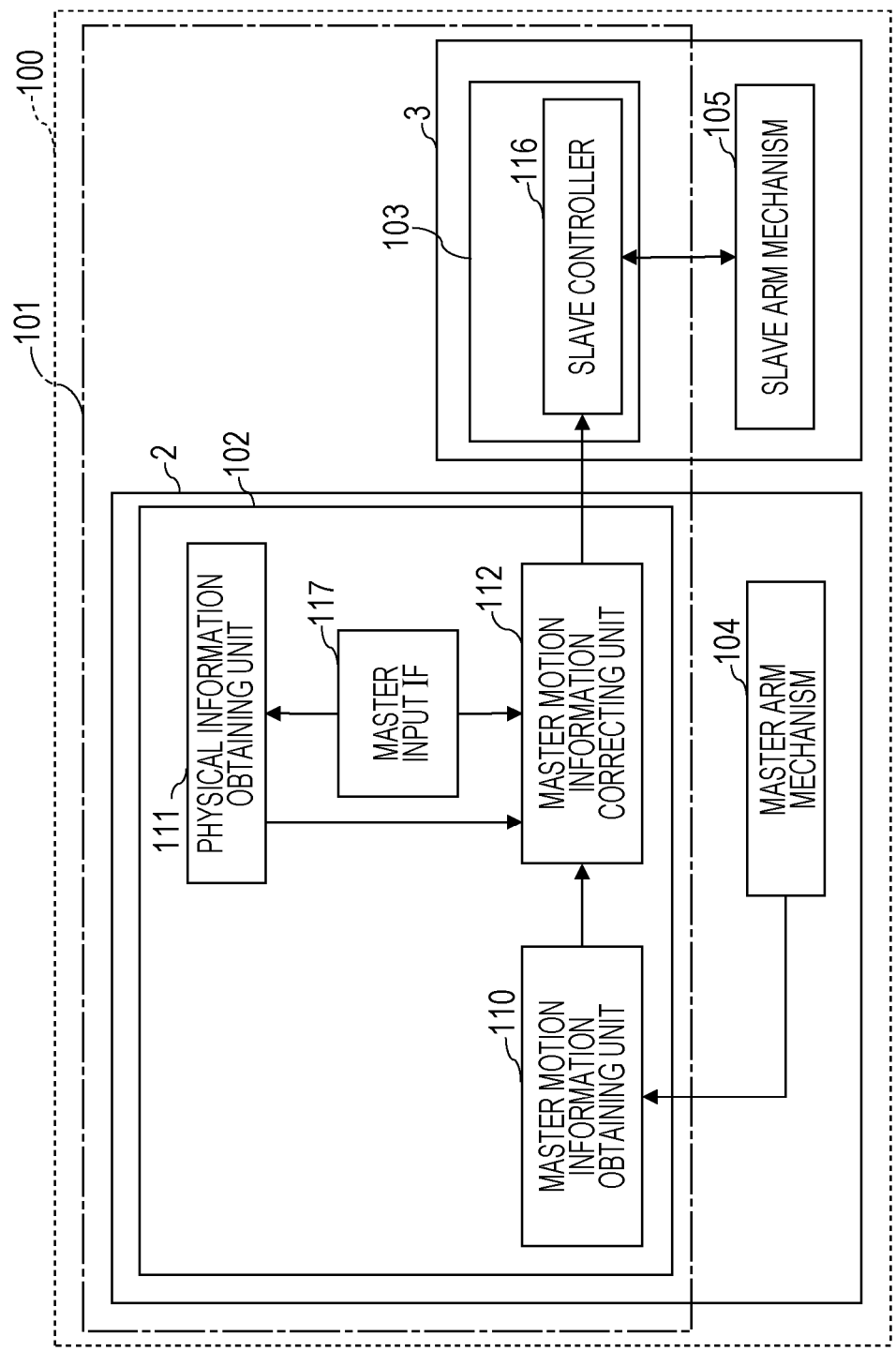
FIG. 3 is a block diagram of the master-slave robot of the first embodiment of the present disclosure.

FIG. 3 is a block diagram of master-slave robot 100 of the first embodiment of the present disclosure. In FIG. 3, master-slave robot 100 includes master arm 2 and slave arm 3. Master arm 2 includes control apparatus 102 for master arm 2; and master arm mechanism 104. Slave arm 3 includes control apparatus 103 for slave arm 3; and slave arm mechanism 105.

Control apparatus 102 for master arm 2 is a control apparatus for master arm 2 that generates motions of slave arm mechanism 105. Control apparatus 103 for slave arm 3 is a control apparatus for slave arm 3 that controls a position and a posture of slave arm mechanism 105.

The first embodiment will be described in detail below.

<Description of the Control Apparatus for the Master Arm>

Control apparatus 102 for master arm 2 includes master motion information obtaining unit 110, physical information obtaining unit 111, master motion information correcting unit 112, and master input IF 117.

(Master Motion Information Obtaining Unit 110)

Computing units included in encoders for respective rotating (drive) shafts of master arm mechanism 104 obtain position information and posture information of master arm mechanism 104 from values which are input from the encoders. Master motion information obtaining unit 110 obtains, as master motion information, the position information, the posture information, and time information obtained from a timer included in master motion information obtaining unit 110. In addition, master motion information obtaining unit 110 obtains speed information by differentiating the obtained position information with respect to the time information. In addition, master motion information obtaining unit 110 obtains angular velocity information by differentiating the posture information with respect to the time information. FIG. 4 shows time information, position information, posture information, speed information, and angular velocity information which are obtained by master motion information obtaining unit 110.

Mater motion information (master motion information) of master arm mechanism 104 includes these position information, posture information, speed information, and angular velocity information form.

Master motion information obtaining unit 110 outputs the obtained position information, posture information, speed information, angular velocity information, and time information of master arm mechanism 104 to master motion information correcting unit 112.

(Physical Information Obtaining Unit 111)

Physical information is input to physical information obtaining unit 111 from master input IF 117.

The physical information is information indicating physical characteristics of operator 1. The physical information includes arm weight information, grip information, and dominant arm information. The physical information always includes at least arm weight information and arbitrarily includes other information.

Methods of calculating arm weight information of operator 1 include, for example, a method of detecting (calculating) arm weight information by measuring a weight of an arm ranging from a tip of a hand to a base of an arm of operator 1, using a scale, and a method of calculating arm weight information by measuring a weight of operator 1 and calculating a value of 6.5% of the weight because 6.5% of the weight is supposed to be a weight of an upper limb. In addition, there is a method of calculating arm weight information by measuring inertia. A reason that arm weight information is thus required is because in the present disclosure it is premised that operator 1 performs a task sitting on a chair. In such a case, an arm weight affects accuracy of the task.

Note that instead of arm weight information, it is also possible to use arm and master arm weight information. An arm weight of operator 1 is measured in the same manner as the above-described methods. For weight information of master arm mechanism 104, weight information provided by a manufacturer is used, or the weight information of master arm mechanism 104 is calculated by measuring inertia. A value obtained by adding together the thus measured arm weight information of operator 1 and weight information of master arm mechanism 104 is used as arm and master arm weight information. Use of the arm and master arm weight information also makes it possible to handle a case of different master arms in addition to a case of different operators 1.

In addition, instead of arm weight information, it is also possible to use amount-of-arm-muscle-strength information. An amount of muscle strength is measured using a myoelectric sensor or the like. Use of the amount-of-arm-muscle-strength information in this manner also makes it possible to handle a case of different muscle strengths.

The grip information is obtained by measuring grip. The dominant arm information indicates whether an arm of operator 1 used when operator 1 manipulates master arm mechanism 104 is his/her dominant arm.

The thus calculated information is directly output to master input IF 117 or is input by operator 1 using master input IF 117, for example. Thus, physical information obtaining unit 111 obtains physical information through master input IF 117.

FIGS. 5A to 5D show examples of physical information. FIG. 5A shows a case in which physical information includes only arm weight information. FIG. 5B shows a case in which physical information includes arm weight information and grip information. FIG. 5C shows a case in which physical information includes arm weight information and dominant arm information. FIG. 5D shows a case in which physical information includes arm weight information, grip information, and dominant arm information.

When an arm of operator 1 manipulating master arm mechanism 104 is his/her dominant arm, the dominant arm information indicates "2". When the arm is not his/her dominant arm, the dominant arm information indicates "1".

Physical information obtaining unit 111 outputs the physical information obtained by master input IF 117, to master motion information correcting unit 112.

(Master Motion Information Correcting Unit 112)

Motion information (i.e., master motion information) and time information of master arm mechanism 104 are input to master motion information correcting unit 112 from master motion information obtaining unit 110. Physical information is input to master motion information correcting unit 112 from physical information obtaining unit 111. Based on the obtained motion information of master arm mechanism 104, master motion information correcting unit 112 calculates an amount of movement of hand 4 caused by master arm mechanism 104 for each sampling cycle. Master motion information correcting unit 112 applies a gain or a filter calculated from the physical information to the calculated amount of movement, and outputs the resulting amount as corrected master motion information (amount-of-movement instruction value) to slave controller 116.

Figure 6:
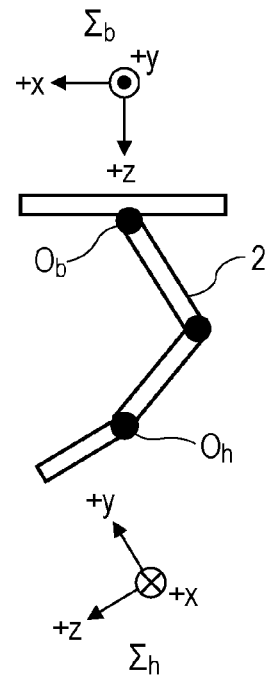
FIG. 6 is an illustrative diagram of a coordinate system in the master-slave robot of the first embodiment of the present disclosure.

A description will be given of a method of calculating, by master motion information correcting unit 112, an amount of movement of hand 4 caused by master arm mechanism 104. Each of motion information of master arm mechanism 104 shown in FIG. 4 indicates a position and a posture in base coordinate system $1b$ with reference to point of origin $O_b$ in FIG. 6. The motion information is transformed by master motion information correcting unit 112 into an amount of movement in hand coordinate system $\Sigma_h$ with reference to point of origin $O_h$ of hand 4. Specifically, master motion information correcting unit 112 applies a transformation matrix ${}^bT_h$ to amount of movement $d_b$ of a position and a posture for each sampling cycle in base coordinate system $\Sigma_b$. Thus, master motion information correcting unit 112 calculates amount of movement $d_h$ of a position and a posture for each sampling cycle in hand coordinate system $\Sigma_h$. Amount of movement d as used herein indicates a difference between the position and posture $p_0$ obtained at time point to and the position and posture $p_1$ obtained at time point $t_1$ elapsed by one sampling time from time point $t_0$, and $d=\Delta_p=p_1-p_0$.

Next, a method of calculating an amount-of-movement instruction value by master motion information correcting unit 112 will be described.

First, a case of application of a gain will be described. Master motion information correcting unit 112 applies gain $k_d$ (e.g., 0.1) to each of elements of amount of movement $d_h$ of a position and a posture (position (x, y, z) and posture ($r_x$, $r_y$, $r_z$)) for each sampling cycle in the above-described hand coordinate system $\Sigma_h$. Thus, master motion information correcting unit 112 calculates corrected master motion information (amount-of-movement instruction value dm). When a movement of slave arm mechanism 105 is increased with respect to a movement of master arm mechanism 104, master motion information correcting unit 112 sets gain $k_d$ to a value greater than 1, and when reduced, master motion information correcting unit 112 sets gain $k_d$ to a value smaller than 1. For gain $k_d$, a constant can be set for each element by master motion information correcting unit 112.

Next, a case of application of a filter for correcting hand shaking will be described. Master motion information correcting unit 112 applies a filter to each of elements of a position and a posture (position (x, y, z) and posture ($r_x$, $r_y$, $r_z$)) for each sampling cycle in hand coordinate system $\Sigma_h$. Here, a low-pass filter is used as the filter. As a parameter of the low-pass filter, a cut-off frequency is changed. The larger the value of the cut-off frequency is, the smaller the filter is to be applied, and the smaller the value of the cut-off frequency is, the larger the filter is to be applied. Master motion information correcting unit 112 calculates an amount of movement for a position and a posture having been filtered, and applies a gain to the amount of movement and uses the resulting amount of movement as corrected maser motion information.

A method of setting a gain or a parameter of a filter by master motion information correcting unit 112 will be described below.

Figure 7A:
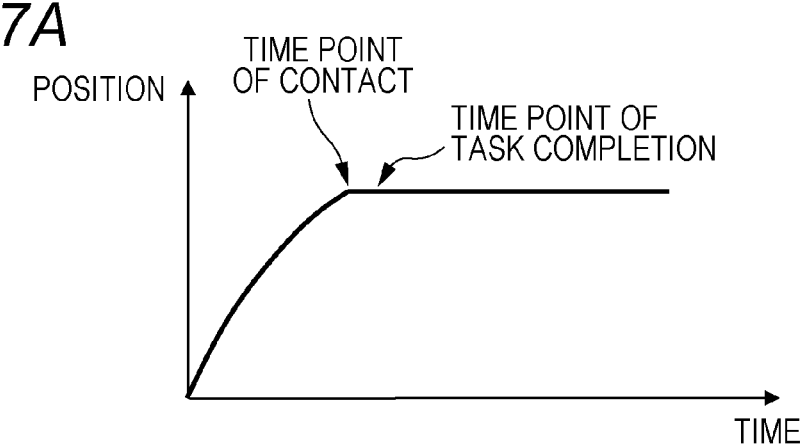
FIG. 7A is a relationship diagram between time and a position for contact tasks performed by operators having different arm weights in the master-slave robot of the first embodiment of the present disclosure.
Figure 7B:
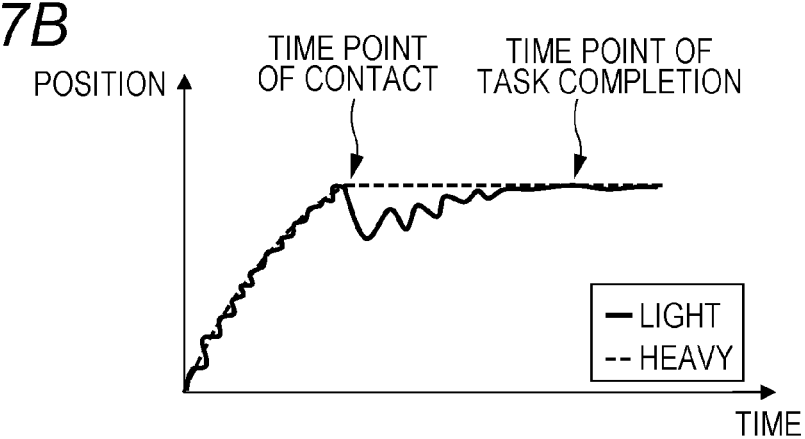
FIG. 7B is a relationship diagram between time and a position for the contact tasks performed by the operators having different arm weights in the master-slave robot of the first embodiment of the present disclosure.

Master motion information correcting unit 112 sets parameters, based on physical information which is input from physical information obtaining unit 111. Here, attention is focused on a fact that an operator having a heavy arm weight has a small positional deviation upon a contact and has small minute hand shaking, compared to an operator having a light arm weight. This will be described with reference to FIGS. 7A and 7B showing results of a case in which operators having different arm weights perform tasks involving a contact. FIG. 7A shows a result for an operator having a heavy arm weight and FIG. 7B shows a result for an operator having a light arm weight. In FIGS. 7A and 7B, a horizontal axis represents time and a vertical axis represents a position of slave arm mechanism 105. A contact occurs at a time point described as a time point of contact in FIGS. 7A and 7B. It can be seen from FIG. 7A that, in the case of the operator having a heavy arm weight, slave arm mechanism 105 approaches in a stable path up to the time point of contact, and even after the contact, slave arm mechanism 105 stays in the same position without a positional deviation and the task is completed immediately. On the other hand, it can be seen from FIG. 7B that, in the case of the operator having a light arm weight, slave arm mechanism 105 approaches in a path with hand shaking up to the time point of contact, and upon the first contact, slave arm mechanism 105 jerks in response to a reaction. Thus, even after the contact, a positional deviation occurs and it takes time for slave arm mechanism 105 to stay in the same position, resulting in a long task completion time compared to the task completion time in FIG. 7A. That is, the operator having a heavy arm weight can perform stable manipulations. As a result, master motion information correcting unit 112 sets larger movement gain $k_d$ and a higher cut-off frequency for the operator having a heavy arm weight. Conversely, in order for the operator having a light arm weight to perform more stable manipulations, master motion information correcting unit 112 sets smaller movement gain $k_d$ and a lower cut-off frequency for the operator having a light arm weight so as to further reduce an amount of movement. Thus, even if slave arm mechanism 105 jerks, since an amount of that movement is small, an influence by the movement is small.

An example of a specific method of setting a movement gain and a cut-off frequency will be described. First, a case will be described in which physical information includes only arm weight information. Values (reference values) of a reference arm weight, a reference movement gain, and a reference cut-off frequency are stored in an internal storage unit. Master motion information correcting unit 112 calculates a movement gain and a cut-off frequency, as differences in arm weight information from the reference values. For example, it is assumed that the reference values are set to 4.5 kg as an arm weight, 0.05 as a movement gain, and 20 Hz as a cut-off frequency. In addition, it is assumed that a rate of change of the movement gain with respect to the arm weight is set to 0.01/kg and a rate of change of the cut-off frequency with respect to the arm weight is set to 2 Hz/kg. Under those conditions, when an arm weight of a given operator is 5.0 kg, a movement gain is calculated to be 0.055 (=0.05+0.01×(5.0−4.5)) by master motion information correcting unit 112, and a cut-off frequency is calculated to be 21 (=20+2×(5.0−4.5)) Hz by master motion information correcting unit 112. When an operator has an arm weight of 2.5 kg, a movement gain is calculated to be 0.03 (=0.05+0.01×(2.5−4.5)) by master motion information correcting unit 112, and a cut-off frequency is calculated to be 16 (=20+2×(2.5−4.5)) Hz by master motion information correcting unit 112. Although in this example master motion information correcting unit 112 calculates a movement gain and a cut-off frequency using a linear relationship, master motion information correcting unit 112 can use various calculation methods such as a polynomial or having a table.

FIG. 8 is a data diagram showing a relationship between an arm weight and a movement gain and a cut-off frequency which are calculated in the manner described above. In FIG. 8, master motion information correcting unit 112 performs settings such that there is a one-to-one correspondence between an arm weight and an amount of correction of movement (a movement gain and a cut-off frequency). In this manner, master motion information correcting unit 112 calculates an amount of correction of movement, according to an arm weight.

In addition, when master motion information correcting unit 112 determines that physical information also includes grip information, the grip information is also stored as a reference value, and master motion information correcting unit 112 further corrects a value of a parameter calculated from arm weight information. A method of determination by master motion information correcting unit 112 determines that when a value of grip information is stored in master motion information obtained by master motion information obtaining unit 110, physical information also includes grip information. The correction is made such that, when master motion information correcting unit 112 determines that the grip information is larger than its reference value, master motion information correcting unit 112 corrects a value of a movement gain or a cut-off frequency to a large value. When master motion information correcting unit 112 determines that the grip information is smaller than its reference value, master motion information correcting unit 112 corrects the value of the movement gain or the cut-off frequency to a small value. The correction is thus made because the larger the value of grip is, the more firmly master arm mechanism 104 can be gripped, making it possible to perform stable manipulations. For example, it is assumed that a reference value of grip is 45 kg. When a given operator has a grip of 55 kg, master motion information correcting unit 112 multiplies a movement gain and a cut-off frequency which are calculated from arm weight information, by 1+0.01×(55−45)=1.1. In a case of a grip of 30 kg, master motion information correcting unit 112 multiplies the movement gain and the cut-off frequency by 1+0.01×(30−45)=0.85.

When master motion information correcting unit 112 determines that physical information also includes dominant arm information, master motion information correcting unit 112 further makes a correction, according to the dominant arm information to be input. A method of determination by master motion information correcting unit 112 determines that when a value of dominant arm information is stored in master motion information obtained by master motion information obtaining unit 110, physical information also includes dominant arm information. As an example of the correction, when master motion information correcting unit 112 determines that dominant arm information is "2" (an arm used to perform manipulations is a dominant arm), master motion information correcting unit 112 does not make a correction. When master motion information correcting unit 112 determines that dominant arm information is "1" (an arm used to perform manipulations is not a dominant arm), master motion information correcting unit 112 corrects a value of a movement gain or a cut-off frequency to a small value. The correction is thus made because manipulating master arm mechanism 104 by a dominant arm can perform stable manipulations. For example, master motion information correcting unit 112 multiplies a movement gain and a cut-off frequency which are calculated from arm weight information, by a factor of 1.0 for a case of a dominant arm, and multiplies the movement gain and the cut-off frequency by a factor of 0.8 for a case of not a dominant arm. The values are input by operator 1 to master motion information correcting unit 112 using master input IF 117.

In the above-described method, even when there is no change in weight, for example, calculations can be performed by master motion information correcting unit 112 by the same procedure.

Figure 9:
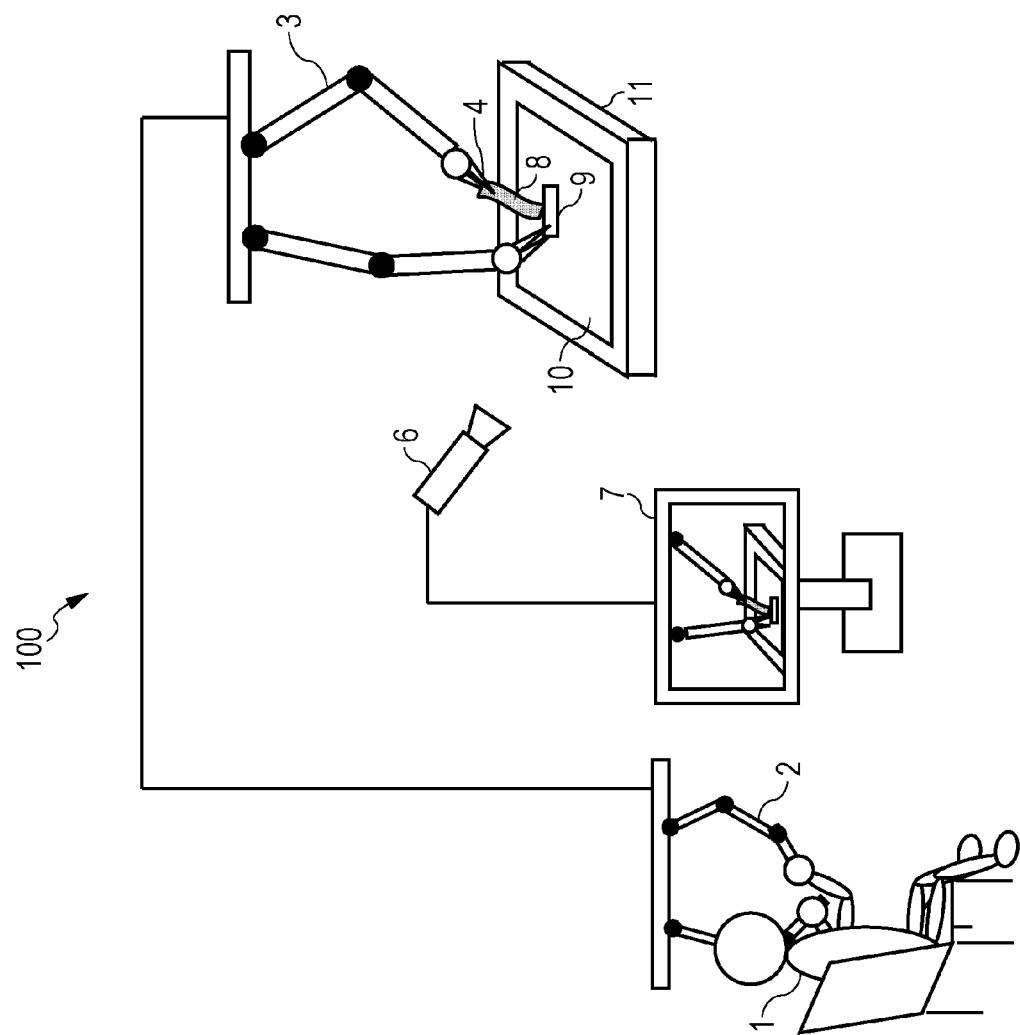
FIG. 9 is a diagram showing a summary of a configuration of a master-slave robot having two arms of the first embodiment of the present disclosure.

Here, the case of performing manipulations by an arm that is not a dominant arm refers to a case of performing another task by the dominant arm or a case in which, as shown in FIG. 9, operator 1 uses a master-slave robot having two arms. In FIG. 9, a right arm of operator 1 is his/her dominant arm, and operator 1 is performing a main task with his/her right arm. A left arm that is not his/her dominant arm plays a support role of supporting so as to prevent a connector having insertion opening 9 from moving. Such a master-slave robot having two arms may be used as a master-slave robot used for medical applications, for example.

FIG. 10 shows an example of corrected master motion information (information on a position (x, y, z) and a posture ($r_x$, $r_y$, $r_z$)) and time information.

Master motion information correcting unit 112 outputs calculated corrected master motion information and time information to slave controller 116.

(Master Input IF 117)

Master input IF 117 is used, for example, when operator 1 selects an item using a keyboard, a mouse, a touch panel, an audio input, or the like, or when operator 1 inputs a number using a keyboard, a mouse, a touch panel, an audio input, or the like.

<Description of the Control Apparatus for the Slave Arm>

Control apparatus 103 for the slave arm 3 includes slave controller 116.

(Slave Controller 116)

Corrected master motion information and time information are input to slave controller 116 from master motion information correcting unit 112. Slave controller 116 generates instruction values so that slave arm mechanism 105 can move according to the obtained corrected master motion information.

Now, a method of generating instruction values by slave controller 116 will be described. Corrected master motion information obtained by slave controller 116 is information about an amount of movement of hand 4. Thus, first, slave controller 116 calculates a position and a posture that move by an amount corresponding to the obtained amount of movement, in the coordinate system of hand 4 of slave arm mechanism 105. Slave controller 116 transforms the position and posture in the coordinate system of hand 4 which are calculated by slave controller 116 into a position and a posture in the base coordinate system of slave arm mechanism 105. Then, slave controller 116 generates instruction values that allow slave arm mechanism 105 to move to the transformed position and posture in the base coordinate system of slave arm mechanism 105. To control slave arm mechanism 105 by slave controller 116 based on the generated instruction values, slave controller 116 generates instruction values for drive apparatuses, for example, motors, for respective rotating shafts of slave arm mechanism 105.

Slave controller 116 outputs the generated instruction values for slave arm mechanism 105 to slave arm mechanism 105 on a per sampling cycle basis.

<Description of the Master Arm Mechanism>

The computing units included in the encoders obtain motion information of master arm mechanism 104 using the encoders of master arm mechanism 104 for every certain period of time (e.g., every 1 msec), using the timer included in master motion information obtaining unit 110. Master arm mechanism 104 outputs the motion information to master motion information obtaining unit 110.

Master arm mechanism 104 has encoders disposed at its respective joints. Here, master arm mechanism 104 is a six-joint multilink manipulator with six flexibilities. Note that numbers of the joints and flexibilities of master arm mechanism 104 are not limited to the numbers in the first embodiment and may be any number greater than or equal to 1.

<Description of the Slave Arm Mechanism>

Slave arm mechanism 105 is controlled according to instruction values from slave controller 116.

Slave arm mechanism 105 has motors and encoders at its respective joints and thus can be controlled to a desired position and posture. Here, slave arm mechanism 105 is a six-joint multilink manipulator with six flexibilities. Note that numbers of the joints and flexibilities of slave arm mechanism 105 are not limited to the numbers in the first embodiment and may be any number greater than or equal to 1.

Figure 11:
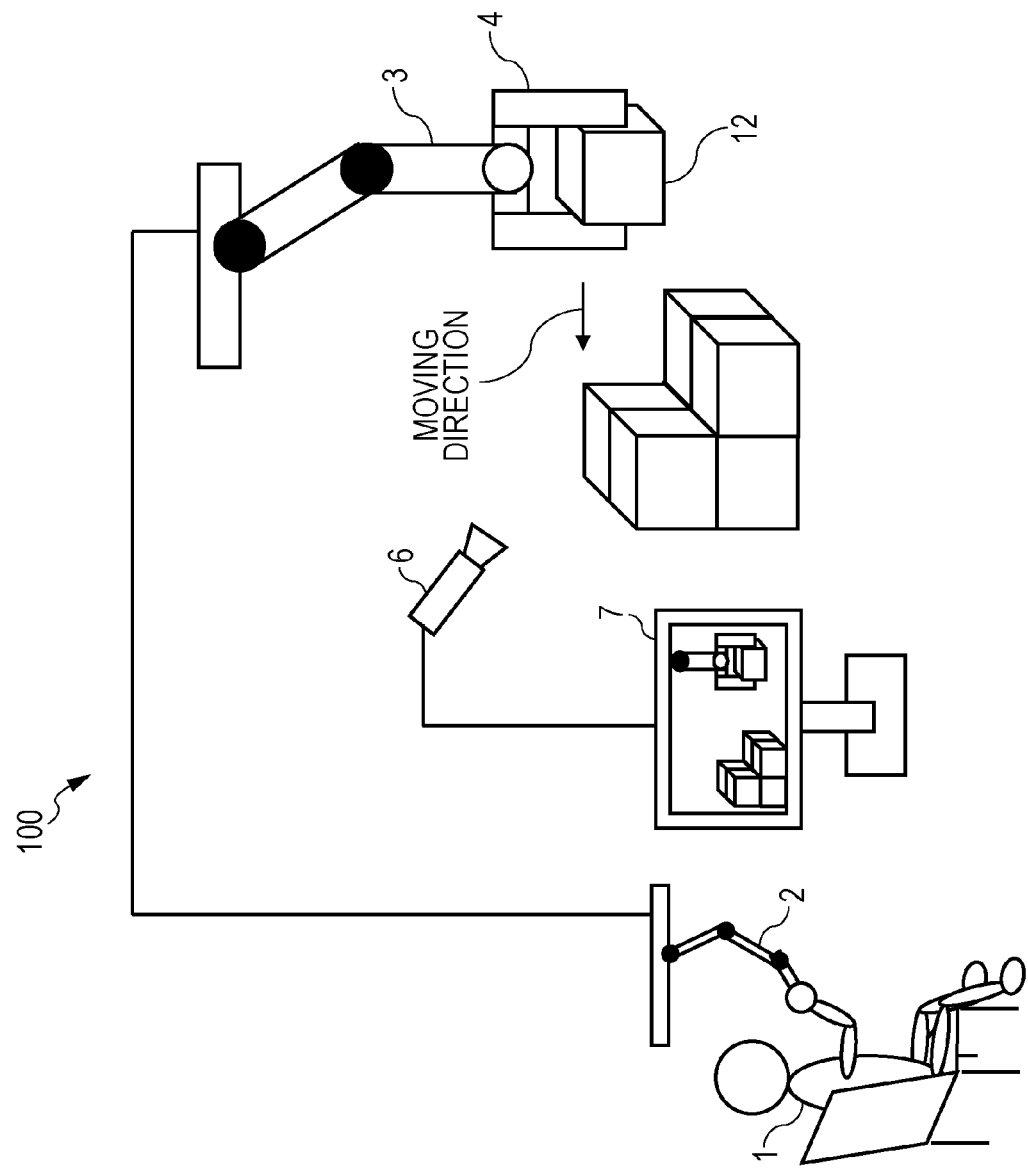
FIG. 11 is a diagram showing a summary of a configuration of the master-slave robot that performs an increase task in the first embodiment of the present disclosure.

Note that although a case of reducing master motion information which is performed for a fine task has been described so far, the first embodiment can also be applied to a case of increasing master motion information which is performed for a task with a large object. For example, the first embodiment can be applied to a task with a large object such as a task in a building site or in space. When a task of moving a large object such as a task shown in FIG. 11 is performed, the first embodiment is used, and master motion information correcting unit 112 corrects a movement gain to 1.0 or greater. Thus, slave arm mechanism 105 can make a large movement, an amount of which is larger than an amount of movement of master arm mechanism 104 made by operator 1.

<Flowcharts>

A manipulation procedure of master-slave robot 100 of the first embodiment will be described with reference to flowcharts of FIGS. 12 and 13.

Figure 12:
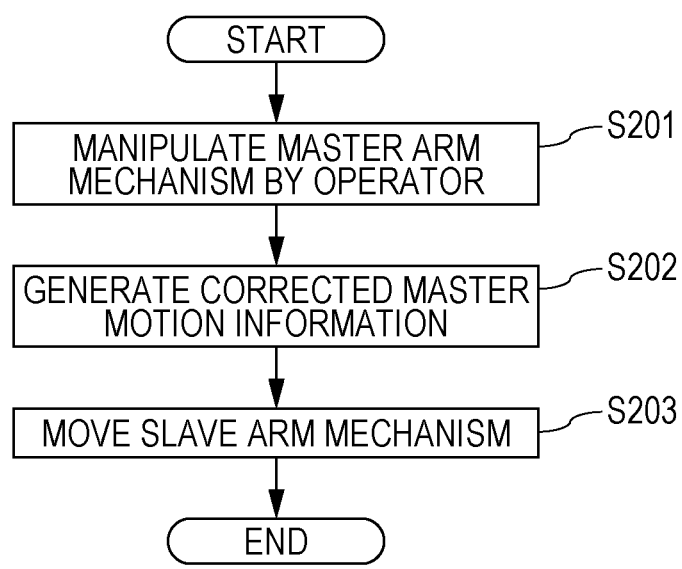
FIG. 12 is a flowchart of a manipulation procedure of the master-slave robot of the first embodiment of the present disclosure.

FIG. 12 shows an example of a manipulation of master-slave robot 100 of the first embodiment.

First, in step S201, operator 1 grips and manipulates master arm mechanism 104 while watching an image displayed on display 7. Master motion information obtaining unit 110 obtains master motion information. Processing proceeds to step S202.

Then, in step S202, master motion information correcting unit 112 corrects, based on physical information, the master motion information obtained from master motion information obtaining unit 110, and thereby generates corrected master motion information which is used to move slave arm mechanism 105, and outputs the corrected master motion information to slave controller 116. Processing proceeds to step S203.

Then, in step S203, slave controller 116 allows slave arm mechanism 105 of slave arm 3 to move according to the corrected master motion information obtained from master motion information correcting unit 112, to perform a task.

Figure 13:
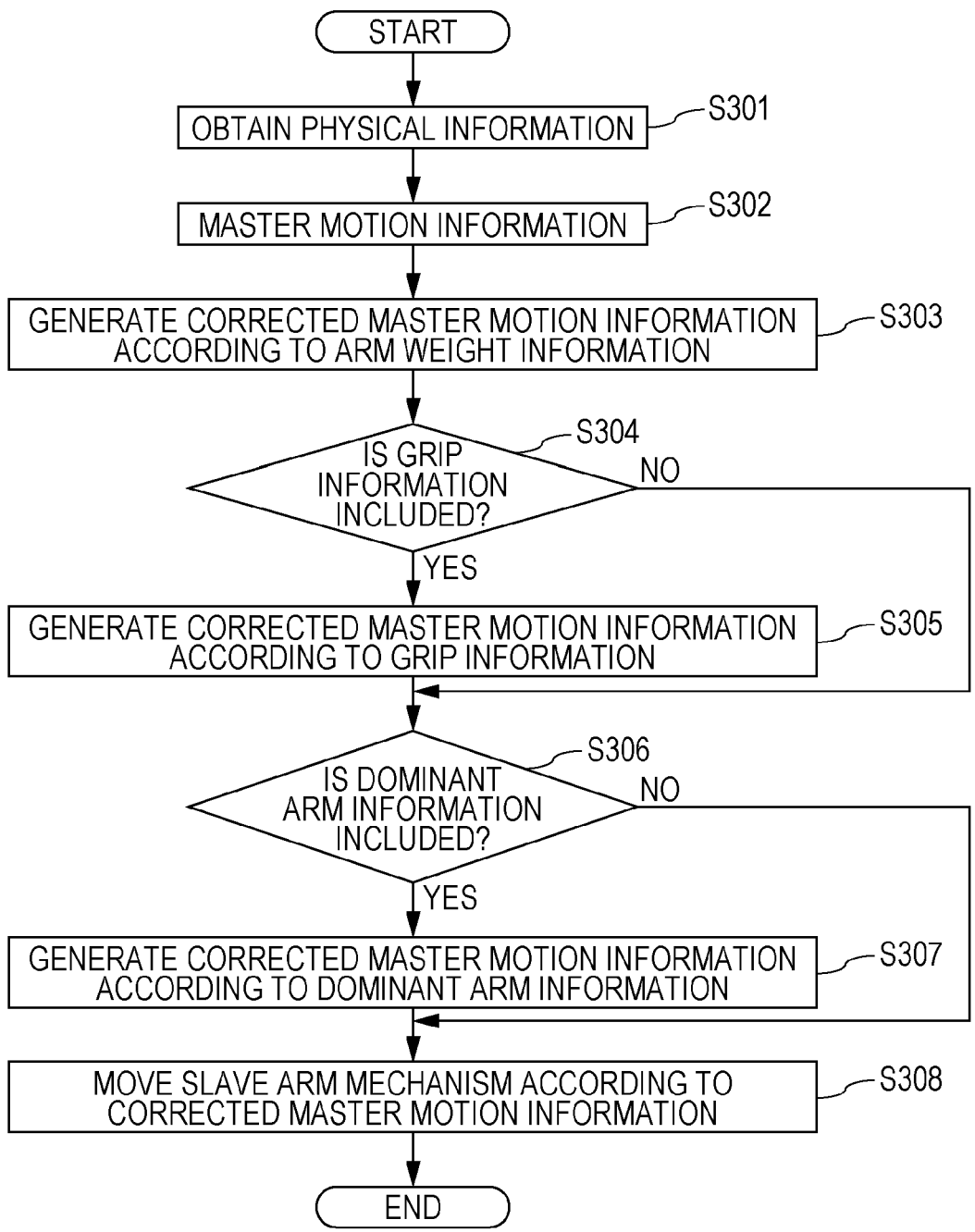
FIG. 13 is a flowchart of a correction procedure of the master-slave robot of the first embodiment of the present disclosure.

In FIG. 13, steps S201 to S203 of the flowchart shown in FIG. 12 will be described. Of those steps, particularly, a description will be given in detail of a correction procedure in the generation of corrected master motion information by master motion information correcting unit 112 in step S202.

First, in step S301, physical information obtaining unit 111 obtains physical information and outputs the physical information to master motion information correcting unit 112. Processing proceeds to step S302.

Then, in step S302, master motion information obtaining unit 110 obtains master motion information and outputs the master motion information to master motion information correcting unit 112. Processing proceeds to step S303.

Then, in step S303, master motion information correcting unit 112 generates, based on the master motion information obtained from master motion information obtaining unit 110, corrected master motion information, using arm weight information included in the physical information which is obtained from physical information obtaining unit 111. Thereafter, processing proceeds to step S304.

Then, in step S304, master motion information correcting unit 112 determines whether the physical information obtained from physical information obtaining unit 111 includes grip information. If master motion information correcting unit 112 determines that the physical information includes grip information, processing proceeds to step S305.

On the other hand, if master motion information correcting unit 112 determines that the physical information does not include grip information, processing proceeds to step S306.

Then, in step S305, master motion information correcting unit 112 generates, based on the previously generated corrected master motion information, corrected master motion information again, using the grip information included in the physical information and replaces the previously generated corrected master motion information with the generated corrected master motion information. Thereafter, processing proceeds to step S306.

Then, in step S306, master motion information correcting unit 112 determines whether the physical information includes dominant arm information. If master motion information correcting unit 112 determines that the physical information includes dominant arm information, processing proceeds to step S307. On the other hand, if master motion information correcting unit 112 determines that the physical information does not include dominant arm information, processing proceeds to step S308.

Then, in step S307, master motion information correcting unit 112 generates, based on the previously generated corrected master motion information, corrected master motion information again, using the dominant arm information included in the physical information which is obtained from physical information obtaining unit 111, and outputs the generated corrected master motion information to slave controller 116. Processing proceeds to step S308.

Then, in step S308, slave controller 116 generates instruction values for slave arm mechanism 105, according to the corrected master motion information obtained from master motion information correcting unit 112, and outputs the generated instruction values to slave arm mechanism 105. Slave arm mechanism 105 is allowed to move based on the instruction values to perform a task.

Effect of the First Embodiment

Master motion information correcting unit 112 corrects master motion information based on arm weight information, grip information, or dominant arm information which is a physical characteristic of operator 1. Slave arm mechanism 105 performs a task under control of slave controller 116. Thus, even in a case of different operators 1, variations in quality and efficiency can be overcome.

Note that in the first embodiment a correction is made such that the heavier the arm weight of operator 1, the larger the movement of slave arm mechanism 105. On the other hand, it is also possible that, in order to stabilize a course of operator 1 with a light arm weight, master motion information correcting unit 112 sets an arbitrary threshold value for the arm weight, and only for operator 1 with a lighter arm weight than the threshold value, master motion information correcting unit 112 makes a correction so as to reduce an amount of movement of slave arm mechanism 105.

Second Embodiment

A description will be given of a summary of master-slave robot 100B including control apparatus 101B for master-slave robot 100B of a second embodiment of the present disclosure.

Figure 14:
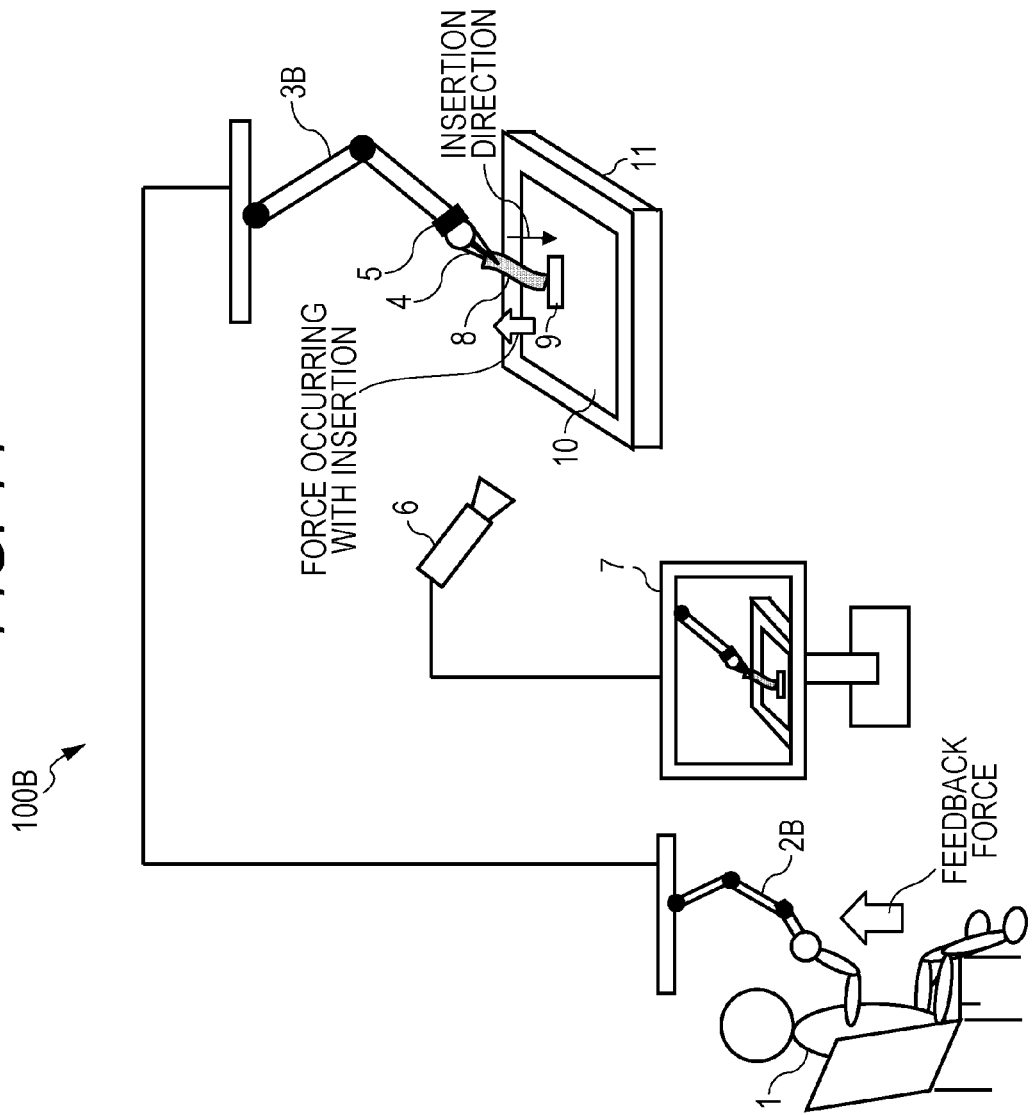
FIG. 14 is a diagram showing a summary of a configuration of a master-slave robot of a second embodiment of the present disclosure.

FIG. 14 shows a state of a task of inserting fine part 8 using master-slave robot 100B.

Master-slave robot 100B differs from master-slave robot 100 of FIG. 1 in a following point. Specifically, force sensor 5 is attached to master-slave robot 100B. A force measured by force sensor 5 is fed back to master arm mechanism 104B of master arm 2B from slave arm mechanism 105 of slave arm 3B. Thus, operator 1 can manipulate slave arm mechanism 105 as if he/she were directly manipulating fine part 8.

Force sensor 5 is placed at a wrist portion of hand 4 and measures a reaction force occurring when fine part 8 comes into contact with insertion opening 9 or device 10.

Figure 15:
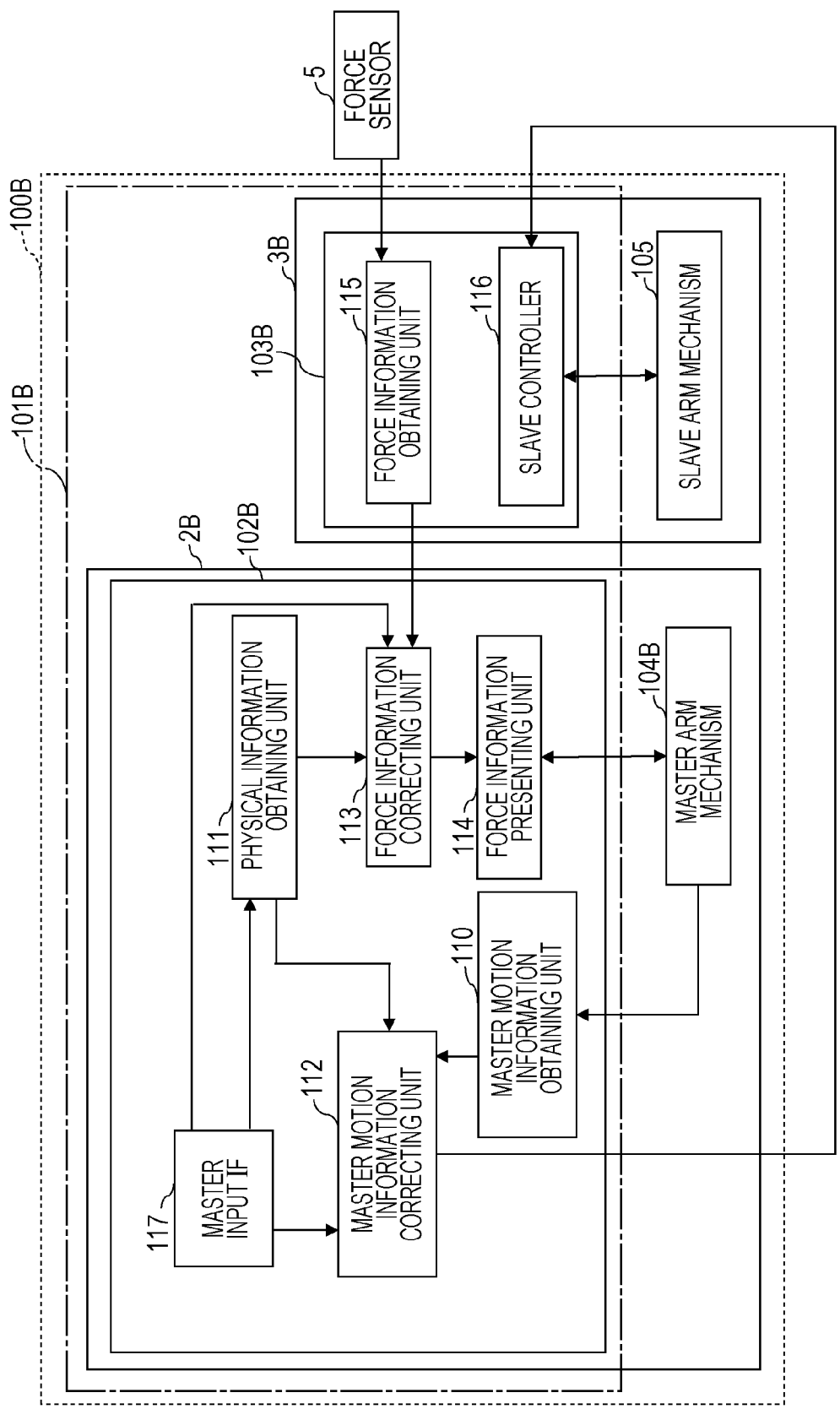
FIG. 15 is a block diagram of the master-slave robot of the second embodiment of the present disclosure.

FIG. 15 is a block diagram of master-slave robot 100B of the second embodiment of the present disclosure. Master motion information obtaining unit 110, physical information obtaining unit 111, master motion information correcting unit 112, and master input IF 117 which are included in control apparatus 102B for master arm 2B in master arm 2B, slave arm mechanism 105 in slave arm 3B, and slave controller 116 in control apparatus 103B for slave arm 3B of the second embodiment of the present disclosure are the same as those of the first embodiment and thus are denoted by common reference signs. A description of the common portions is omitted and a description will be given below in detail of only portions different from those in the first embodiment (i.e., force sensor 5, and force information correcting unit 113 and force information presenting unit 114 which are included in control apparatus 102B for master arm 2B, and force information obtaining unit 115 in slave arm 3B).

(Force Information Correcting Unit 113)

Physical information is input to force information correcting unit 113 from physical information obtaining unit 111. Force information and time information are input to force information correcting unit 113 from force information obtaining unit 115. Force information correcting unit 113 applies a gain calculated from the physical information to the obtained force information, and outputs the resulting information as corrected force information to force information presenting unit 114.

A method of application of a gain by force information correcting unit 113 will be described. Force information correcting unit 113 applies gain $k_f$ (e.g., 1.5) to each of elements (force ($F_x$, $F_y$, $F_z$) and posture ($M_x$, $M_y$, $M_z$)) of force information for each sampling cycle which are obtained by force information obtaining unit 115. Thus, force information correcting unit 113 calculates corrected force information. For gain $k_f$, a constant can be set for each element by force information correcting unit 113.

A method of setting a gain by force information correcting unit 113 will be described. Force information correcting unit 113 sets a gain, based on physical information which is input to force information correcting unit 113 from physical information obtaining unit 111. Here, attention is focused on a fact that an operator having a heavy arm weight can withstand a large force compared to an operator having a light arm weight, and a fact that the operator having a heavy arm weight is less likely to feel a small force compared to the operator having a light arm weight. The facts are also revealed from a fact that, when operators having different arm weights perform the same task involving a contact, as an example, while a force load on an object is 1.44 N for an operator having a light arm, the force load is 2.25 N for an operator having a heavy arm. That is, the operator having a heavy arm weight has a larger load on the object. As a result, a larger gain is set for the operator having a heavy arm weight. By doing so, even the operator having a heavy arm weight can feel a small force and thus application of a large force load can be prevented.

An example of a specific method of setting a gain by force information correcting unit 113 will be described. First, a case will be described in which physical information includes only arm weight information. Values (reference values) of a reference arm weight and a reference force gain are stored in an internal storage unit. Force information correcting unit 113 calculates a force gain as a difference in arm weight information from the reference values. For example, it is assumed that the reference values are set to 4.5 kg as an arm weight and 1.0 as a force gain, and a rate of change of the force gain with respect to the arm weight is set to 0.2/kg. Under these conditions, when an arm weight of a given operator is 5.0 kg, the force gain is calculated to be 1.1 (=1.0+0.2×(5.0−4.5)). When an operator has an arm weight of 2.5 kg, the force gain is calculated to be 0.6 (=1.0+0.2× (2.5−4.5)) by force information correcting unit 113. Although in this example force information correcting unit 113 calculates a force gain using a linear relationship, force information correcting unit 113 can use various calculation methods such as a polynomial or having a table.

FIG. 16 is a data diagram showing a relationship between an arm weight and a force gain which is calculated in the manner described above. As such, force information correcting unit 113 calculates an amount of correction of force, according to an arm weight. FIG. 17 is a data diagram showing a relationship between an arm weight, an amount of correction of movement, and an amount of correction of force, together with amounts of correction of movement calculated in the first embodiment.

When physical information also includes grip information, the grip information is also stored as a reference value. Force information correcting unit 113 further corrects a value of a parameter calculated from arm weight information. The correction is made such that, when the grip information is larger than its reference value, force information correcting unit 113 corrects a value of a force gain to a large value. When the grip information is smaller than its reference value, force information correcting unit 113 corrects the value of the force gain to a small value. The correction is thus made because the larger the value of grip is, the more firmly master arm mechanism 104B can be gripped, making it possible to withstand a larger force. For example, it is assumed that a reference value of grip is 45 kg. When a given operator has a grip of 55 kg, force information correcting unit 113 multiplies a force gain which is calculated from arm weight information, by 1+0.01×(55−45)=1.1. In a case of a grip of 30 kg, force information correcting unit 113 multiplies the force gain by 1+0.01×(30−45)=0.85.

When physical information also includes dominant arm information, force information correcting unit 113 further makes a correction, according to the dominant arm information to be input. As an example of the correction, when dominant arm information is "2" (an arm used to perform manipulations is a dominant arm), force information correcting unit 113 does not make a correction. When dominant arm information is "1" (an arm used to perform manipulations is not a dominant arm), force information correcting unit 113 corrects a value of a force gain to a small value. The correction is thus made because manipulating master arm mechanism 104B by a dominant arm can withstand a larger force. For example, a force gain which is calculated from arm weight information is multiplied by a factor of 1.0 for a case of a dominant arm, and is multiplied by a factor of 0.8 for a case of not a dominant arm. The values are input by operator 1 to force information correcting unit 113 using master input IF 117.

Force information correcting unit 113 outputs calculated corrected force information and time information to force information presenting unit 114.

Note that, for timing of a force correction, a force correction is made during a period from a start of a task until an end of the task.

Figure 18:
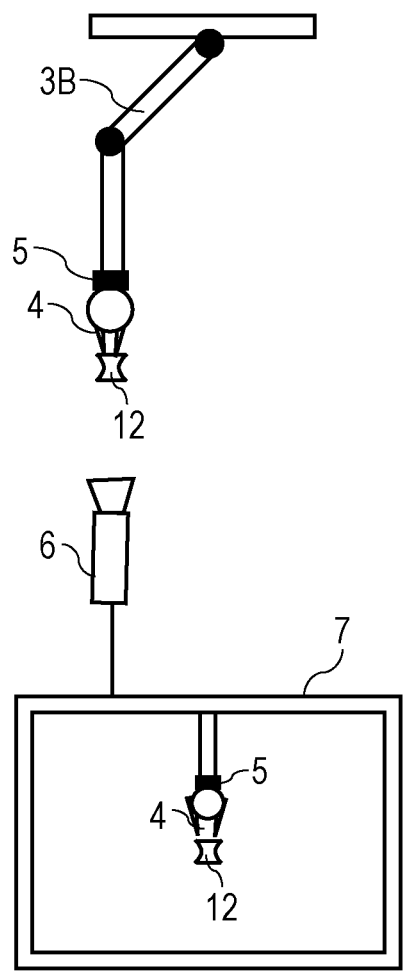
FIG. 18 is an illustrative diagram of a carrying task in the master-slave robot of the second embodiment of the present disclosure.
Figure 19:
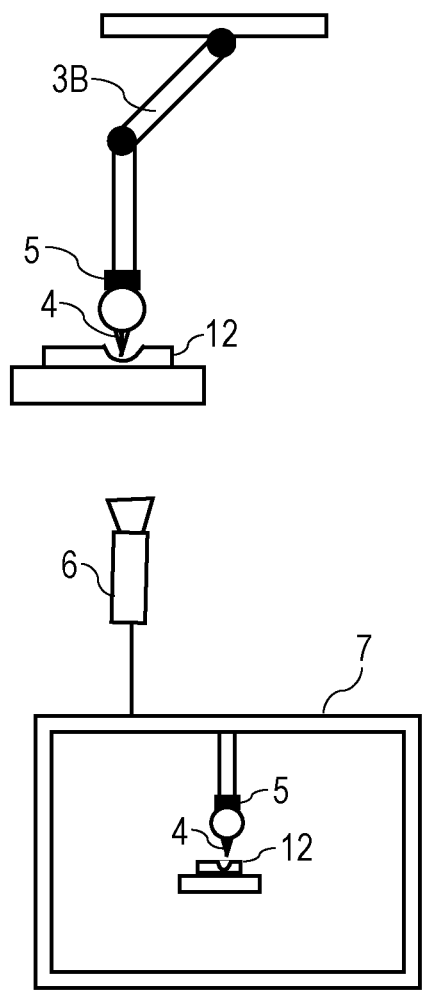
FIG. 19 is an illustrative diagram of a pressing task in the master-slave robot of the second embodiment of the present disclosure.

FIGS. 18 and 19 show examples of application of a force correction to other tasks. FIG. 18 shows a task of slave arm mechanism 105 gripping and carrying object 12 by hand 4. FIG. 19 shows a task of slave arm mechanism 105 pressing object 12. Also in these examples, since operator 1 performs a task while feeling a force, by force information correcting unit 113 making a force correction according to physical characteristics of operator 1, variations between operators 1 can be overcome.

Note that although force information correcting unit 113 corrects a magnitude of force information, it is also possible to use a method in which force information correcting unit 113 corrects a force information update cycle. In the above-described description, force information is updated in fixed cycles (e.g., 1 msec). On the other hand, force information correcting unit 113 changes an update cycle to be faster or slower. Specifically, when a magnitude of force information is to be increased, force information correcting unit 113 makes the force information update cycle slower without changing the magnitude of the force information. When a magnitude of force information is to be doubled, for example, force information correcting unit 113 doubles the force information update cycle. On the other hand, when a magnitude of force information is to be reduced, force information correcting unit 113 makes the force information update cycle faster without changing the magnitude of the force information. When a magnitude of force information is to be halved, for example, force information correcting unit 113 halves the force information update cycle.

Figure 20:
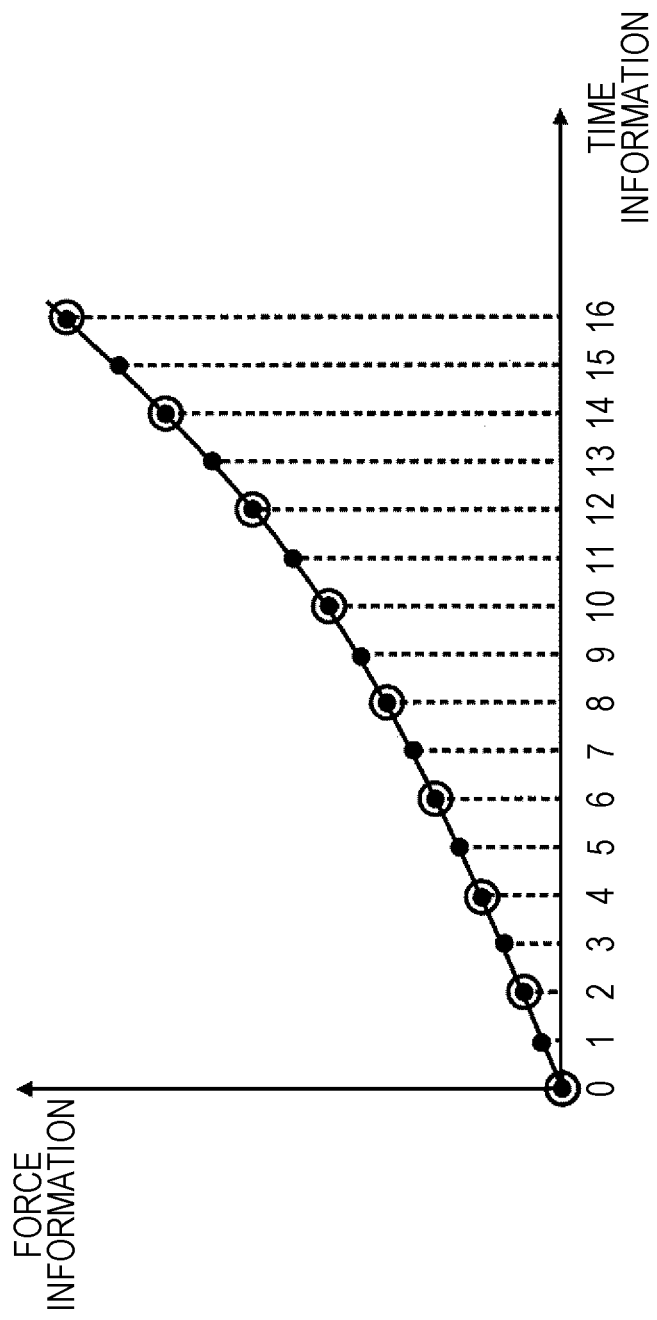
FIG. 20 is an illustrative diagram of a change of a force information update cycle in the master-slave robot of the second embodiment of the present disclosure.

With reference to FIG. 20, a description will be given of a reason that changing the force information update cycle can obtain the same effect as an effect obtained by changing a magnitude of force information. FIG. 20 shows chronological data of force information where a horizontal axis represents time information and a vertical axis represents force information. Numbers on the horizontal axis indicate time information. A filled circle of force information indicates data with an update cycle of 1 msec, and an open circle indicates data with an update cycle of 2 msec. When the force information is represented as $F_k$, k=1, 2, 3, . . . for an update cycle of 1 msec, and k=2, 4, 6, . . . for an update cycle of 2 msec. A displacement of force information for each update cycle is represented as $\Delta F_k$. For example, for displacement $\Delta F_2$ of force information for each update cycle for time information of 2, when the update cycle is 1 msec, force information correcting unit 113 calculates $\Delta F_2 = F_2 - F_1$. When the update cycle is 2 msec, force information correcting unit 113 calculates $\Delta F_2 = F_2 - F_0$. Thus, $\Delta F_2$ with an update cycle of 2 msec has a large displacement of force information compared to $\Delta F_2$ with an update cycle of 1 msec. As shown in this example, since the displacement of force information increases when the update cycle is made slower, operator 1 feels that force information has increased. This results from a fact that when operator 1 feels a sense of force, he/she feels a displacement of force.

As such, when force information is corrected, instead of correcting a magnitude of the force information, the force information update cycle can be corrected. Since the magnitude of the force information is not changed upon the correction, the force information is not changed too much. In addition, in a case of a system that cannot correct a magnitude of force information, too, the system can obtain the same effect as an effect obtained by correcting the magnitude of force information.

(Force Information Presenting Unit 114)

Corrected force information and time information are input to force information presenting unit 114 from force information correcting unit 113. In order to present the obtained corrected force information to operator 1 through master arm mechanism 104B, force information presenting unit 114 generates instruction values such that master arm mechanism 104B can output the corrected force information.

A method of generating instruction values by force information presenting unit 114 will be described. When a force controllable arm is used as master arm mechanism 104B, force information presenting unit 114 uses corrected force information as it is as instruction values. When a force uncontrollable, position controllable arm is used as master arm mechanism 104B, force information presenting unit 114 converts corrected force information into position information using Hooke's law, and uses the converted position information as instruction values. To control master arm mechanism 104B based on the generated instruction values, force information presenting unit 114 generates instruction values for motors for respective shafts of master arm mechanism 104B.

Force information presenting unit 114 outputs the generated instruction values for master arm mechanism 104B to master arm mechanism 104B on a per sampling cycle basis.

(Force Sensor 5)

Force sensor 5 is placed at the wrist portion of hand 4 of slave arm mechanism 105, and measures a reaction force occurring when an object comes into contact with a subject. Here, a force sensor is used that is capable of measuring six axes in total, i.e., three forces and three torques. Note that any force sensor can be used as long as the force sensor is capable of measuring one or more axes. Note also that force sensor 5 is implemented by, for example, using a strain gage force sensor.

Force information measured by force sensor 5 is output to force information obtaining unit 115.

(Force Information Obtaining Unit 115)

Force information is input to force information obtaining unit 115 from force sensor 5. FIG. 21 shows force information and time information. Time information is obtained from a timer included in force information obtaining unit 115.

Force information obtaining unit 115 outputs the obtained force information and time information to force information correcting unit 113.

<Description of the Master Arm Mechanism>

Computing units included in encoders of master arm mechanism 104B obtain motion information of master arm mechanism 104B using the encoders for every certain period of time (e.g., every 1 msec), using a timer included in master motion information obtaining unit 110. Master arm mechanism 104B outputs the motion information to master motion information obtaining unit 110. In addition, master arm mechanism 104B is controlled according to instruction values from force information presenting unit 114.

Master arm mechanism 104B has motors and encoders disposed at its respective joints and thus can be controlled to a desired position and posture. Here, master arm mechanism 104B is a six-joint multilink manipulator with six flexibilities. Note that numbers of the joints and flexibilities of master arm mechanism 104B are not limited to the numbers in the second embodiment and may be any number greater than or equal to 1.

<Flowcharts>

A manipulation procedure of master-slave robot 100B of the second embodiment will be described with reference to flowcharts of FIGS. 22 and 23.

Figure 22:
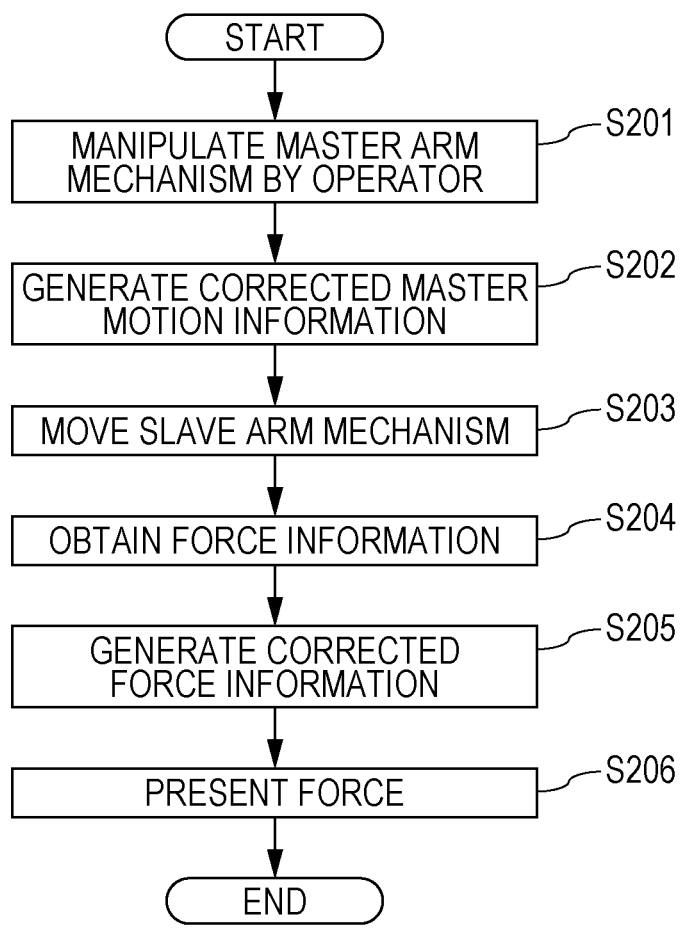
FIG. 22 is a flowchart of a manipulation procedure of the master-slave robot of the second embodiment of the present disclosure.

FIG. 22 shows an example of a manipulation of master-slave robot 100B of the second embodiment.

First, in step S201, operator 1 grips and manipulates master arm mechanism 104B while watching an image displayed on display 7. Master motion information obtaining unit 110 obtains master motion information. Processing proceeds to step S202.

Then, in step S202, master motion information correcting unit 112 corrects the master motion information obtained from master motion information obtaining unit 110, based on physical information obtained from physical information obtaining unit 111, and thereby generates corrected master motion information which is used to move slave arm mechanism 105, and outputs the corrected master motion information to slave controller 116. Processing proceeds to step S203.

Then, in step S203, slave controller 116 allows slave arm mechanism 105 of slave arm 3B to move according to the corrected master motion information obtained from master motion information correcting unit 112, to perform a task. Processing proceeds to step S204.

Then, in step S204, force sensor 5 attached to a hand of slave arm mechanism 105 detects force information generated upon performing the task, and force information obtaining unit 115 obtains the force information detected by force sensor 5. Processing proceeds to step S205.

Then, in step S205, force information correcting unit 113 corrects the force information obtained from force information obtaining unit 115, based on physical information obtained from physical information obtaining unit 111, and thereby generates corrected force information, and outputs the generated corrected force information to force information presenting unit 114. Processing proceeds to step S206.

Then, in step S206, force information presenting unit 114 allows master arm mechanism 104B to present a force according to the corrected force information obtained from force information correcting unit 113. Thus, the force is presented to operator 1 through master arm mechanism 104B.

Figure 23:
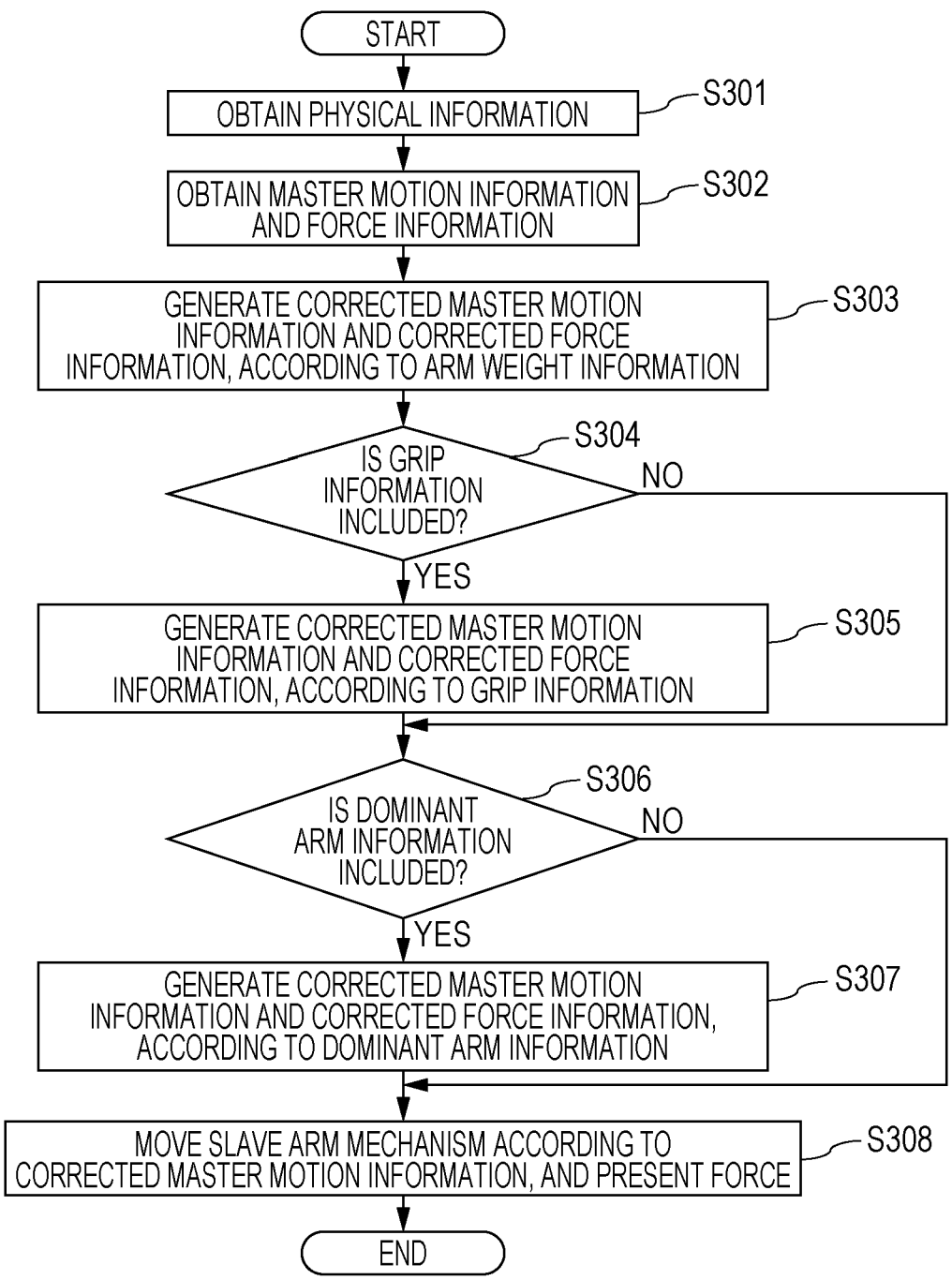
FIG. 23 is a flowchart of a correction procedure of the master-slave robot of the second embodiment of the present disclosure.

In FIG. 23, steps S201 to S206 of the flowchart shown in FIG. 22 will be described. Of those steps, particularly, a description will be given in detail of a procedure for generating corrected master motion information performed by master motion information correcting unit 112 in step S202 and a correction procedure in the generation of corrected force information by force information correcting unit 113 in step S205.

First, in step S301, physical information obtaining unit 111 obtains physical information and outputs the physical information to force information correcting unit 113. Processing proceeds to step S302.

Then, in step S302, master motion information obtaining unit 110 obtains master motion information and outputs the master motion information to master motion information correcting unit 112, and force information obtaining unit 115 obtains force information and outputs the force information to force information correcting unit 113. Processing proceeds to step S303.

Then, in step S303, master motion information correcting unit 112 generates, based on the master motion information, corrected master motion information, using arm weight information included in the physical information. In addition, force information correcting unit 113 generates, based on the force information, corrected force information, using the arm weight information included in the physical information. Thereafter, processing proceeds to step S304.

Then, in step S304, master motion information correcting unit 112 and force information correcting unit 113 determine independently of each other whether the physical information includes grip information. If each of master motion information correcting unit 112 and force information correcting unit 113 determines that the physical information includes grip information, processing proceeds to step S305. On the other hand, if each of master motion information correcting unit 112 and force information correcting unit 113 determines that the physical information does not include grip information, processing proceeds to step S306. The determinations by master motion information correcting unit 112 and force information correcting unit 113 are made independently of each other.

Then, in step S305, master motion information correcting unit 112 generates, based on the previously generated corrected master motion information, corrected master motion information again, using the grip information included in the physical information. In addition, force information correcting unit 113 generates, based on the previously generated corrected force information, corrected force information again, using the grip information included in the physical information. Thereafter, processing proceeds to step S306.

Then, in step S306, master motion information correcting unit 112 and force information correcting unit 113 determine independently of each other whether the physical information includes dominant arm information. If each of master motion information correcting unit 112 and force information correcting unit 113 determines that the physical information includes dominant arm information, processing proceeds to step S307. On the other hand, if each of master motion information correcting unit 112 and force information correcting unit 113 determines that the physical information does not include dominant arm information, processing proceeds to step S308.

Then, in step S307, master motion information correcting unit 112 generates, based on the previously generated corrected master motion information, corrected master motion information again, using the dominant arm information included in the physical information, and outputs the generated corrected master motion information to slave controller 116. In addition, force information correcting unit 113 generates, based on the previously generated corrected force information, corrected force information again, using the dominant arm information included in the physical information, and outputs the generated corrected force information to force information presenting unit 114. Processing proceeds to step S308.

Then, in step S308, slave controller 116 generates instruction values for slave arm mechanism 105, according to the corrected master motion information obtained from master motion information correcting unit 112, and outputs the generated instruction values to slave arm mechanism 105. Slave arm mechanism 105 is allowed to move based on the instruction values to perform a task. On the other hand, force information presenting unit 114 generates instruction values for master arm mechanism 104B, according to the corrected force information obtained from force information correcting unit 113, and outputs the generated instruction values to master arm mechanism 104B. Master arm mechanism 104B presents a force based on the instruction values. Thus, the force is presented to operator 1 through master arm mechanism 104B.

Effect of the Second Embodiment

Force information correcting unit 113 corrects force information based on arm weight information, grip information, or dominant arm information which is a physical characteristic of operator 1, and force information presenting unit 114 presents a force to operator 1 through master arm mechanism 104B. Thus, even in a case of different operators 1, variations in quality and efficiency can be overcome.

Third Embodiment

Figure 24:
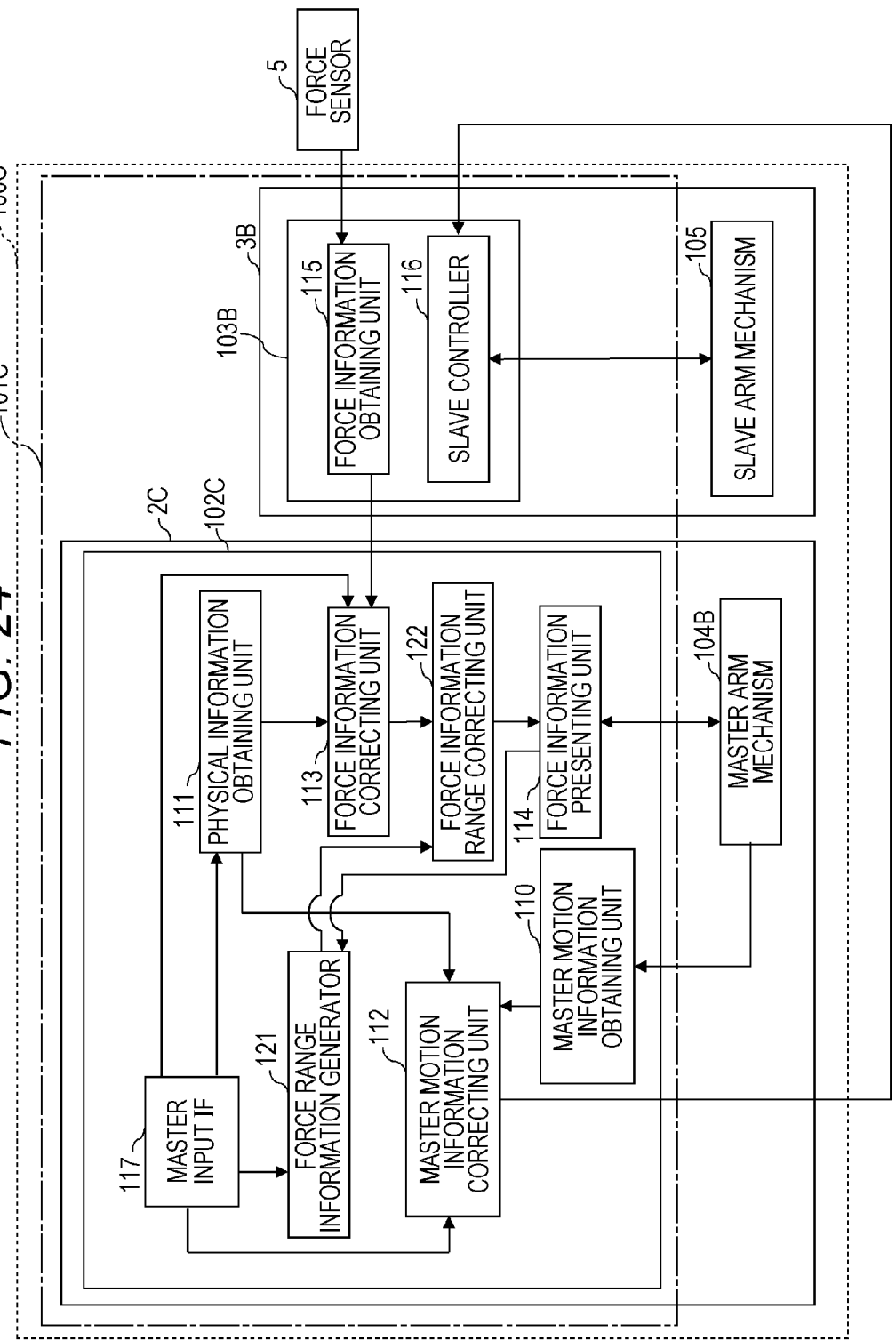
FIG. 24 is a block diagram of a master-slave robot of a third embodiment of the present disclosure.

A description will be given of a summary of master-slave robot 100C including control apparatus 101C for master-slave robot 100C of a third embodiment of the present disclosure. FIG. 24 is a block diagram of master-slave robot 100C of the third embodiment of the present disclosure. Master arm mechanism 104B in master arm 2C, and master motion information obtaining unit 110, physical information obtaining unit 111, master motion information correcting unit 112, force information correcting unit 113, force information presenting unit 114, and master input IF 117 which are included in control apparatus 102C for master arm 2C, and slave arm 3B of the third embodiment of the present disclosure are the same as those of the second embodiment and thus are denoted by common reference signs. A description of the common portions is omitted and a description will be given below in detail of only portions different from those in the second embodiment (force range information generator 121 and force information range correcting unit 122 which are included in control apparatus 102C for master arm 2C).

(Force Range Information Generator 121)

Physical information is input to force range information generator 121 from physical information obtaining unit 111. Force range information generator 121 calculates, from the physical information which is input from physical information obtaining unit 111, force range information including an upper limit and a lower limit of force information according to the physical information.

A method of calculating force range information by force range information generator 121 will be described. A magnitude of a force that operator 1 can withstand and a magnitude of a force that operator 1 can feel vary depending on physical information of operator 1. Force range information generator 121 sets, as an upper limit, a magnitude of a maximum force that operator 1 can withstand without his/her arm becoming unable to tolerate a force and moving, and sets, as a lower limit, a magnitude of a minimum force that operator 1 can feel. A storage unit included in force range information generator 121 stores arm weight information which is physical information and an upper limit and a lower limit for a value of the information. Specifically, force range information generator 121 calculates an upper limit and a lower limit for arm weight information included in input physical information, and stores the upper limit and the lower limit in the storage unit. For example, force range information generator 121 calculates, from arm weight information included in input physical information, an upper limit and a lower limit for the arm weight information and stores, as shown in FIG. 25, those data in the storage unit included in force range information generator 121. In addition, when arm weight information which is input from physical information obtaining unit 111 is not included in data stored in the storage unit, force range information generator 121 calculates an upper limit and a lower limit for the arm weight information by performing a linear approximation. Note that force range information generator 121 can use any approximation method other than a linear approximation.

Figure 26:
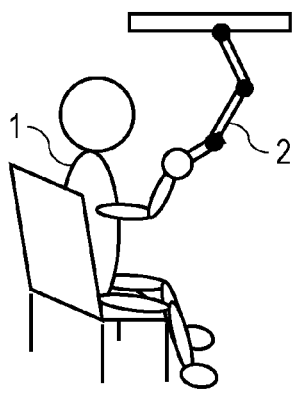
FIG. 26 is an illustrative diagram of a method of obtaining force range information in the master-slave robot of the third embodiment of the present disclosure.

Force range information stored in the storage unit included in force range information generator 121 can also be input by operator 1 using master input IF 117. For a method of obtaining force range information, as shown in FIG. 26, operator 1 grips master arm mechanism 104B, and a force presented by master arm mechanism 104B, i.e., a magnitude of a force presented (controlled) by force information presenting unit 114, is obtained as force range information. Force information presenting unit 114 starts presenting a force from a small force and sets, as a lower limit, a magnitude of a force that operator 1 can feel for the first time. Thereafter, force information presenting unit 114 increases a force presented, and a magnitude of a force that operator 1 cannot withstand without moving is set as an upper limit. The lower limit and upper limit measured in this manner and arm weight information of operator 1 are stored in the storage unit. When two or more force range information are stored in the storage unit in force range information generator 121, force information presenting unit 114 can also calculate an upper limit and a lower limit for other arm weight information by performing a linear approximation. Note that any approximation method other than a linear approximation can be used.

FIG. 25 shows an example of force range information generated by force range information generator 121.

Force range information generator 121 outputs generated force range information to force information range correcting unit 122.

(Force Information Range Correcting Unit 122)

Corrected force information and time information are input to force information range correcting unit 122 from force information correcting unit 113. Force range information is input to force information range correcting unit 122 from force range information generator 121. Force information range correcting unit 122 corrects the input corrected force information such that the corrected force information falls within a range of the force range information, and thereby generates range-corrected force information.

A method of generating range-corrected force information by force information range correcting unit 122 will be described below. Here, two examples will be described with reference to FIGS. 27A and 27B.

Figure 27A:
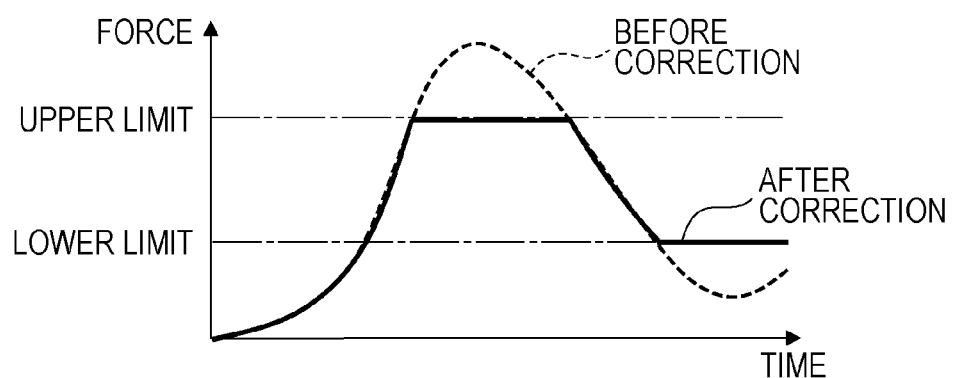
FIG. 27A is an illustrative diagram of a method of generating range-corrected force information in the master-slave robot of the third embodiment of the present disclosure.

A first example is a method in which when corrected force information exceeds an upper limit, force information range correcting unit 122 corrects the corrected force information to the upper limit; on the other hand, when corrected force information exceeds a lower limit, force information range correcting unit 122 corrects the corrected force information to the lower limit. FIG. 27A shows a force before a correction (see a graph indicated by a dashed line) and a force after the correction (see a graph indicated by a solid line). Comparing the force before the correction with the force after the correction, it can be seen that an upper limit and a lower limit are used as threshold values, and when corrected force information exceeds the threshold values, the threshold values are used instead of the corrected force information. Note, however, that when a value of a force which is corrected force information is 0, even if the corrected force information falls below the lower limit, the corrected force information is not corrected. In addition, a correction of the corrected force information starts from a time point when the corrected force information exceeds the lower limit for the first time.

Figure 27B:
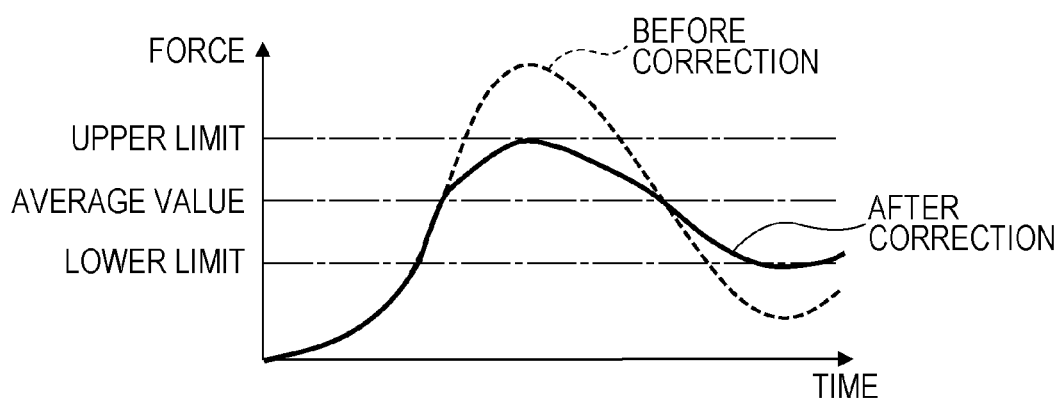
FIG. 27B is an illustrative diagram of a method of generating range-corrected force information in the master-slave robot of the third embodiment of the present disclosure.

A second example is a method in which force information range correcting unit 122 compares an average value of an upper limit and a lower limit with corrected force information, and corrects the corrected force information such that a difference between the average value and the corrected force information approximates an n % average value (i.e., within a range of the average value±n %×the average value). FIG. 27B shows a force before a correction and a force after the correction. It can be seen that by correcting corrected force information, the corrected force information approximates an average value of an upper limit and a lower limit. As an example, here, n is 50. Note, however, that when a value of a force which is corrected force information is 0, even if the corrected force information falls below the lower limit, the corrected force information is not corrected. In addition, a correction of the corrected force information starts from a time point when the corrected force information exceeds the lower limit for the first time.

Force information thus corrected is generated as range-corrected force information by force information range correcting unit 122.

Force information range correcting unit 122 outputs the generated range-corrected force information and time information to force information presenting unit 114.

<Flowchart>

Figure 28:
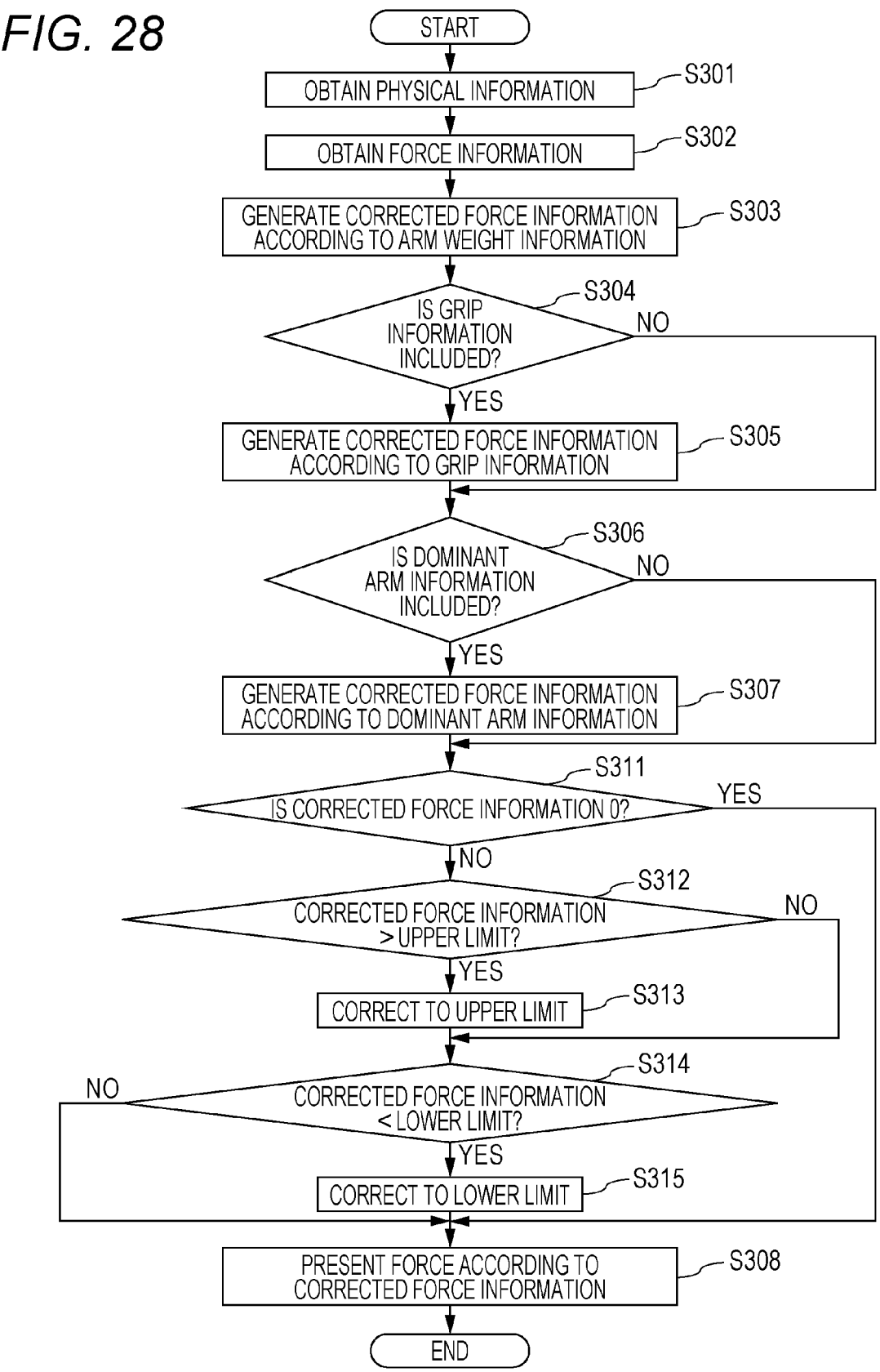
FIG. 28 is a flowchart of a correction procedure of the master-slave robot of the third embodiment of the present disclosure.

A correction procedure of master-slave robot 100C of the third embodiment will be described with reference to a flowchart of FIG. 28.

An example of a manipulation of master-slave robot 100C of the third embodiment is the same as the example of FIG. 22. Here, steps S201 to S206 of the flowchart shown in FIG. 22 will be described with reference to FIG. 28. Of those steps, particularly, a procedure for generating corrected force information by force information correcting unit 113 in step S205 will be described in detail.

First, in step S301, physical information obtaining unit 111 obtains physical information and outputs the physical information to force information correcting unit 113. Processing proceeds to step S302.

Then, in step S302, force information obtaining unit 115 obtains force information and outputs the force information to force information correcting unit 113. Processing proceeds to step S303.

Then, in step S303, force information correcting unit 113 generates, based on the force information obtained from force information obtaining unit 115, corrected force information, using arm weight information included in the physical information which is obtained from physical information obtaining unit 111. Thereafter, processing proceeds to step S304.

Then, in step S304, force information correcting unit 113 determines whether the physical information obtained from physical information obtaining unit 111 includes grip information. If force information correcting unit 113 determines that the physical information includes grip information, processing proceeds to step S305. On the other hand, if force information correcting unit 113 determines that the physical information does not include grip information, processing proceeds to step S306.

Then, in step S305, force information correcting unit 113 generates, based on the previously generated corrected force information, corrected force information again, using the grip information included in the physical information which is obtained from the physical information obtaining unit 111. Thereafter, processing proceeds to step S306.

Then, in step S306, force information correcting unit 113 determines whether the physical information obtained from physical information obtaining unit 111 includes dominant arm information. If force information correcting unit 113 determines that the physical information includes dominant arm information, processing proceeds to step S307. On the other hand, if force information correcting unit 113 determines that the physical information does not include dominant arm information, processing proceeds to step S311.

Then, in step S307, force information correcting unit 113 generates, based on the previously generated corrected force information, corrected force information again, using the dominant arm information included in the physical information which is obtained from physical information obtaining unit 111. Thereafter, processing proceeds to step S311.

Then, in step S311, force information range correcting unit 122 determines whether the corrected force information which is input from force information correcting unit 113 is 0. If force information range correcting unit 122 determines that the corrected force information is 0, processing proceeds to step S308. On the other hand, if force information range correcting unit 122 determines that the corrected force information is not 0, processing proceeds to step S312.

Then, in step S312, force information range correcting unit 122 determines whether the corrected force information which is input from force information correcting unit 113 exceeds an upper limit. If force information range correcting unit 122 determines that the corrected force information exceeds an upper limit, processing proceeds to step S313. On the other hand, if force information range correcting unit 122 determines that the corrected force information does not exceed an upper limit, processing proceeds to step S314.

Then, in step S313, force information range correcting unit 122 generates corrected force information where the corrected force information which is input from force information correcting unit 113 is corrected to the upper limit. Thereafter, processing proceeds to step S314.

Then, in step S314, force information range correcting unit 122 determines whether the corrected force information which is input from force information correcting unit 113 falls below a lower limit. If force information range correcting unit 122 determines that the corrected force information falls below a lower limit, processing proceeds to step S315. On the other hand, if force information range correcting unit 122 determines that the corrected force information does not fall below a lower limit, processing proceeds to step S308.

Then, in step S315, force information range correcting unit 122 generates corrected force information where the corrected force information which is input from force information correcting unit 113 is corrected to the lower limit, and outputs the generated corrected force information to force information presenting unit 114. Thereafter, processing proceeds to step S308.

Then, in step S308, force information presenting unit 114 generates instruction values for master arm mechanism 104B, according to the corrected force information obtained from force information range correcting unit 122, and outputs the generated instruction values to master arm mechanism 104B. Master arm mechanism 104B presents a force based on the instruction values. Thus, the force is presented to operator 1 through master arm mechanism 104B.

Effect of the Third Embodiment

A force correction using an upper limit and a lower limit set for each physical information of an operator is made, and then a force presentation is performed. Thus, operator 1 can perform a task with a force presentation in a range where operator 1 can easily perform the task. As a result, even in a case of different operators 1, efficient tasks can be performed.

Fourth Embodiment

Figure 29:
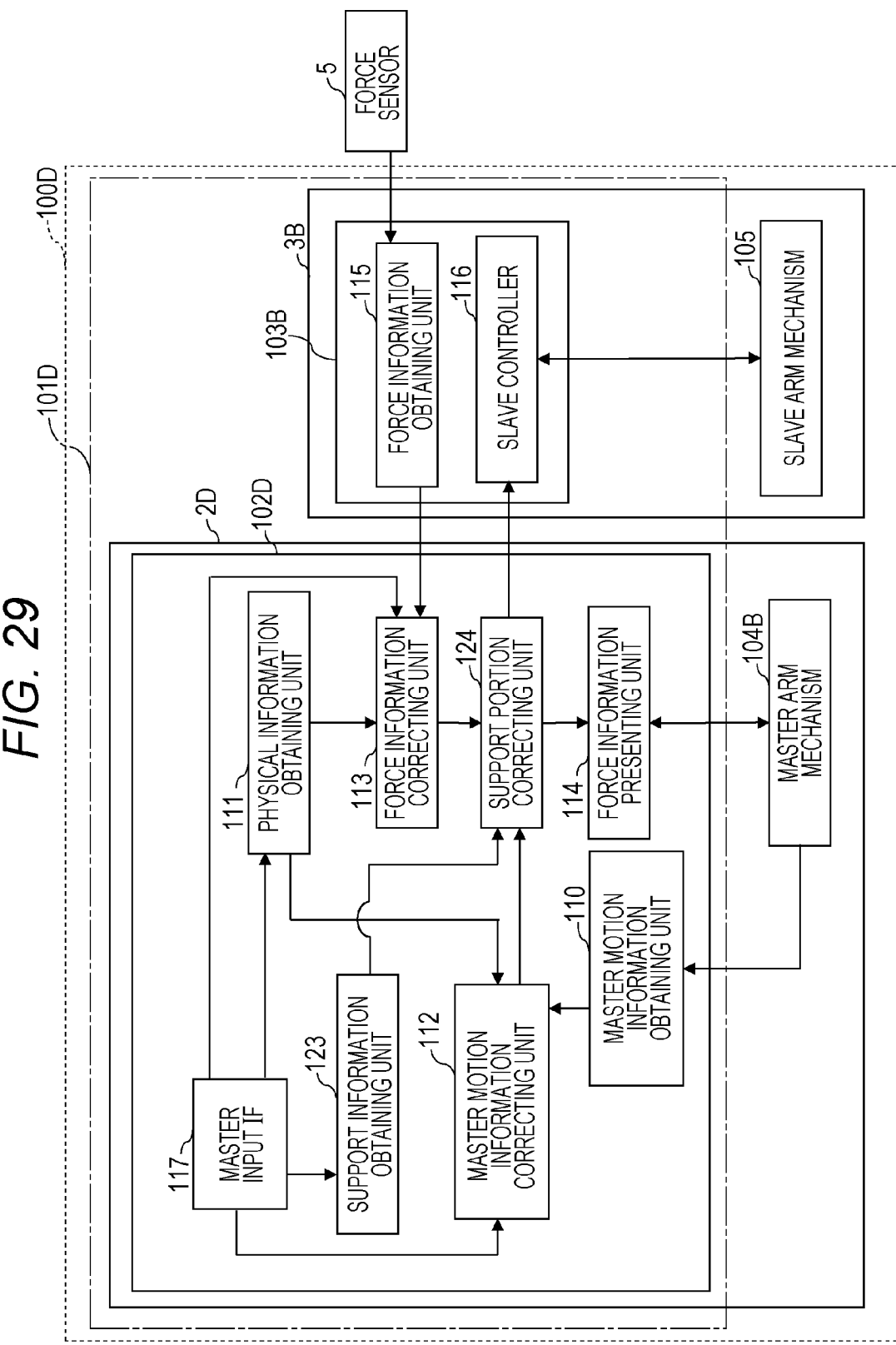
FIG. 29 is a block diagram of a master-slave robot of a fourth embodiment of the present disclosure.

A description will be given of a summary of master-slave robot 100D including control apparatus 101D for master-slave robot 100D of a fourth embodiment of the present disclosure. FIG. 29 is a block diagram of master-slave robot 100D of the fourth embodiment of the present disclosure. Master arm mechanism 104B in master arm 2D, and master motion information obtaining unit 110, physical information obtaining unit 111, master motion information correcting unit 112, force information correcting unit 113, and force information presenting unit 114 which are included in control apparatus 102D for master arm 2D, and slave arm 3B of the fourth embodiment of the present disclosure are the same as those of the second embodiment and thus are denoted by common reference signs. A description of the common portions is omitted and a description will be given below in detail of only portions different from those in the second embodiment (support information obtaining unit 123 and support portion correcting unit 124 which are included in control apparatus 102D for master arm 2D).

(Support Information Obtaining Unit 123)

Figure 30A:
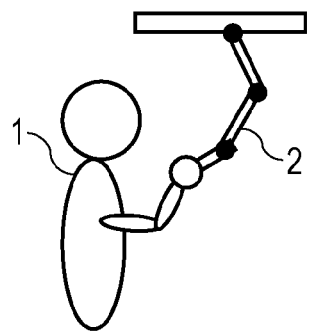
FIG. 30A is an illustrative diagram of a method of fixing an arm in the master-slave robot of the fourth embodiment of the present disclosure.
Figure 30B:
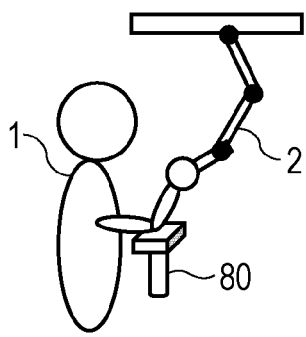
FIG. 30B is an illustrative diagram of a method of fixing the arm in the master-slave robot of the fourth embodiment of the present disclosure.
Figure 30C:
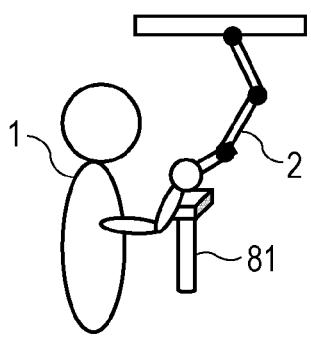
FIG. 30C is an illustrative diagram of a method of fixing the arm in the master-slave robot of the fourth embodiment of the present disclosure.

Support information obtaining unit 123 obtains support information which indicates a method of supporting an arm of operator 1 and which is input from master input IF 117. The support information as used herein is information about a support (fixing) method for supporting the arm of operator 1 by a support portion, which is used when operator 1 grips and manipulates master arm mechanism 104B. FIGS. 30A to 30C are illustrative diagrams of a method of fixing an arm. FIG. 30A shows a case with no fixation of an arm of operator 1. FIG. 30B shows a case with fixation at an arm's elbow of operator 1 (a case in which the elbow is supported on support table 80 which is an example of the support portion). FIG. 30C shows a case with fixation at an arm's wrist of operator 1 (a case in which the wrist is supported on support table 81 which is another example of the support portion). As an example of the support information, "no fixation" is represented by "1", "fixation at the elbow" is represented by "2", and "fixation at the wrist" is represented by "3". Note that in another variant it is also possible to further divide the support portion for the arm of operator 1 into smaller portions.

Operator 1 inputs a method of fixing the arm to support information obtaining unit 123, using master input IF 117. It is also possible to automatically estimate a method of fixing the arm by support information obtaining unit 123, using image recognition, for example.

Support information obtaining unit 123 outputs the obtained support information to support portion correcting unit 124.

(Support Portion Correcting Unit 124)

Master motion information, corrected master motion information, and time information are input to support portion correcting unit 124 from master motion information correcting unit 112. Force information, corrected force information, and time information are input to support portion correcting unit 124 from force information correcting unit 113. Support information is input to support portion correcting unit 124 from support information obtaining unit 123. Support portion correcting unit 124 generates support portion corrected master motion information and support portion corrected force information based on the input corrected master motion information and corrected force information, respectively, and according to the support information.

A description will be given of a method of generating support portion corrected master motion information and support portion corrected force information by support portion correcting unit 124. The closer the support portion is to a hand of operator 1 manipulating master arm mechanism 104B, like "the case with no fixation"→"the case with fixation at the elbow"→"the case with fixation at the wrist", the smaller an amount of correction is. This is because the closer the support portion is to the hand of operator 1, the more firmly master arm mechanism 104B can be gripped, and thus, a difference between operators is small.

A storage unit included in support portion correcting unit 124 stores fixing methods and amounts of correction for the respective fixing methods. Support portion correcting unit 124 calculates an amount of correction, according to obtained support portion information. FIG. 31 shows an example of fixing methods and amounts of correction which are stored in the storage unit. As an example, using the amounts of correction, support portion correcting unit 124 calculates support portion corrected force information. Specifically, when the amount of correction is $\alpha$, information before a correction is $F_b$, and information after the correction is $F_a$, support portion correcting unit 124 calculates support portion corrected force information using $F_b + \alpha \times (F_a - F_b)$. Results corrected based on FIG. 31 are represented by a relationship between time and an amount of movement in FIG. 32A, and are represented by a relationship between time and force in FIG. 32B. It can be seen from FIG. 32A that, for the amount of movement, position information of slave arm mechanism 105 approaches "the case with no fixation" (see "after correction" in FIG. 32A)→"the case with fixation at the elbow" (see "0.6" in FIG. 32A)→"the case with fixation at the wrist" (see "0.2" in FIG. 32A), and information before the correction. In addition, it can be seen from FIG. 32B that, for the force, too, force information presented to master arm mechanism 104B approaches "the case with no fixation" (see "after correction" in FIG. 32B)→"the case with fixation at the elbow" (see "0.6" in FIG. 32B)→"the case with fixation at the wrist" (see "0.2" in FIG. 32B), and information before the correction.

Support portion correcting unit 124 outputs generated support portion corrected master motion information and time information to slave controller 116, and outputs generated support portion corrected force information and time information to force information presenting unit 114.

<Flowchart>

Figure 33:
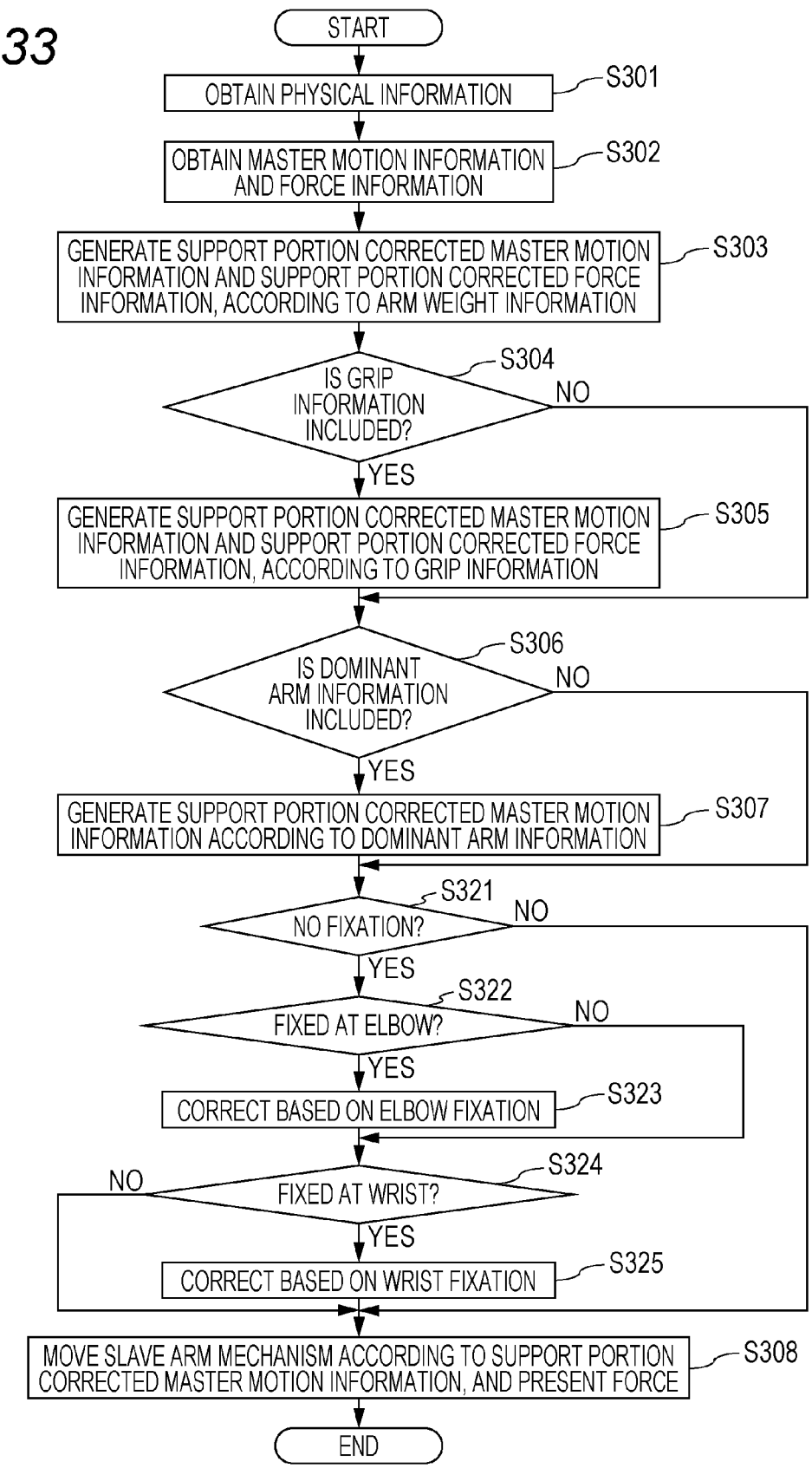
FIG. 33 is a flowchart of a correction procedure of the master-slave robot of the fourth embodiment of the present disclosure.

A correction procedure of master-slave robot 100D of the fourth embodiment will be described with reference to a flowchart of FIG. 33.

An example of a manipulation of master-slave robot 100D of the fourth embodiment is the same as the example of FIG. 22. Here, steps S201 to S206 of the flowchart shown in FIG. 22 will be described with reference to FIG. 33. Of those steps, particularly, a description will be given in detail of a procedure for generating support portion corrected master motion information by master motion information correcting unit 112 in step S202 and a procedure for generating support portion corrected force information by force information correcting unit 113 in step S205.

First, in step S301, physical information obtaining unit 111 obtains physical information and outputs the physical information to master motion information correcting unit 112 and force information correcting unit 113. Processing proceeds to step S302.

Then, in step S302, master motion information obtaining unit 110 obtains master motion information and outputs the master motion information to master motion information correcting unit 112, and force information obtaining unit 115 obtains force information and outputs the force information to force information correcting unit 113. Processing proceeds to step S303.

Then, in step S303, master motion information correcting unit 112 generates, based on the master motion information, support portion corrected master motion information, using arm weight information included in the physical information. In addition, force information correcting unit 113 generates, based on the force information, support portion corrected force information, using the arm weight information included in the physical information. Thereafter, processing proceeds to step S304.

Then, in step S304, master motion information correcting unit 112 and force information correcting unit 113 determine independently of each other whether the physical information includes grip information. If each of master motion information correcting unit 112 and force information correcting unit 113 determines that the physical information includes grip information, processing proceeds to step S305. On the other hand, if each of master motion information correcting unit 112 and force information correcting unit 113 determines that the physical information does not include grip information, processing proceeds to step S306. The determinations by master motion information correcting unit 112 and force information correcting unit 113 are made independently of each other.

Then, in step S305, master motion information correcting unit 112 generates, based on the previously generated support portion corrected master motion information, support portion corrected master motion information again, using the grip information included in the physical information. In addition, force information correcting unit 113 generates, based on the previously generated support portion corrected force information, support portion corrected force information again, using the grip information included in the physical information. Thereafter, processing proceeds to step S306.

Then, in step S306, master motion information correcting unit 112 and force information correcting unit 113 determine independently of each other whether the physical information includes dominant arm information. If each of master motion information correcting unit 112 and force information correcting unit 113 determines that the physical information includes dominant arm information, processing proceeds to step S307. On the other hand, if each of master motion information correcting unit 112 and force information correcting unit 113 determines that the physical information does not include dominant arm information, processing proceeds to step S321.

Then, in step S307, master motion information correcting unit 112 generates, based on the previously generated support portion corrected master motion information, support portion corrected master motion information again, using the dominant arm information included in the physical information, and outputs the generated support portion corrected master motion information to support portion correcting unit 124. In addition, force information correcting unit 113 generates, based on the previously generated support portion corrected force information, support portion corrected force information again, using the dominant arm information included in the physical information, and outputs the generated support portion corrected force information to support portion correcting unit 124. Thereafter, processing proceeds to step S321.

Then, in step S321, support portion correcting unit 124 determines, from support information which is input from support information obtaining unit 123, whether there is no fixation. If support portion correcting unit 124 determines that there is no fixation, processing proceeds to step S308. On the other hand, if support portion correcting unit 124 determines that there is fixation, processing proceeds to step S322.

Then, in step S322, support portion correcting unit 124 determines, from the support information which is input from support information obtaining unit 123, whether there is fixation at an elbow. If support portion correcting unit 124 determines that there is fixation at an elbow, processing proceeds to step S323. On the other hand, if support portion correcting unit 124 determines that there is no fixation at an elbow, processing proceeds to step S324.

Then, in step S323, support portion correcting unit 124 generates support portion corrected force information where the previously generated support portion corrected force information is corrected based on the elbow fixation. Thereafter, processing proceeds to step S324.

Then, in step S324, support portion correcting unit 124 determines whether the input support information indicates fixation at a wrist. If support portion correcting unit 124 determines that there is fixation at a wrist, processing proceeds to step S325. On the other hand, if support portion correcting unit 124 determines that there is no fixation at a wrist, processing proceeds to step S308.

Then, in step S325, support portion correcting unit 124 generates support portion corrected force information where the previously generated support portion corrected force information is corrected based on the wrist fixation, and outputs the support portion corrected force information to force information presenting unit 114. Thereafter, processing proceeds to step S308.

Then, in step S308, slave controller 116 generates instruction values for slave arm mechanism 105, according to the support portion corrected master motion information obtained from support portion correcting unit 124, and outputs the generated instruction values to slave arm mechanism 105. Slave arm mechanism 105 is allowed to move based on the instruction values to perform a task. On the other hand, force information presenting unit 114 generates instruction values for master arm mechanism 104B, according to the support portion corrected force information obtained from support portion correcting unit 124, and outputs the generated instruction values to master arm mechanism 104B. Master arm mechanism 104B presents a force based on the instruction values. Thus, the force is presented to operator 1 through master arm mechanism 104B.

Effect of the Fourth Embodiment

Master motion information and force information are corrected based on information on a method of fixing an arm of operator 1, and then a task and a force presentation are performed. Thus, even in a case of different postures of operator 1 upon manipulations, variations in quality and efficiency can be overcome.

Fifth Embodiment

Figure 34:
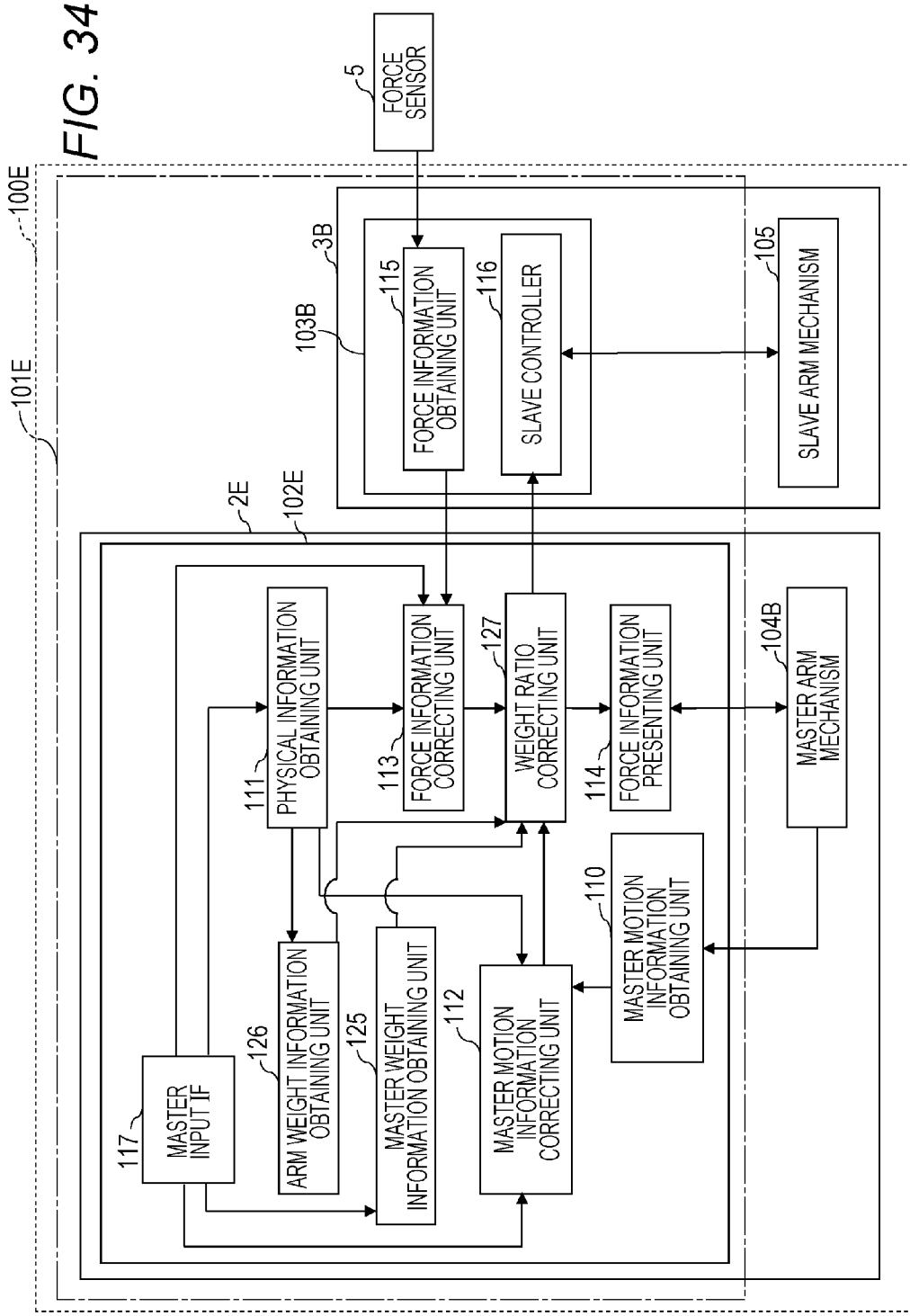
FIG. 34 is a block diagram of a master-slave robot of a fifth embodiment of the present disclosure.

A description will be given of a summary of master-slave robot 100E including control apparatus 101E for master-slave robot 100E of a fifth embodiment of the present disclosure. FIG. 34 is a block diagram of master-slave robot 100E of the fifth embodiment of the present disclosure. Master arm mechanism 104B in master arm 2E, and master motion information obtaining unit 110, physical information obtaining unit 111, master motion information correcting unit 112, force information correcting unit 113, force information presenting unit 114, and master input IF 117 which are included in control apparatus 102E for master arm 2E, and slave arm 3B of the fifth embodiment of the present disclosure are the same as those of the second embodiment and thus are denoted by common reference signs. A description of the common portions is omitted and a description will be given below in detail of only portions different from those in the second embodiment (master weight information obtaining unit 125, arm weight information obtaining unit 126, and weight ratio correcting unit 127 which are included in control apparatus 102E for master arm 2E).

(Master Weight Information Obtaining Unit 125)

Master weight information obtaining unit 125 obtains master weight information which is weight information of master arm mechanism 104B and which is input from master input IF 117. A value obtained by measuring a weight of master arm mechanism 104B is input as master weight information to master weight information obtaining unit 125 using master input IF 117. Thus, master weight information obtaining unit 125 obtains the master weight information. For example, the value is 0.3 kg. In addition, there is a method of calculating a weight of master arm mechanism 104B by measuring inertia. Master weight information obtaining unit 125 outputs the obtained master weight information to weight ratio correcting unit 127.

(Arm Weight Information Obtaining Unit 126)

Physical information is input to arm weight information obtaining unit 126 from physical information obtaining unit 111. Arm weight information obtaining unit 126 obtains arm weight information of operator 1 from the physical information. For example, the arm weight information is a value such as 4.5 kg. Arm weight information obtaining unit 126 outputs the obtained arm weight information to weight ratio correcting unit 127.

(Weight Ratio Correcting Unit 127)

Master motion information, corrected master motion information, and time information are input to weight ratio correcting unit 127 from master motion information correcting unit 112. Force information, corrected force information, and time information are input to weight ratio correcting unit 127 from force information correcting unit 113. Master weight information is input to weight ratio correcting unit 127 from master weight information obtaining unit 125. Arm weight information is input to weight ratio correcting unit 127 from arm weight information obtaining unit 126. Weight ratio correcting unit 127 generates weight ratio corrected master motion information and weight ratio corrected force information from the input corrected master motion information and corrected force information, respectively, according to a ratio between the master weight information and the arm weight information.

First, a description will be given of a method of calculating weight ratio information of arm weight information with respect to master weight information by weight ratio correcting unit 127. Weight ratio correcting unit 127 calculates, as weight ratio information, a ratio with master weight information in a denominator and arm weight information in a numerator.

Next, a description will be given of a method of generating weight ratio corrected master motion information and weight ratio corrected force information by weight ratio correcting unit 127. The larger the ratio of an arm weight of operator 1 to a weight of master arm mechanism 104B, the larger the influence exerted by a difference in the arm weight of operator 1, and thus, weight ratio correcting unit 127 increases an amount of correction. That is, the larger the weight ratio information, the larger the amount of correction.

A storage unit included in weight ratio correcting unit 127 stores weight ratio information and amounts of correction for the respective weight ratio information. Weight ratio correcting unit 127 calculates an amount of correction, according to calculated weight ratio information. FIG. 35 shows an example of weight ratio information and amounts of correction which are stored in the storage unit. As an example, using the amounts of correction, weight ratio correcting unit 127 calculates weight ratio corrected information. When the amount of correction is $\alpha$, information before a correction is $F_b$, and information after the correction is $F_a$, weight ratio correcting unit 127 calculates weight ratio corrected information using $F_b + \alpha \times (F_a - F_b)$.

Weight ratio correcting unit 127 outputs generated weight ratio corrected master motion information and time information to slave controller 116, and outputs generated weight ratio corrected force information and time information to force information presenting unit 114.

<Flowchart>

Figure 36:
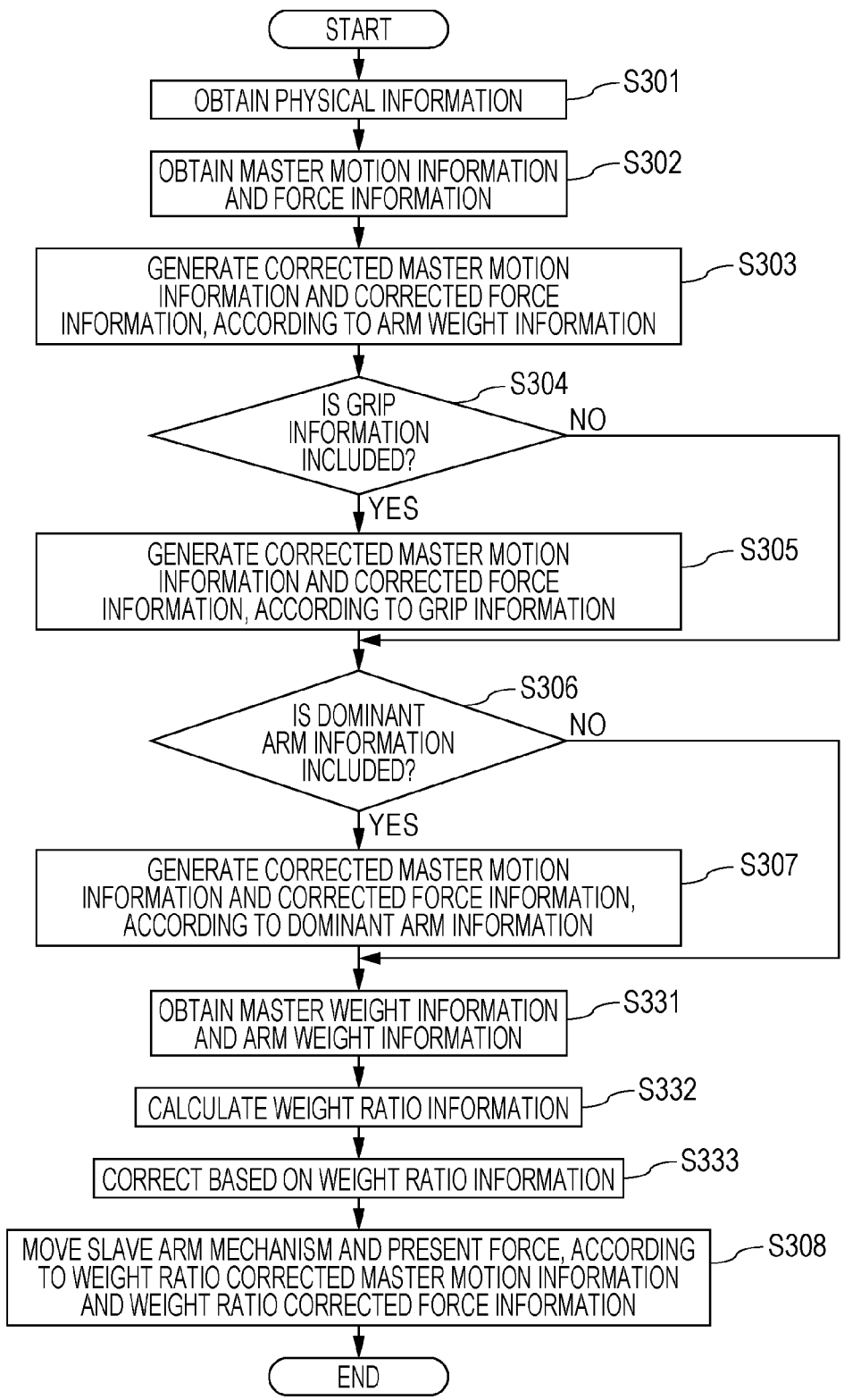
FIG. 36 is a flowchart of a correction procedure of the master-slave robot of the fifth embodiment of the present disclosure.

A correction procedure of master-slave robot 100E of the fifth embodiment will be described with reference to a flowchart of FIG. 36.

An example of a manipulation of master-slave robot 100E of the fifth embodiment is the same as the example of FIG. 22. Here, steps S201 to S206 of the flowchart shown in FIG. 22 will be described with reference to FIG. 36. Of those steps, particularly, a description will be given in detail of a procedure for generating corrected master motion information by master motion information correcting unit 112 in step S202 and a procedure for generating corrected force information by force information correcting unit 113 in step S205.

First, in step S301, physical information obtaining unit 111 obtains physical information and outputs the physical information to force information correcting unit 113 and arm weight information obtaining unit 126. Processing proceeds to step S302.

Then, in step S302, master motion information obtaining unit 110 obtains master motion information and outputs the master motion information to master motion information correcting unit 112, and force information obtaining unit 115 obtains force information and outputs the force information to force information correcting unit 113. Processing proceeds to step S303.

Then, in step S303, master motion information correcting unit 112 generates, based on the master motion information obtained from master motion information obtaining unit 110, corrected master motion information, using arm weight information included in the physical information which is obtained from physical information obtaining unit 111. In addition, force information correcting unit 113 generates, based on the force information obtained from force information obtaining unit 115, corrected force information, using the arm weight information included in the physical information which is obtained from physical information obtaining unit 111. Thereafter, processing proceeds to step S304.

Then, in step S304, master motion information correcting unit 112 and force information correcting unit 113 determine independently of each other whether the physical information obtained from physical information obtaining unit 111 includes grip information. If each of master motion information correcting unit 112 and force information correcting unit 113 determines that the physical information includes grip information, processing proceeds to step S305. On the other hand, if each of master motion information correcting unit 112 and force information correcting unit 113 determines that the physical information does not include grip information, processing proceeds to step S306. The determinations by master motion information correcting unit 112 and force information correcting unit 113 are made independently of each other.

Then, in step S305, master motion information correcting unit 112 generates, based on the previously generated corrected master motion information, corrected master motion information again, using the grip information included in the physical information. In addition, force information correcting unit 113 generates, based on the previously generated corrected force information, corrected force information again, using the grip information included in the physical information. Thereafter, processing proceeds to step S306.

Then, in step S306, master motion information correcting unit 112 and force information correcting unit 113 determine independently of each other whether the physical information includes dominant arm information. If each of master motion information correcting unit 112 and force information correcting unit 113 determines that the physical information includes dominant arm information, processing proceeds to step S307. On the other hand, if each of master motion information correcting unit 112 and force information correcting unit 113 determines that the physical information does not include dominant arm information, processing proceeds to step S331.

Then, in step S307, master motion information correcting unit 112 generates, based on the previously generated corrected master motion information, corrected master motion information again, using the dominant arm information included in the physical information, and outputs the generated corrected master motion information to weight ratio correcting unit 127. In addition, force information correcting unit 113 generates, based on the previously generated corrected force information, corrected force information again, using the dominant arm information included in the physical information, and outputs the generated corrected force information to weight ratio correcting unit 127. Processing proceeds to step S331.

Then, in step S331, master weight information obtaining unit 125 obtains master weight information, and arm weight information obtaining unit 126 obtains arm weight information. Processing proceeds to step S332.

Then, in step S332, weight ratio correcting unit 127 calculates weight ratio information using the master weight information and the arm weight information. Processing proceeds to step S333.

Then, in step S333, weight ratio correcting unit 127 generates weight ratio corrected master information and weight ratio corrected force information where the input corrected master motion information and corrected force information are corrected based on the calculated weight ratio information. Processing proceeds to step S308.

Then, in step S308, slave controller 116 generates instruction values for slave arm mechanism 105, according to the weight ratio corrected master motion information obtained from weight ratio correcting unit 127, and outputs the generated instruction values to slave arm mechanism 105. Slave arm mechanism 105 is allowed to move based on the instruction values to perform a task. On the other hand, force information presenting unit 114 generates instruction values for master arm mechanism 104B, according to the weight ratio corrected force information obtained from weight ratio correcting unit 127, and outputs the generated instruction values to master arm mechanism 104B. Master arm mechanism 104B presents a force based on the instruction values. Thus, the force is presented to operator 1 through master arm mechanism 104B.

Effect of the Fifth Embodiment

Master motion information and force information are corrected based on a weight of an arm of operator 1 and further on a weight of master arm mechanism 104B, and then a task and a force presentation are performed. Thus, even in a case of different master arm mechanisms 104B manipulated by operator 1, variations in quality and efficiency can be overcome.

Sixth Embodiment

Figure 37:
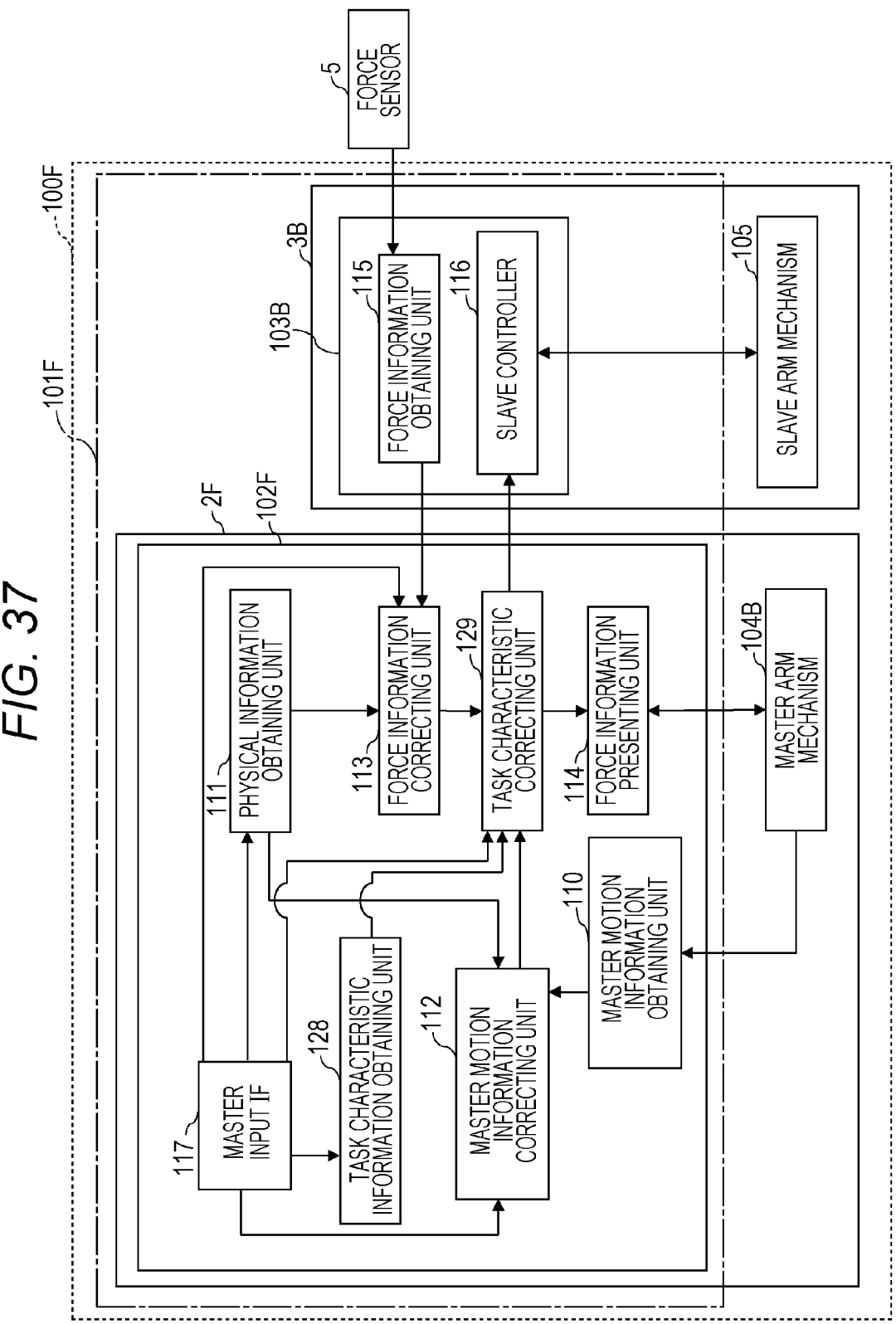
FIG. 37 is a block diagram of a master-slave robot of a sixth embodiment of the present disclosure.

A description will be given of a summary of master-slave robot 100F including control apparatus 101F for master-slave robot 100F of a sixth embodiment of the present disclosure. FIG. 37 is a block diagram of master-slave robot 100F of the sixth embodiment of the present disclosure. Master arm mechanism 104B in master arm 2F, and master motion information obtaining unit 110, physical information obtaining unit 111, master motion information correcting unit 112, force information correcting unit 113, force information presenting unit 114, and master input IF 117 which are included in control apparatus 102F for master arm 2F, and slave arm 3B of the sixth embodiment of the present disclosure are the same as those of the second embodiment and thus are denoted by common reference signs. A description of the common portions is omitted and a description will be given below in detail of only portions different from those in the second embodiment (task characteristic information obtaining unit 128 and task characteristic correcting unit 129 which are included in control apparatus 102F for master arm 2F).

(Task Characteristic Information Obtaining Unit 128)

Task characteristic information obtaining unit 128 obtains task characteristic information which is information on characteristics of a task and which is input from master input IF 117. The task characteristic information as used herein is of two types and is at least one or more information including direction information indicating a direction in which master arm mechanism 104B moves and enlargement factor information indicating an enlargement factor of imaging apparatus 6 which is used when imaging apparatus 6 captures video of an object for a task, for example, in an enlarged manner. The enlargement factor is represented by the following mathematical formula:

(enlargement factor)=(size of the object displayed on the display)/(real size of the object)

The direction information indicates an amount of movement to each direction and posture of master arm mechanism 104B manipulated by operator 1. Depending on a task, it is also possible for operator 1 to specify, using master input IF 117, the most important direction, such as a direction in which an object is inserted, as direction information. FIG. 38 shows an example of direction information.

The enlargement factor information indicates an enlargement factor used when imaging apparatus 6 captures video. For example, a value such as 5.0× is obtained.

Figure 39:
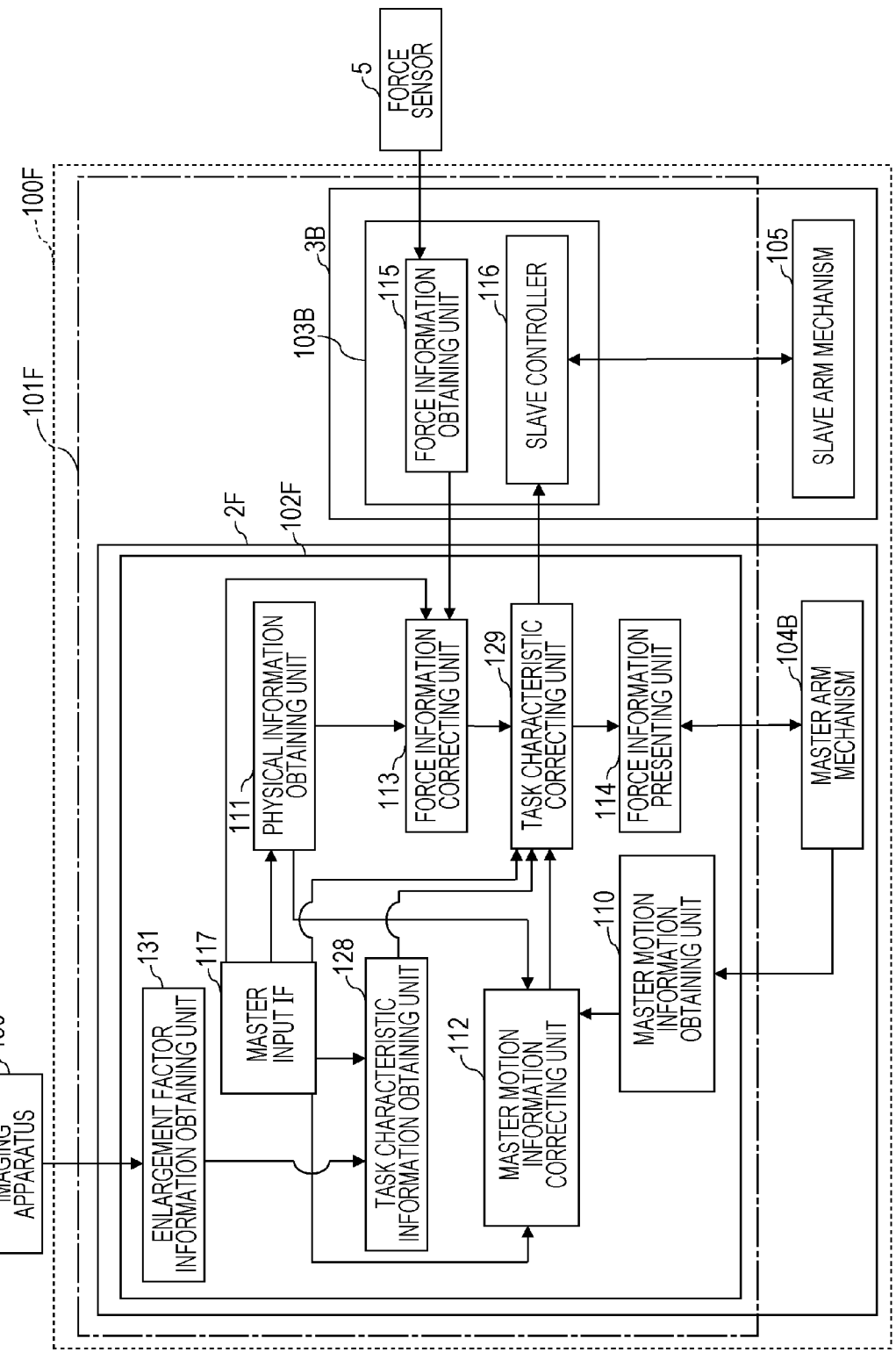
FIG. 39 is a block diagram of the master-slave robot of the sixth embodiment of the present disclosure (for a case of using an enlargement factor information obtaining unit)

In addition, for the enlargement factor information, in addition to a method in which, as shown in FIG. 37, task characteristic information obtaining unit 128 obtains a value which is input by operator 1 through master input IF 117, there is a method in which enlargement factor information of imaging apparatus 130 is obtained using enlargement factor information obtaining unit 131. Such a variant is shown in a block diagram of FIG. 39. In FIG. 39, enlargement factor information obtaining unit 131 obtains enlargement factor information of imaging apparatus 130 and outputs the obtained enlargement factor information as task characteristic information to task characteristic information obtaining unit 128.

Task characteristic information obtaining unit 128 outputs the obtained task characteristic information to task characteristic correcting unit 129.

(Task Characteristic Correcting Unit 129)

Corrected master motion information and time information are input to task characteristic correcting unit 129 from master motion information correcting unit 112. Corrected force information and time information are input to task characteristic correcting unit 129 from force information correcting unit 113. Task characteristic information is input to task characteristic correcting unit 129 from task characteristic information obtaining unit 128. Task characteristic correcting unit 129 generates task characteristic corrected master motion information and task characteristic corrected force information from the input corrected master motion information and corrected force information, respectively, according to the task characteristic information.

First, a description will be given of a method of generating, by task characteristic correcting unit 129, task characteristic corrected master motion information and task characteristic corrected force information according to direction information. Task characteristic correcting unit 129 makes a correction based on direction information such that a direction in which master arm mechanism 104B moves a larger amount has a larger amount of correction. The correction is thus made because, since the direction in which master arm mechanism 104B moves a larger amount is an important direction in a task, task characteristic correcting unit 129 increases an amount of correction so as to emphasize the direction. It is also possible for task characteristic correcting unit 129 to increase an amount of correction of a direction specified by task characteristic obtaining unit 128. A storage unit included in task characteristic correcting unit 129 stores direction information and amounts of correction for the respective direction information. Task characteristic correcting unit 129 calculates an amount of correction, according to obtained direction information. FIG. 40 shows an example of direction information and amounts of correction which are stored in the storage unit. As an example, using the amounts of correction, task characteristic correcting unit 129 calculates task characteristic corrected information. When the amount of correction is α and information after a correction is $F_a$, task characteristic correcting unit 129 calculates task characteristic corrected information using $\alpha \times F_a$.

Specifically, the force information is composed of a master arm movement direction component amount which is along movement direction of the master arm, a master arm first perpendicular direction component amount along a first direction which is perpendicular to the movement direction of the master arm, and a master arm second perpendicular direction component amount along a second direction which is perpendicular to the movement direction of the master arm. Needless to say, the first direction and the second direction are perpendicular to each other. Task characteristic correcting unit 129 corrects the force information in such a manner that the master arm movement direction is larger. The master arm first perpendicular component amount and the master arm second perpendicular component amount are remained unchanged. The force information presenting unit presents the force to the arm of the operator through the master arm, based on the force information corrected by the task characteristic correcting unit. Since the direction in which master arm mechanism 104B moves a larger amount (i.e., the movement direction of the master arm) is an important direction in a task, the direction is emphasized in the fifth embodiment.

Figure 41A:
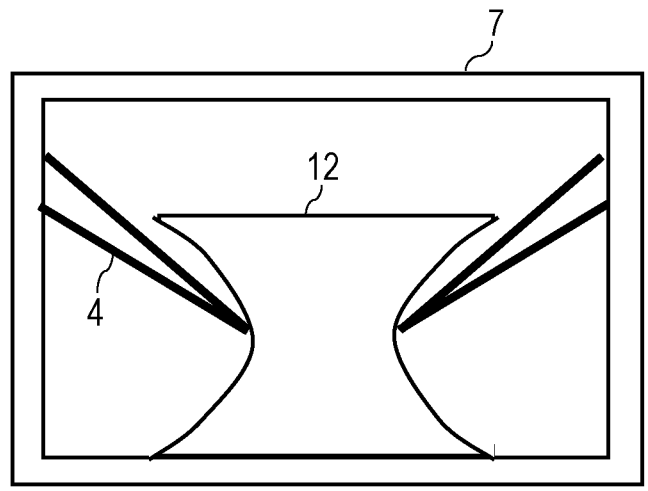
FIG. 41A is an illustrative diagram of a case of an increase in enlargement factor information in the master-slave robot of the sixth embodiment of the present disclosure.
Figure 41B:
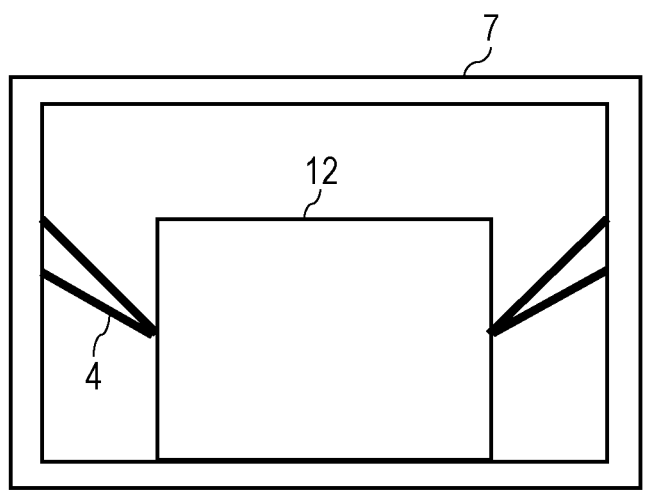
FIG. 41B is an illustrative diagram of a case of an increase in enlargement factor information in the master-slave robot of the sixth embodiment of the present disclosure.

Next, a description will be given of a method of generating, by task characteristic correcting unit 129, task characteristic corrected master motion information and task characteristic corrected force information according to enlargement factor information. When an object is a flexible material, task characteristic correcting unit 129 makes a correction based on enlargement factor information such that the larger the enlargement factor information, the larger the amount of correction of corrected master motion information and the smaller the amount of correction of corrected force information. When the object is a rigid material, task characteristic correcting unit 129 makes a correction based on enlargement factor information such that the larger the enlargement factor information, the smaller the amount of correction of corrected master motion information and the larger the amount of correction of corrected force information. The corrections are thus made for a following reason. Specifically, when the object is a flexible material, if enlargement factor information is large, the object looks enlarged to operator 1, as shown in FIG. 41A. Hence, deformation of the object looks large to operator 1. Accordingly, operator 1 thinks that he/she is applying a large force to the object. As a result, operator 1 can only apply a smaller force than a force of a magnitude required for a task, to master arm mechanism 104B and thus cannot properly complete the task. Hence, in order to induce operator 1 to apply a force required for a task of moving master arm mechanism 104B a large amount to master arm mechanism 104B, task characteristic correcting unit 129 increases an amount of correction of corrected master motion information and reduces an amount of correction of corrected force information. When the object is a rigid material, if enlargement factor information is large, the object looks enlarged, as shown in FIG. 41B. Hence, the object looks large and accordingly operator 1 thinks that the object is heavy and hard. This phenomenon is called Charpentier effect. Due to such a phenomenon, operator 1 recognizes a large object as a heavy object. As a result, operator 1 applies a large force to the object, resulting in application of a force more than necessary to the object. Hence, in order to induce operator 1 to apply only a force required for a task of moving master arm mechanism 104B a small amount to master arm mechanism 104B, task characteristic correcting unit 129 reduces an amount of correction of corrected master motion information and increases an amount of correction of corrected force information. For specification of the object as a flexible material or a rigid material, operator 1 can input such information to task characteristic correcting unit 129 using master input IF 117.

The storage unit included in task characteristic correcting unit 129 stores enlargement factor information and amounts of correction for the respective enlargement factor information. Task characteristic correcting unit 129 calculates an amount of correction, according to enlargement factor information obtained from task characteristic information obtaining unit 128 and information indicating as to whether the object is a flexible material or a rigid material. FIG. 42 shows an example of enlargement factor information and amounts of correction which are stored in the storage unit. As an example, using the amounts of correction, task characteristic correcting unit 129 calculates task characteristic corrected information. When the amount of correction is $\alpha$ and information after a correction is $F_a$, task characteristic correcting unit 129 calculates task characteristic corrected information using $\alpha \times F_a$.

Task characteristic correcting unit 129 outputs generated task characteristic corrected master motion information and time information to slave controller 116, and outputs generated task characteristic corrected force information and time information to force information presenting unit 114.

<Flowchart>

A correction procedure of master-slave robot 100F of the sixth embodiment will be described with reference to a flowchart of FIG. 43.

An example of a manipulation of master-slave robot 100F of the sixth embodiment is the same as the example of FIG. 22. Here, steps S201 to S206 of the flowchart shown in FIG. 22 will be described with reference to FIG. 43. Of those steps, particularly, a description will be given in detail of a procedure for generating corrected master motion information by master motion information correcting unit 112 in step S202 and a procedure for generating corrected force information by force information correcting unit 113 in step S205.

First, in step S301, physical information obtaining unit 111 obtains physical information and outputs the physical information to force information correcting unit 113 and master motion information correcting unit 112. Processing proceeds to step S302.

Then, in step S302, master motion information obtaining unit 110 obtains master motion information and outputs the master motion information to master motion information correcting unit 112, and force information obtaining unit 115 obtains force information and outputs the force information to force information correcting unit 113. Processing proceeds to step S303.

Then, in step S303, master motion information correcting unit 112 generates, based on the master motion information obtained from master motion information obtaining unit 110, corrected master motion information, using arm weight information included in the physical information which is obtained from physical information obtaining unit 111. In addition, force information correcting unit 113 generates, based on the force information obtained from force information obtaining unit 115, corrected force information, using the arm weight information included in the physical information which is obtained from physical information obtaining unit 111. Thereafter, processing proceeds to step S304.

Then, in step S304, master motion information correcting unit 112 and force information correcting unit 113 determine independently of each other whether the physical information obtained from physical information obtaining unit 111 includes grip information. If each of master motion information correcting unit 112 and force information correcting unit 113 determines that the physical information includes grip information, processing proceeds to step S305. On the other hand, if each of master motion information correcting unit 112 and force information correcting unit 113 determines that the physical information does not include grip information, processing proceeds to step S306. The determinations by master motion information correcting unit 112 and force information correcting unit 113 are made independently of each other.

Then, in step S305, master motion information correcting unit 112 generates, based on the previously generated corrected master motion information, corrected master motion information again, using the grip information included in the physical information. In addition, force information correcting unit 113 generates, based on the previously generated corrected force information, corrected force information again, using the grip information included in the physical information. Thereafter, processing proceeds to step S306.

Then, in step S306, master motion information correcting unit 112 and force information correcting unit 113 determine independently of each other whether the physical information includes dominant arm information. If each of master motion information correcting unit 112 and force information correcting unit 113 determines that the physical information includes dominant arm information, processing proceeds to step S307. On the other hand, if each of master motion information correcting unit 112 and force information correcting unit 113 determines that the physical information does not include dominant arm information, processing proceeds to step S341.

Then, in step S307, master motion information correcting unit 112 generates, based on the previously generated corrected master motion information, corrected master motion information again, using the dominant arm information included in the physical information, and outputs the generated corrected master motion information to task characteristic correcting unit 129. In addition, force information correcting unit 113 generates, based on the previously generated corrected force information, corrected force information again, using the dominant arm information included in the physical information, and outputs the generated corrected force information to task characteristic correcting unit 129. Processing proceeds to step S341.

Then, in step S341, task characteristic correcting unit 129 determines whether task characteristic information obtained from task characteristic information obtaining unit 128 includes direction information. If task characteristic correcting unit 129 determines that task characteristic information includes direction information, processing proceeds to step S342. On the other hand, if task characteristic correcting unit 129 determines that task characteristic information does not include direction information, processing proceeds to step S343.

Then, in step S342, task characteristic correcting unit 129 generates task characteristic corrected master motion information and task characteristic corrected force information where the input corrected master motion information and corrected force information are corrected based on the direction information. Thereafter, processing proceeds to step S343.

Then, in step S343, task characteristic correcting unit 129 determines whether the task characteristic information obtained from task characteristic information obtaining unit 128 includes enlargement factor information. If task characteristic correcting unit 129 determines that the task characteristic information includes enlargement factor information, processing proceeds to step S344. On the other hand, if task characteristic correcting unit 129 determines that the task characteristic information does not include enlargement factor information, processing proceeds to step S308.

Then, in step S344, task characteristic correcting unit 129 determines, based on information which is input to task characteristic correcting unit 129 by operator 1 using master input IF 117, whether an object is a flexible material or a rigid material. If task characteristic correcting unit 129 determines that an object is a flexible material, processing proceeds to step S345. On the other hand, if task characteristic correcting unit 129 determines that an object is a rigid material, processing proceeds to step S346.

Then, in step S345, task characteristic correcting unit 129 generates task characteristic corrected master motion information and task characteristic corrected force information where the input corrected master motion information and corrected force information are corrected based on the enlargement factor information of the flexible material. Thereafter, processing proceeds to step S308.

Then, in step S346, task characteristic correcting unit 129 generates task characteristic corrected master motion information and task characteristic corrected force information where the input corrected master motion information and corrected force information are corrected based on the enlargement factor information of the rigid material. Thereafter, processing proceeds to step S308.

Then, in step S308, slave controller 116 generates instruction values for slave arm mechanism 105, according to the task characteristic corrected master motion information obtained from task characteristic correcting unit 129, and outputs the generated instruction values to slave arm mechanism 105. Slave arm mechanism 105 is allowed to move based on the instruction values to perform a task. On the other hand, force information presenting unit 114 generates instruction values for master arm mechanism 104B, according to the task characteristic corrected force information obtained from task characteristic correcting unit 129, and outputs the generated instruction values to master arm mechanism 104B. Master arm mechanism 104B presents a force based on the instruction values. Thus, the force is presented to operator 1 through master arm mechanism 104B.

Effect of the Sixth Embodiment

Master motion information and force information are corrected based on a direction of a task or an enlargement factor of the imaging apparatus, and then the task and a force presentation are performed. Thus, even in a case of different conditions where a task is performed, variations in quality and efficiency can be overcome.

Note that the present disclosure is not limited to the above-described embodiments and can be implemented in various other modes.

For example, each component of a control apparatus in the present disclosure can be configured by either one of master arm 2 and slave arm 3.

Note that, for a master motion information correcting unit and a force information correcting unit of a control apparatus in the present disclosure, amounts of correction can be changed according to content of a task. For example, in a case of a rough movement task that does not involve a contact, the amounts of correction are increased. In a case of a fine task that involves a contact, the amounts of correction are reduced. Operator 1 can input content of a task using master input IF 117. A storage unit included in each correcting unit stores a relationship between content of tasks and amounts of correction. When content of a task is input, a corresponding amount of correction is obtained. By multiplying the amount of correction for the content of the task which is calculated in this manner by an amount of correction calculated from an arm weight of operator 1, an amount of correction is calculated. By thus calculating an amount of correction taking into account content of a task, an amount of correction is reduced for a task that requires careful manipulations, making it easier to perform a fine task; on the other hand, an amount of correction is increased for a task that does not require careful manipulations, improving a speed of the task.

Note that although the present disclosure is described based on the first to sixth embodiments and the variants, needless to say, the present disclosure is not limited to the first to sixth embodiments and the variants. The present disclosure also includes cases such as those shown below.

A part or all of each of the above-described control apparatuses is specifically a computer system including a microprocessor, a ROM, a RAM, a hard disk unit, a display unit, a keyboard, a mouse, and the like. The RAM or hard disk unit stores a computer program. By the microprocessor operating according to the computer program, each unit achieves its function. Here, the computer program includes a combination of a plurality of instruction codes indicating instructions to a computer, to achieve predetermined functions.

For example, a program executing unit such as a CPU reads and executes a software program recorded in a recording medium such as a hard disk or a semiconductor memory. Thus, each component can be implemented. Note that software that implements some or all of components included in a control apparatus of the embodiments or the variants is a program such as that shown below. Specifically, the program is a control program for a master-slave robot including a slave arm that performs a task using a slave arm mechanism; and a master arm that has a master arm mechanism and that is remotely manipulated by an operator to allow the slave arm mechanism to make a motion, the control program causing a computer to function as:

a master motion information obtaining unit that obtains at least one or more pieces of master motion information including a position, a posture, a speed, and an angular velocity of the master arm mechanism;

a physical information obtaining unit that obtains physical information of the operator, the physical information including an arm weight of the operator;

a master motion information correcting unit that generates corrected master motion information where an amount of correction of the master motion information obtained from the master motion information obtaining unit is corrected such that heavier the arm weight of the operator included in the physical information, larger a movement of the slave arm, the physical information being obtained from the physical information obtaining unit; and a slave controller that controls the slave arm mechanism, according to the corrected master motion information obtained from the master motion information correcting unit.

In addition, the program may be executed by downloading the program from a server or the like, or may be executed by reading a program recorded in a predetermined recording medium (e.g., an optical disk such as a CD-ROM, a magnetic disk, or a semiconductor memory).

In addition, a number of computers that execute the program may be one or at least two. In other words, centralized processing may be performed or distributed processing may be performed.

Note that by combining any of the above-described various embodiments or variants as appropriate, effects brought about by the embodiments or variants can be provided.

INDUSTRIAL APPLICABILITY

Control apparatuses and control methods for master-slave robots, master-slave robots, control programs for master-slave robots, and integrated electronic circuits for controlling master-slave robots in the present disclosure can perform manipulations according to an arm weight of an operator, and are useful as control apparatuses and control methods for industrial, household, or medical master-slave robots, industrial, household, or medical master-slave robots, control programs for industrial, household, or medical master-slave robots, and integrated electronic circuits for controlling industrial, household, or medical master-slave robots.

REFERENCE SIGNS LIST

1 operator (person)
2, 2B, 2C, 2D, 2E, and 2F master arm
3 and 3B slave arm
4 hand
5 force sensor
6 imaging apparatus
7 display
8 fine part
80 support table
81 support table
9 insertion opening (connector)
10 device
11 workbench
12 object
100, 100B, 100C, 100D, 100E, and 100F master-slave robot
101, 101B, 101C, 101D, 101E, and 101F control apparatus for master-slave robot
102, 102B, 102C, 102D, 102E, and 102F control apparatus for master arm
103 and 103B control apparatus for slave arm
104 and 104B master arm mechanism
105 slave arm mechanism
110 master motion information obtaining unit
111 physical information obtaining unit
112 master motion information correcting unit
113 force information correcting unit
114 force information presenting unit
115 force information obtaining unit
116 slave controller
117 master input IF
121 force range information generator
122 force information range correcting unit
123 support information obtaining unit
124 support portion correcting unit
125 master weight information obtaining unit
126 arm weight information obtaining unit
127 weight ratio correcting unit
128 task characteristic information obtaining unit
129 task characteristic correcting unit

What is claimed is:
1. A master-slave robot comprising:
a slave arm that performs a task using a slave arm mechanism;

a master arm that has a master arm mechanism and that is remotely manipulated by an operator to allow the slave arm mechanism to make a motion: and control circuitry configured to:
   obtain master motion information including at least one selected from the group consisting of a position, a posture, a speed, and an angular velocity of the master arm mechanism;
   obtain physical information including an arm weight of the operator;
   correct the master motion information based on the physical information in such a manner that the heavier the arm weight of the operator included in the physical information is, the larger the slave arm moves; and
   control the slave arm mechanism, according to the corrected master motion information.

2. The master-slave robot according to claim 1, wherein the control circuitry is further configured to:
   obtain force information including a magnitude of a force externally applied to the slave arm mechanism;
   correct the force information in such a manner that the heavier the arm weight of the operator is, the greater the magnitude of the force; and
   present a force to the arm of the operator through the master arm, based on the corrected force information.

3. The master-slave robot according to claim 2, wherein the physical information includes a magnitude of a maximum force which the arm of the operator withstands as an upper limit;
the physical information includes a magnitude of a minimum force which the arm of the operator feels as a lower limit; and
the control circuitry is further configured to:
   further correct the corrected force information in such a manner that the magnitude of the force presented to the arm of the operator through the master arm falls within a range between the upper limit and the lower limit.

4. The master-slave robot according to claim 1, wherein the control circuitry is further configured to:
   correct the master motion information based on support information including information of a support portion which supports the arm of the operator manipulating the master arm, in such a manner that the closer a position of the support portion is to a hand of the operator manipulating the master arm, the smaller the slave arm moves; and
   control the slave arm mechanism, according to the corrected master motion information.

5. The master-slave robot according to claim 1, wherein the control circuitry is further configured to:
   obtain force information including a magnitude of a force externally applied to the slave arm mechanism;
   correct the force information in such a manner that the heavier the arm weight of the operator is, the greater the magnitude of the force;
   correct the force information based on support information including information of a support portion which supports the arm of the operator manipulating the master arm, in such a manner that the closer a position of the support portion is to a hand of the operator manipulating the master arm, the smaller the magnitude of the force is; and
   present the force to the arm of the operator through the master arm, based on the corrected force information.

6. The master-slave robot according to claim 1, wherein the master arm is changeable; and
the control circuitry is further configured to:
   correct the master motion information in such a manner that the heavier the master arm is, the smaller the slave arm moves.

7. The master-slave robot according to claim 2, wherein the force information is composed of a master arm movement direction component amount which is along movement direction of the master arm, a master arm first perpendicular direction component amount along a first direction which is perpendicular to the movement direction of the master arm, and a master arm second perpendicular direction component amount along a second direction which is perpendicular to the movement direction of the master arm;
the first direction and the second direction are perpendicular to each other; and
the control circuitry is further configured to:
   correct the force information in such a manner that the master arm movement direction is larger whereas the master arm first perpendicular component amount and the master arm second perpendicular component amount are remained unchanged; and
   present the force to the arm of the operator through the master arm, based on the corrected force information.

8. The master-slave robot according to claim 1, further comprising:
   an imaging apparatus which captures an image of an object of the task performed by the slave arm; and
   a display that displays the image for the operator, wherein
   the control circuitry is further configured to:
      obtain a task characteristic information of the operator; and
      correct the corrected master motion information based on the task characteristic information;
   the task characteristic information includes an enlargement factor of the image;
   the enlargement factor is defined by the following formula:

(the enlargement factor)=(size of the object displayed on the display)/(actual size of the object);

and
   the control circuitry is further configured to:
      correct the master motion information in such a manner that the larger the enlargement force is, the larger the slave arm moves, if the object is flexible;
      correct the master motion information in such a manner that the larger the enlargement force is, the smaller the slave arm moves, if the object is rigid; and
      control the slave arm mechanism, according to the corrected master motion information.

9. The master-slave robot according to claim 1, wherein the physical information includes a grip of the arm of the operator; and
the control circuitry is further configured to:
   correct the master motion information based on the physical information in such a manner that the greater the grip of the arm weight of the operator included in the physical information is, the larger the slave arm moves.

10. The master-slave robot according to claim 1, wherein the physical information includes an information of a dominant arm of the operator; and the control circuitry is further configured to:
- correct the master motion information based on the physical information in such a manner that the slave arm moves largely in a case where the master arm is manipulated by the dominant arm of the operator; and
- correct the master motion information based on the physical information in such a manner that the slave arm moves small in a case where the master arm is manipulated by an arm opposite to the dominant arm of the operator.

11. A method for controlling a master-slave robot comprising a slave arm that performs a task using a slave arm mechanism and a master arm that has a master arm mechanism and that is remotely manipulated by an operator to allow the slave arm mechanism to make a motion, the method comprising:
- (a) obtaining master motion information including at least one selected from the group consisting of a position, a posture, a speed, and an angular velocity of the master arm mechanism;
- (b) obtaining physical information including an arm weight of the operator;
- (c) correcting the master motion information based on the physical information in such a manner that the heavier the arm weight of the operator included in the physical information is, the larger the slave arm moves; and
- (d) controlling the slave arm mechanism, according to the corrected master motion information.

12. A computer-readable storage medium storing a program for causing a computer to execute a method for controlling a master-slave robot comprising a slave arm that performs a task using a slave arm mechanism and a master arm that has a master arm mechanism and that is remotely manipulated by an operator to allow the slave arm mechanism to make a motion, the method comprising:
- (a) obtaining master motion information including at least one selected from the group consisting of a position, a posture, a speed, and an angular velocity of the master arm mechanism;
- (b) obtaining physical information including an arm weight of the operator;
- (c) correcting the master motion information based on the physical information in such a manner that the heavier the arm weight of the operator included in the physical information is, the larger the slave arm moves; and
- (d) controlling the slave arm mechanism, according to the corrected master motion information.

13. An integrated circuit for controlling a method performed at a master-slave robot comprising a slave arm that performs a task using a slave arm mechanism and a master arm that has a master arm mechanism and that is remotely manipulated by an operator to allow the slave arm mechanism to make a motion, the method comprising:
- (a) obtaining master motion information including at least one selected from the group consisting of a position, a posture, a speed, and an angular velocity of the master arm mechanism;
- (b) obtaining physical information including an arm weight of the operator;
- (c) correcting the master motion information based on the physical information in such a manner that the heavier the arm weight of the operator included in the physical information is, the larger the slave arm moves; and
- (d) controlling the slave arm mechanism, according to the corrected master motion information.

\* \* \* \* \*